US008097425B2

(12) United States Patent
Urdea et al.

(10) Patent No.: US 8,097,425 B2
(45) Date of Patent: Jan. 17, 2012

(54) MULTIPLEX PROTEIN FRACTIONATION

(75) Inventors: Michael S. Urdea, Alamo, CA (US); Michael P. McKenna, Berkeley, CA (US); Scott Eastman, Danville, CA (US)

(73) Assignee: Tethys Bioscience, Inc., Emeryville, CA (US)

( * ) Notice: Subject to any disclaimer, the term of this patent is extended or adjusted under 35 U.S.C. 154(b) by 728 days.

(21) Appl. No.: 11/717,280

(22) Filed: Mar. 12, 2007

(65) Prior Publication Data

US 2008/0176246 A1 Jul. 24, 2008

Related U.S. Application Data

(60) Provisional application No. 60/781,294, filed on Mar. 10, 2006.

(51) Int. Cl.
*G01N 33/53* (2006.01)
*G01N 31/00* (2006.01)

(52) U.S. Cl. ............ 435/7.21; 435/2; 435/7.1; 436/501; 436/518; 436/522; 530/300; 530/350; 422/50

(58) Field of Classification Search .................. None
See application file for complete search history.

(56) References Cited

U.S. PATENT DOCUMENTS

| | | | |
|---|---|---|---|
| 4,774,339 A | 9/1988 | Haugland et al. | |
| 4,816,567 A | 3/1989 | Cabilly et al. | |
| 5,270,163 A | 12/1993 | Gold et al. | |
| 5,384,263 A | 1/1995 | Kauvar | |
| 5,475,096 A | 12/1995 | Gold et al. | |
| 5,530,101 A | 6/1996 | Queen et al. | |
| 5,538,897 A | 7/1996 | Yates, III et al. | |
| 5,565,332 A | 10/1996 | Hoogenboom et al. | |
| 5,580,717 A | 12/1996 | Dower et al. | |
| 5,585,089 A | 12/1996 | Queen et al. | |
| 5,589,332 A | 12/1996 | Shih et al. | |
| 5,632,041 A | 5/1997 | Peterson et al. | |
| 5,670,637 A | 9/1997 | Gold et al. | |
| 5,693,761 A | 12/1997 | Queen et al. | |
| 5,693,762 A | 12/1997 | Queen et al. | |
| 5,696,249 A | 12/1997 | Gold et al. | |
| 5,701,256 A | 12/1997 | Marr et al. | |
| 5,706,498 A | 1/1998 | Fujimiya et al. | |
| 5,733,743 A | 3/1998 | Johnson et al. | |
| 5,741,679 A | 4/1998 | George et al. | |
| 5,807,715 A | 9/1998 | Morrison et al. | |
| 5,866,692 A | 2/1999 | Shitara et al. | |
| 5,964,860 A | 10/1999 | Peterson et al. | |
| 5,997,867 A | 12/1999 | Waldmann et al. | |
| 6,017,693 A | 1/2000 | Yates, III et al. | |
| 6,054,297 A | 4/2000 | Carter et al. | |
| 6,180,370 B1 | 1/2001 | Queen et al. | |
| 6,180,377 B1 | 1/2001 | Morgan et al. | |
| 6,210,671 B1 | 4/2001 | Co | |
| 6,265,150 B1 | 7/2001 | Terstappen et al. | |
| 6,274,323 B1 | 8/2001 | Bruchez et al. | |
| 6,331,415 B1 | 12/2001 | Cabilly et al. | |
| 6,350,861 B1 | 2/2002 | Co et al. | |
| 6,365,418 B1 | 4/2002 | Wagner et al. | |
| 6,410,245 B1 | 6/2002 | Northrop et al. | |
| 6,579,719 B1 | 6/2003 | Hutchens et al. | |
| 6,824,981 B2 | 11/2004 | Chait et al. | |
| 6,833,441 B2 | 12/2004 | Wang et al. | |
| 7,117,096 B2 | 10/2006 | Luo et al. | |
| 7,175,983 B2 | 2/2007 | Wang et al. | |
| 7,252,954 B2 | 8/2007 | Wang et al. | |
| 7,259,022 B2 * | 8/2007 | Comb et al. ................ 436/547 |
| 2002/0015952 A1 | 2/2002 | Anderson et al. | |
| 2002/0055186 A1 | 5/2002 | Barry et al. | |
| 2002/0182649 A1 | 12/2002 | Weinberger et al. | |
| 2003/0022240 A1 | 1/2003 | Luo et al. | |
| 2003/0054408 A1 | 3/2003 | Ravi et al. | |
| 2003/0119063 A1 | 6/2003 | Pham | |
| 2004/0010376 A1 | 1/2004 | Luo et al. | |
| 2004/0038319 A1 | 2/2004 | Aebersold et al. | |
| 2004/0209255 A1 | 10/2004 | Koster et al. | |
| 2005/0131219 A1 | 6/2005 | Urdea et al. | |
| 2007/0042431 A1 | 2/2007 | Urdea et al. | |

FOREIGN PATENT DOCUMENTS

| | | |
|---|---|---|
| EP | 0 519 596 A1 | 12/1992 |
| EP | 0 519 596 B1 | 12/1992 |
| WO | WO 93/06213 A1 | 4/1993 |
| WO | WO 99/38185 A2 | 7/1999 |
| WO | WO 99/38185 A3 | 7/1999 |
| WO | WO 99/58572 A1 | 11/1999 |
| WO | WO 00/11208 A1 | 3/2000 |
| WO | WO 01/27160 A1 | 4/2001 |
| WO | WO 01/086306 A2 | 11/2001 |
| WO | WO 01/086306 A3 | 11/2001 |

(Continued)

OTHER PUBLICATIONS

Afzalpurkar, A. et al. (1997). "Identification of Epitopes of Monoclonal Antibodies to Porcine Zona Pellucida 3β Glycoprotein, a Homologue of the Mouse/Human Sperm Receptor," *American Journal of Reproductive Immunology* 38:26-32.

Akerblom, L. et al. (1990). "Neutralizing Cross-Reactive and Non-Neutralizing Monoclonal Antibodies to HIV-1 GP120," *AIDS* 4(10):953-960.

Anderson, N. L. et al. (2004, e-pub. Feb. 6, 2004). "An Effective and Rapid Method for Functional Characterization of Immunoadsorbents Using POROS Beads and Flow Cytometry," *Journal of Proteome Research* 3(2):228-234 (2.00).

Anderson, N.L. et al. (2004, e-pub. Feb. 6, 2004). "Mass Spectrometric Quantitation of Peptides and Proteins Using Stable Isotope Standards and Capture by Anti-Peptide Antibodies (SISCAPA)," *Journal of Proteome Research* 3(2):235-244.

(Continued)

*Primary Examiner* — Lisa Cook
(74) *Attorney, Agent, or Firm* — James S. Keddie; Bozicevic, Field & Francis

(57) ABSTRACT

The invention provides methods, compositions, and kits for multiplex fractionation of proteins in a sample. Protein-binding molecules, such as small epitope antibodies or small epitope aptamers, are used for multiplex fractionation of proteins in a protein containing sample. Detection of fractionated proteins may be used for characterization of proteins in a sample in applications such as expression profiling, identification and/or quantification of proteins in a sample, and identification or detection of biomarkers.

9 Claims, 4 Drawing Sheets

FOREIGN PATENT DOCUMENTS

| WO | WO 02/060377 A2 | 8/2002 |
|---|---|---|
| WO | WO 02/060377 A3 | 8/2002 |
| WO | WO 03/027682 A2 | 4/2003 |
| WO | WO 03/027682 A3 | 4/2003 |
| WO | WO-2004/031730 A2 | 4/2004 |
| WO | WO-2004/031730 A3 | 4/2004 |
| WO | WO 2004/035742 A2 | 4/2004 |
| WO | WO 2004/035742 A3 | 4/2004 |
| WO | WO 2004/081575 A1 | 9/2004 |
| WO | WO 2005/019831 A2 | 3/2005 |
| WO | WO 2005/019831 A3 | 3/2005 |

OTHER PUBLICATIONS

Bairoch, A. et al. (1993). "The SWISS-PROT Protein Sequence Data Bank, Recent Developments," *Nucleic Acids Research* 21(13):3093-3096.

Barclay, A.N. (Aug. 2003). "Membrane Proteins with Immunoglobulin-Like Domains—A Master Superfamily of Interaction molecules," *Seminars in Immunology* 15(4):215-223.

Barker, W.C. et al. (1990). "Protein Sequence Database," Chapter 3, in *Molecular Evolution: Computer Analysis of Protein and Nucleic Acid Sequences, Methods in Enzymology*, Doolittle, R.F., ed., Academic Press, Inc.: San Diego, CA, pp. 31-49.

Belov, L. et al. (Jun. 1, 2001). "Immunophenotyping of Leukemias Using a Cluster of Differentiation Antibody Microarray," *Cancer Research* 61:4483-4489.

Bergman, T. (2000). "Ladder Sequencing," *Proteins in Functional Genomics* 88:133-144.

Beste, G. et al. (Mar. 1999). "Small Antibody-Like Proteins With Prescribed Ligand Specificities Derived From the Lipocalin Fold," *Proc. Natl. Acad. Sci. USA* 96:1898-1903.

Bradbury, A.R.M. et al. (Jul. 2004). "Antibodies From Phage Antibody Libraries," *J. Immunol. Methods* 290(1-2):29-49.

Brown, B.A. et al. (Jul. 1, 1987). "Tumor-specific Genetically Engineered Murine/Human Chimeric Monoclonal Antibody," *Cancer Research* 47:3577-3583.

Bruchez, Jr., M. et al. (Sep. 25, 1998). "Semiconductor Nanocrystals as Fluorescent Biological Labels," *Science* 281:2013-2016.

Buck, D. W. et al. (Apr. 1982). "Monoclonal Antibodies Specific for Cell Culture Mycoplasmas," *In Vitro* 18(4):377-381.

Burks, C. et al. (1990). "GenBank: Current Status and Future Directions," Chapter 1, in *Molecular Evolution: Computer Analysis of Protein and Nucleic Acid Sequences, Methods in Enzymology*, Doolittle, R.F., ed., Academic Press, Inc.: San Diego, CA, pp. 3-22.

Chait, B.T. et al. (Oct. 1, 1993). "Protein Ladder Sequencing," *Science* 262:89-92.

Chan, W.C.W. et al. (Sep. 28, 1998). "Quantum Dot Bioconjugates for Ultrasensitive Nonisotopic Detection," *Science* 281:2016-2018.

Chapman, K. (Apr. 2002). "The ProteinChip® Biomarker System from Ciphergen Biosystems: A Novel Proteomics Platform for Rapid Biomarker Discovery and Validation," *Biochemical Society Transactions* 30(2):82-87.

Clackson, T. et al. (Aug. 15, 1991). "Making Antibody Fragments Using Phase Display Libraries," *Nature* 352:624-628.

Coutlee, F. et al. (May 1989). "Comparison of Colorimetric, Fluorescent, and Enzymatic Amplification Substrate Systems in an Enzyme Immunoassay for Detection of DNA-RNA Hybrids," *J. Clin. Microbiol.* 27(5):1002-1007.

Daugherty, B.L. et al, (1991). "Polymerase Chain Reaction Facilitates the Cloning, CDR-Grafting, and Rapid Expression of a Murine Monoclonal Antibody Directed Against the CD18 Component of Leukocyte Integrins," *Nucleic Acids Research* 19(9):2471-2476.

Demangel, C. et al. (2000). "Combining Phage Display and Molecular Modeling to Map the Epitope of a Neutralizing Antitoxin Antibody," *Eur. J. Biochem.* 267:2345-2353.

Esteban, J.M. et al. (May 1987). "New Method for the Chelation of Indium-111 to Monoclonal Antibodies: Biodistribution and Imaging of Athymic Mice Bearing Human Colon Carcinoma Xenografts," *J. Nucl. Med.* 28(5):861-870.

Feldhaus, M.J. et al. (Jul. 2004). "Yeast Display of Antibody Fragments: A Discovery and Characterization Platform," *J. Immunol. Methods* 290(1-2):69-80.

Figeys, D. et al. (1998). "Microfabricated Device Coupled with an Electrospray Ionization Quadrupole Time-of-flight Mass Spectrometer: Protein Identifications Based on Enhanced-resolution Mass Spectrometry and Tandem Mass Spectrometry Data," *Rapid Communications in Mass Spectrometry* 12:1435-1444.

Forrer, P. et al. (Feb. 6, 2004). "Consensus Design of Repeat Proteins," *ChemBioChem* 5(2):183-189.

Griffiths, A.D. et al. (1993). "Human Anti-Self Antibodies With High Specificity from Phage Display Libraries," *The EMBO Journal* 12(2):725-734.

Grønborg, M. et al. (Jul. 2002). "A Mass Spectrometry-based Proteomic Approach for Identification of Serine/Threonine-phosphorylated Proteins by Enrichment with Phospho-specific Antibodies," *Molecular & Cellular Proteomics* 1(7):517-527.

Gygi, S.P. et al. (Oct. 1999). "Quantitative Analysis of Complex Protein Mixtures Using Isotope-Coded Affinity Tags," *Nature Biotechnology* 17:994-999.

Halaby, D.M. et al. (Jul. 1999). "The Immunoglobulin Fold Family: Sequence Analysis and 3D Structure Comparisons," *Protein Engineering* 12(7):563-571.

Harlow, E. et al. (1988). *Using Antibodies: A Laboratory Manual*, Cold Spring Harbor Laboratory Press, Cold Spring Harbor, NY, pp. iii-ix, (Table of Contents only).

Harlow, E. et al. (1988). "Immunizations," Chapter 5, in *Antibodies: A Laboratory Manual*, Cold Spring Harbor Laboratory Press, Cold Spring Harbor, NY, pp. 55-137.

Harlow, E. et al. (1988). Chapter 14 in *Antibodies: A Laboratory Manual*, Cold Spring Harbor Laboratory Press: Cold Spring Harbor, NY, pp. 584-585.

Harlow, E. et al. (1999). *Using Antibodies: A Laboratory Manual*, Cold Spring Harbor Laboratory Press, Cold Spring Harbor, NY, 5 pages, (Table of Contents only).

Harlow, E. et al. eds. (1999). "Immunoprecipitation," Chapter 11, in *Using Antibodies, A Lab Manual*, Cold Spring Harbor Laboratory Press: Cold Spring Harbor, New York, pp. 421-470.

Hollborn, M. et al. (1999). "Epitope Mapping of a Monoclonal Antibody Directed Against the α-Subunit of Phosphofructokinase-1 From *Saccharomyces cerevisiae* by Screening Phage Display Libraries," *J. Mol. Recognit.* 12:33-37.

International Search Report and Written Opinion mailed on Dec. 28, 2007, for PCT Application No. PCT/US2007/006255 filed on Mar. 12, 2007, 15 pages.

Jayasena, S.D. (1999). "Aptamers: An Emerging Class of Molecules That Rival Antibodies in Diagnostic," *Clinical Chem.* 45(9):1628-1650.

Johnson, K.S. et al. (1993). "Human Antibody Engineering," *Current Opinion in Structural Biology* 3:564-571.

Jones, P.T. et al. (May 29, 1986). "Replacing the Complementarity-Determining Regions in a Human Antibody With Those From a Mouse," *Nature* 321:522-525.

Kahn, P. et al. (1990). "EMBL Data Library," Chapter 2, in *Molecular Evolution: Computer Analysis of Protein and Nucleic Acid Sequences, Methods in Enzymology*, Doolittle, R.F., ed., Academic Press, Inc.: San Diego, CA, pp. 23-31.

Kennedy, J.H. et al. (1976). "Protein-Protein Coupling Reactions and the Applications of Protein Conjugates," *Clin. Chim. Acta* 70:1-31.

Keough, T. et al. (Jun. 1999). "A Method for High-Sensitivity Peptide Sequencing Using Postsource Decay Matrix-Assisted Laser Desorption Ionization Mass Spectrometry," *Proc. Natl. Acad. Sci. USA* 96:7131-7136.

Köhler, G. et al. (Aug. 7, 1975). "Continuous Cultures of Fused Cells Secreting Antibody of Predefined Specificity," *Nature* 256:495-497.

Küster, B. et al. (1998). "Identifying Proteins and Post-Translational Modifications by Mass Spectrometry," *Current Opinion in Structural Biology* 8:393-400.

Li, J. et al (2000). "Separation and Identification of Peptides from Gel-Isolated Membrane Proteins Using a Microfabricated Device for Combined Capillary Electrophoresis/Nanoelectrospray Mass Spectrometry," *Anal Chem.* 72:599-609.

Lingjun, L. et al. (Apr. 2000). "Single-Cell MALDI: A New Tool for Direct Peptide Profiling," *Tibtech* 18:151-160.

Lipovsek, D. et al. (Jul. 2004). "In-Vitro Protein Evolution by Ribsome Display and mRNA Display," *J. Immunol. Methods* 290(1-2):51-67.

Lobuglio, A.F. et al. (Jun. 1989). "Mouse/Human Chimeric Monoclonal Antibody in Man: Kinetics and Immune Response," *Proc. Nat. Acad. Sci* 86:4220-4224.

Löfås, S. et al. (Jul. 1, 1990). "A Novel Hydrogel Matrix on Gold Surfaces in Surface Plasmon Resonance Sensors for Fast and Efficient Covalent Immobilizations of Ligands," *J. Chem. Soc., Chem. Commun.* 13:1526-1528.

Lonberg, N. et al. (1995). "Human Antibodies From Transgenic Mice," *Intern. Rev. Immuol.* 13:65-93.

Malmborg, A-C. et al. (Jun. 14, 1995). "BIAcore as a Tool in Antibody Engineering," *J. Immunol. Methods* 183(1):7-13.

Malorny, B. et al. (Mar. 1998). "Sequence Diversity, Predicted Two-Dimensional Protein Structure, and Epitope Mapping of Neisserial Opa Proteins," *Journal of Bacteriology* 180(5):1323-1330.

Marks, J.D. et al. (1991). "By-passing Immunization Human Antibodies from V-Gene Libraries Displayed on Phage," *J. Mol. Biol.* 222:581-597.

Marks, J.D. et al. (Jul. 1992). "By-passing Immunization: Building High Affinity Human Antibodies by Chain Shuffling," *Bio/Technology* 10:779-783.

McCafferty, J. et al. (Dec. 6, 1990). "Phage Antibodies: Filamentous Phage Displaying Antibody Variable Domains," *Nature* 348:552-554.

Michaud, G.A. et al. (Dec. 2003). "Analyzing Antibody Specificity With Whole Proteome Microarrays," *Nature Biotechnology* 21(12):1509-1512.

Moore, C. (1995). "Mass Spectrometry," in *Kirk-Othmer Encyclopedia of Chemical Technology*, 4th Ed., John Wiley & Sons, New York, NY, pp. 1071-1094.

Morelli, G. et al. (1997). "Clonal Descent and Microevolution of *Neisseria meningitidis* During 30 Years of Epidemic Spread," *Molecular Microbiology* 25(6):1047-1064.

Morrison, S.L. et al. (Nov. 1984). "Chimeric Human Antibody Molecules: Mouse Antigen-Binding Domains with Human Constant Region Domains," *Proc. Nat. Acad. Sci.* 81:6851-6855.

Nagasaki, H. et al. (1999). "Epitope Analysis of a Prostate-Specific Antigen (PSA) C-Terminal-specific Monoclonal Antibody and New Aspects for the Discrepancy between Equimolar and Skewed PSA Assays," *Clinical Chemistry* 45(4):486-496.

New England BioLabs. (Date Unknown). "Product Information Sheet for Ph.D.™-7 Phage Display Peptide Library," located at: <http://www.neb.com/nebecomm/productsE8102.asp>, last visited on Mar. 6, 2008, four pages.

Nygren, P-Å. (Jul. 2004). "Binding Proteins From Alternative Scaffolds," *J. Immunol. Methods* 290(1-2):3-28.

Peeters, K. et al. (2001). "Production of Antibodies and Antibody Fragments in Plants," *Vaccine* 19:2756-2761.

Pollock, D.P. et al. (Dec. 10, 1999) "Transgenic Milk as a Method for the Production of Recombinant Antibodies," *J. Immunol Methods* 231(1-2):147-157.

Riechmann, L. et al. (Mar. 24, 1988). "Reshaping Human Antibodies for Therapy," *Nature* 332:323-327.

Roberts, R. W. et al. (Nov. 1997). "RNA-Peptide Fusions for the In Vitro Selection of Peptides and Proteins," *Proc. Natl. Acad. Sci. USA* 94:12297-12302.

Robeva, A. S. et al. (Feb. 23, 1996). "Double Tagging Recombinant $A_1$-and $A_{2A}$-Adenosine Receptors with Hexahistidine and the FLAG Epitope: Development of an Efficient Generic Protein Purification Procedure," *Biochem. Pharmacol.* 51(4):545-555.

Rowley, A. et al. (2000). "Application of Protein Mass Spectrometry in Cell Biology," *Methods* 20:383-397.

Saul, F. A. et al. (1996). "Crystallographic Studies of Antigen—Antibody Interactions," Chapter 2 in *Methods in Molecular Biology: Epitope Mapping Protocols*. Morris, G.E., ed., Humana Press: Totowa, NJ, pp. 11-23.

Schaffitzel, C. et al. (Dec. 10, 1999). "Ribosome Display: An In Vitro Method for Selection and Evolution of Antibodies From Libraries," *J. Immunol. Methods* 231(1-2):119-135.

Schuurs, A.H.W.M. et al. (1977). "Enzyme-Immunoassay," *Clin. Chim. Acta* 81:1-40.

Shaw, D.R. et al. (Jun. 15, 1987). "Characterization of a Mouse/Human Chimeric Monoclonal Antibody (17-1A) to a Colon Cancer Tumor-Associated Antigen," *The Journal of Immunology* 138(12):4534-4538.

Shevchenko, A. et al. (2000). "MALDI Quadrupole Time-of-Flight Mass Spetrometry: A Powerful Tool for Proteomic Research," *Anal. Chem.* 72:2132-2141.

Shin, J.A. (2004). "Minimalist Proteins: Design of New Molecular Recognition Scaffolds," *Pure Appl. Chem.* 76(7-8):1579-1590.

Skerra, A. (Oct. 18, 2000). "Lipocalins as a Scaffold," *BioChimica et Biophysica Acta* 1482(1-2):337-350.

Smith, G.P. (Jun. 14, 1985). "Filamentous Fusion Phage: Novel Expression Vectors That Display Cloned Antigens on the Virion Surface," *Science* 228(4705):1315-1317.

Tsugita, A. et al., eds. (Mar. 1993). "Index of the Protein Sequences Added in 1991 to the Protein Sequence Database of the International Association of Protein Sequence Databanks (PIR-International)," *Protein Sequences and Data Analysis* 5(2-4):67-192.

U.S. Appl. No. 10/921,380, filed Aug. 18, 2004 for Urdea et al. (copy not attached).

U.S. Appl. No. 11/585,507, filed Oct. 23, 2006, for Urdea et al. (copy not attached).

U.S. Appl. No. 11/703,404, filed Feb. 6, 2007, for Hu et al. (copy not attached).

U.S. Appl. No. 11/890,884, filed Aug. 7, 2007, for Urdea et al. (copy not attached).

Verhoeyen, M. et al. (Mar. 25, 1988). "Reshaping Human Antibodies: Grafting an Antilysozyme Activity," *Science* 239:1534-1536.

Waterhouse, P. et al. (1993). "Combinatorial Infection and In Vivo Recombination: A Strategy for Making Large Phage Antibody Repertoires," *Nucleic Acids Research* 21(9):2265-2266.

Weiss, G.A. et al. (Aug. 2000). "Anticalins Versus Antibodies: Made-to-Order Binding Proteins for Small Molecules," *Chemistry & Biology* 7(8):R177-R184.

Winter, G. et al. (Jan. 24, 1991). "Man-Made Antibodies," *Nature* 349:293-299.

Winter, G. et al. (1994). "Making Antibodies by Phage Display Technology," *Annu. Rev. Immunol.* 12:433-455.

Xu, W. et al. (Jul. 1996). "Anti-Peptide Aptamers Recognize Amino Acid Sequence and Bind a Protein Epitope," *Proc. Natl. Acad. Sci. USA* 93:7475-7480.

Yates III, J.R. (1998). "Mass Spectrometry and the Age of the Proteome," *Journal of Mass Spectrometry* 33:1-19.

Zheng, X. et al. (Nov. 1996). "Epitope Mapping of the Variable Repetitive Region within the MB Antigen of *Ureaplasma urealyticum*," *Clinical and Diagnostic Laboratory Immunology* 3(6):774-778.

* cited by examiner

MULTIPLEX PROTEIN FRACTIONATION

CROSS-REFERENCE TO RELATED APPLICATIONS

This application claims the benefit of U.S. Provisional Application No. 60/781,294, filed on Mar. 10, 2006, which is incorporated by reference herein in its entirety.

FIELD OF THE INVENTION

The present invention relates generally to methods for analysis of proteins in a sample. More specifically, the present invention relates to proteomics, the measurement of the protein levels in biological samples, and characterization and analysis of proteins in a sample using multiplex fractionation with protein-binding molecules such as antibodies or aptamers that recognize small epitopes.

BACKGROUND OF THE INVENTION

Proteomics offers a more direct look at the biological functions of a cell or organism than does genomics, the traditional focus for evaluation of gene activity. Proteomics involves the qualitative and quantitative measurement of gene activity by detecting and quantitating expression at the protein level, rather than at the messenger RNA level. Proteomics also involves the study of non-genome encoded events including the post-translational modification of proteins, protein degradation and protein byproducts, interactions between proteins, and the location of proteins within the cell. The structure, function, or level of activity of the proteins expressed by a cell are also of interest.

The study of gene expression at the protein level is important because many of the most important cellular processes are regulated by the protein status of the cell, not by the status of gene expression. Also, the protein content of a cell is highly relevant to drug discovery efforts since most drugs are designed to be active against protein targets.

Current technologies for the analysis of protein mixtures, such as the intracellular proteins of a cell or population of cells and the proteins secreted by the cell or population of cells or biological fluids, are based on a variety of protein separation techniques followed by identification and/or analysis of the separated proteins. The most popular method is based on 2D-gel electrophoresis followed by "in-gel" proteolytic digestion and mass spectroscopy. Alternatively, Edman degradation and related methods may be used for the sequencing. This 2D-gel technique requires large sample sizes, is time consuming, and is currently limited in its ability to reproducibly resolve a significant fraction of the proteins expressed by a human cell. Techniques involving some large-format 2D-gels can produce gels which separate a larger number of proteins than traditional 2D-gel techniques, but reproducibility is still poor and over 95% of the spots cannot be sequenced due to limitations with respect to sensitivity of the available sequencing techniques. The electrophoretic techniques are also plagued by a bias towards proteins of high abundance.

Thus, there is a need for the ability to assay more completely proteins expressed by a cell or a population of cells in an organism or in a fluid comprising protein (such as serum, plasma, lymph, and other biological fluids), including up to the total set of proteins expressed by the cell or cells or found in the fluid comprising protein.

Many currently available methods for protein profiling have severe limitations with respect to sensitivity and throughput. There is a need for improved methods for simultaneously characterizing the large number of proteins found in biological samples.

BRIEF SUMMARY OF THE INVENTION

The invention provides methods, compositions, and kits for multiplex analysis of proteins in a sample.

In one aspect, the invention provides a method for characterizing protein in a sample that comprises a mixture of proteins, comprising: (a) fractionating protein in the sample into fractions with a plurality of first protein-binding molecules; (b) contacting protein in a fraction with a plurality of second protein-binding molecules; and (c) detecting protein bound to the second protein-binding molecules. In one embodiment, each fraction is contacted with a plurality of second protein-binding molecules. In some embodiments, protein bound to the second protein-binding molecules is separated from the protein-binding molecules prior to detection. In one embodiment, each of the second protein-binding molecules comprises a unique detectable label, and step (c) comprises detecting the unique detectable labels. In one embodiment, protein bound to the second protein-binding molecules comprises a first detectable label, each of the second protein-binding molecules comprises a unique second detectable label, and the method comprises detecting both the first and second detectable labels. In one embodiment, the first detectable label is quantitatively detected (for example, determination of amount) and the second detectable label is qualitatively detected (for example, determination of presence or absence). In some embodiments, a fraction is divided into a plurality of portions and each of the portions is contacted with one second protein-binding molecule or with a mixture of two or more second protein-binding molecules. In some embodiments, the plurality of first protein-binding molecules comprises at least about 100 protein-binding molecules and the plurality of second protein-binding molecules comprises at least about 100 protein-binding molecules. In some embodiments, the first and/or second protein-binding molecules are selected from the group consisting of antibodies, aptamers, anticalins, affibodies, and non-immunoglobulin-based binding proteins.

In some embodiments, protein in the sample is contacted with a protein cleaving agent to form polypeptide fragments, and the polypeptide fragments are contacted with the plurality of first protein-binding molecules. In some embodiments, proteins are contacted with a protein cleaving agent after fractionation with the first protein-binding molecules to form polypeptide fragments, and the polypeptide fragments are contacted with a plurality of second small epitope antibodies.

In some embodiments, either the first or the second or both of the first and second protein-binding molecules are small epitope antibodies or aptamers or a combination thereof, and fractionation comprises forming small epitope antibody-protein complexes and/or small epitope aptamer-protein complexes. In one embodiment, the second protein-binding molecules are small epitope antibodies or aptamers or a combination thereof and protein bound to the second small epitope antibodies and/or aptamers is separated from the small epitope antibodies and/or aptamers prior to detection. In one embodiment, the second protein-binding molecules are small epitope antibodies or small epitope aptamers or a combination thereof each comprising a unique detectable label, for example, selected from the group consisting of fluorescent microparticles, microparticles comprising quantum dots, and barcode materials, and the method comprises detecting the unique detectable labels. In one embodiment, the second protein-binding molecules are small epitope antibodies or small epitope aptamers or a combination thereof, protein bound to the small epitope antibodies and/or small epitope aptamers comprises a first detectable label, for example, selected from the group consisting of biotin, avidin, streptavidin, a fluorophor, a radiolabel, a chemiluminescent label, an enzyme, and a magnetic label, and each of the small epitope antibodies and/or small epitope aptamers comprises a unique second detectable label, and the method comprises detecting both the first and second detectable labels. In one embodiment, the first detectable label is quantitatively detected (for example, determination of amount) and the second detectable label is qualitatively detected (for example, determination of presence or absence). In one embodiment, the sample is fractionated with a least about 100 first small epitope antibodies or small epitope aptamers or a combination thereof, and protein in a fraction is further fractionated with at least about 100 second small epitope antibodies or small epitope aptamers or a combination thereof. Small epitope antibodies or small epitope aptamers used in accordance with methods of the invention may each bind epitopes consisting of 3 to 5 contiguous amino acids.

Small epitope antibodies or small epitope aptamers or a combination thereof may optionally be immobilized on a solid matrix. In one embodiment, first small epitope antibodies or small epitope aptamers or a combination thereof are immobilized on a solid matrix, and fractionated proteins in first small epitope antibody-protein complexes and/or first small epitope aptamer-protein complexes are eluted into an aqueous medium prior to contact with second small epitope antibodies or small epitope aptamers or a combination thereof, which are optionally immobilized on a solid matrix.

In one embodiment, the method comprises (a) contacting a plurality of first separate portions of the sample with a set of first small epitope antibodies or small epitope aptamers or a combination thereof, wherein each of the first portions is contacted with one small epitope antibody or small epitope aptamer or with a mixture of two or more small epitope antibodies or small epitope aptamers or a combination thereof, thereby forming first fractions comprising first small epitope antibody-protein complexes and/or small epitope aptamer-protein complexes, (b) contacting a plurality of second separate portions of protein from the first small epitope antibody-protein complexes and/or small epitope aptamer-protein complexes from a first fraction with a set of second small epitope antibodies or small epitope aptamers or a combination thereof, thereby forming second fractions comprising second small epitope antibody-protein complexes and/or small epitope aptamer-protein complexes, wherein each of the second portions is contacted with one small epitope antibody or small epitope aptamer or with a mixture of two or more second small epitope antibodies or small epitope aptamers or a combination thereof, wherein each of the second small epitope antibodies or small epitope aptamers comprises a unique detectable label, and (c) detecting one or more of the detectable labels bound to one or more proteins in the sample. The first and/or second set of small epitope antibodies and/or small epitope aptamers may comprise at least about 100 small epitope antibodies and/or small epitope aptamers. The first and second sets of small epitope antibodies and/or small epitope aptamers may comprise the same or different small epitope antibodies and/or small epitope aptamers, or at least some of the small epitope antibodies or small epitope aptamers may be different between the two sets.

In one embodiment, the method comprises (a) contacting the sample with a set of first small epitope antibodies or small epitope aptamers or a combination thereof, wherein the set of first small epitope antibodies and/or small epitope aptamers comprises a plurality of different small epitope antibodies and/or small epitope aptamers each recognizing a different epitope, thereby forming first small epitope antibody-protein complexes and/or small epitope aptamer-protein complexes, wherein each of the first small epitope antibodies or small epitope aptamers comprises a unique first detectable label, (b) contacting the first small epitope antibody-protein complexes and/or small epitope aptamer-protein complexes with a set of second small epitope antibodies or small epitope aptamers or a combination thereof, wherein the set of second small epitope antibodies and/or small epitope aptamers comprises a plurality of different small epitope antibodies and/or small epitope aptamers that recognize different epitopes than the epitopes recognized by the first small epitope antibodies and/or small epitope aptamers, wherein each of the second small epitope antibodies and/or small epitope aptamers comprises a unique second detectable label, and wherein the second detectable labels are different than the first detectable labels, and (c) detecting at least one of the first or second detectable labels bound to one or more proteins in the sample. In some embodiments, characterization of protein in accordance with methods of the invention comprises determining the identity of at least one protein in the sample. In some embodiments, characterization of protein comprises characterization of protein comprises determining the amount of at least one protein in the sample. In some embodiments, characterization of protein comprises determining the presence or absence of at least one protein in the sample.

In another aspect, the invention provides a method of identifying a protein in a sample, comprising: (a) contacting protein in a sample with a first small epitope antibody or small epitope aptamer that recognizes a first small epitope, thereby forming a first small epitope antibody-protein or small epitope aptamer-protein complex; (b) contacting protein in the first small epitope antibody-protein complex or small epitope aptamer-protein complex with a second small epitope antibody or small epitope aptamer that recognizes a second small epitope, thereby forming a second small epitope antibody-protein complex or small epitope aptamer-protein complex, wherein the second small epitope antibody-protein complex or small epitope aptamer-protein complex comprises protein comprising the first small epitope and the second small epitope; and (c) reviewing known amino acid sequences of proteins from the organism from which the sample was derived to identify one or more proteins comprising the first and second small epitopes, whereby protein in the second small epitope antibody-protein complex or small epitope aptamer-protein complex is identified as said one or more proteins.

In another aspect, the invention provides a method for characterizing protein in a sample that comprises a mixture of proteins, comprising (a) contacting protein in the sample with a protein cleaving agent, wherein the protein cleaving agent cleaves at a cleavage site to produce as set of polypeptide fragments comprising a C-terminal amino acid at the cleavage site, and wherein the polypeptide fragments comprise internal small epitopes; (b) fractionating the polypeptide fragments into fractions with a plurality of first protein-binding molecules, wherein the first protein-binding molecules bind to small epitopes comprising the C-terminal amino acid; (c) contacting polypeptide fragments in at least one of the fractions with a plurality of second protein-binding molecules, wherein the second protein-binding molecules bind to the internal epitopes; and (d) detecting protein bound to the second protein-binding molecules. In one embodiment, each of the second protein-binding molecules comprises a unique detectable label and the method comprises detecting the labels. In one embodiment, the small epitopes comprising a C-terminal amino acid consist of 3 to 5 amino acids. In one embodiment, the internal epitopes consist of 3 to 5 amino acids. In some embodiments, the first and/or second protein-binding molecules are small epitope antibodies or small epitope aptamers or a combination thereof. In some embodiments, the first and/or second protein-binding molecules are selected from the group consisting of antibodies, aptamers, anticalins, affibodies, and non-immunoglobulin-based binding proteins. In some embodiments, characterization of protein comprises determining the identity, amount, and/or presence or absence of at least one protein in the sample.

In another aspect, the invention provides a method for characterizing protein in a sample that comprises a mixture of proteins, comprising (a) contacting protein in the sample with a protein cleaving agent wherein the protein cleaving agent cleaves at a cleavage site to produce a set of polypeptide fragments comprising a C-terminal amino acid at the cleavage site; (b) contacting the polypeptide fragments with a plurality of protein-binding molecules wherein the protein-binding molecules bind to small epitopes comprising the C-terminal amino acid; and (c) detecting unbound polypeptide fragments. In one embodiment, the polypeptide fragments comprise a detectable label and detecting unbound polypeptide fragments comprises detecting the detectable label. In one embodiment, protein bound to the protein-binding molecules is separated from the unbound protein prior to detection. In some embodiments, the protein-binding molecules are small epitope antibodies or small epitope aptamers or a combination thereof. In some embodiments, the protein-binding molecules are selected from the group consisting of antibodies, aptamers, anticalins, affibodies, and non-immunoglobulin-based binding proteins.

In another aspect, the invention provides compositions comprising a plurality of protein-binding molecules, such as a plurality of small epitope antibodies or small epitope aptamers, each comprising a unique detectable label, complexes comprising proteins bound to the protein-binding molecules, or proteins fractionated according to the methods described herein. The invention also provides proteins or polypeptide fragments thereof prepared and/or characterized by any of the fractionation methods described herein.

In another aspect, the invention provides kits comprising protein-binding molecules, such as small epitope antibodies or small epitope aptamers or a combination thereof, for use in the fractionation methods described herein. In one embodiment, the kit comprises a first plurality of protein-binding molecules for performing a first fractionation of proteins and a second plurality of protein-binding molecules for performing a second fractionation of proteins in fractions generated in the first fractionation, wherein the protein-binding molecules for use in the first fractionation and the protein-binding molecules for use in the second fractionation may be the same or different. In one embodiment, the kit comprises a plurality of protein-binding molecules for use in a fractionation method as described herein, wherein each of the protein-binding molecules comprises a unique detectable label. In some embodiments, kits comprise instructions for performing any of the methods described herein.

DETAILED DESCRIPTION OF THE INVENTION

Figure 1:
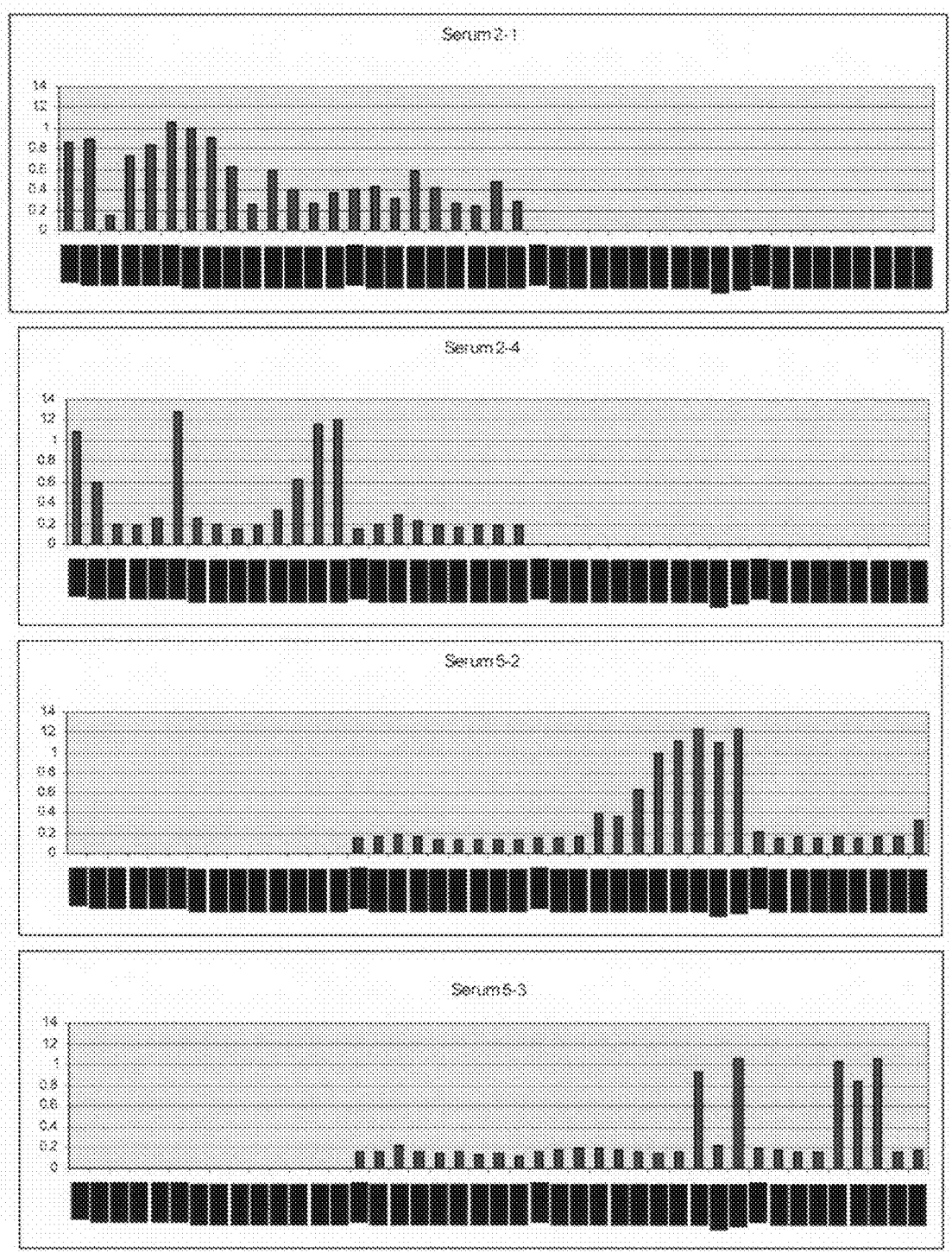
FIG. 1 shows the reaction pattern using mapping polypeptides spanning sequences of immunization polypeptides for group 2 and group 5 mice, respectively.

The invention provides methods using molecules that bind (generally, specifically bind) proteins, termed "protein-binding molecules" herein, to fractionate a protein mixture, whereby protein(s) comprising an amino acid sequence recognized by the protein-binding molecules are isolated, separated, prepared, purified and/or enriched.

In some embodiments, antibodies that bind small protein epitopes (termed "small epitope antibodies") are used, and proteins are fractionated based on the presence and/or quantity of small epitopes within protein in the protein mixture that are recognized by the small epitope antibodies, whereby protein(s) comprising the small epitopes are isolated, separated, prepared, purified and/or enriched. In some embodiments, aptamers that bind small protein epitopes (termed "small epitope aptamers") are used, and proteins are fractionated based on the presence and/or quantity of small epitopes within protein in the protein mixture that are recognized by the small epitope aptamers, whereby protein(s) comprising the small epitopes are isolated, separated, prepared, purified and/or enriched. Insofar as a small epitope bound by a small epitope antibody or small epitope aptamer is known, binding by the small epitope antibody or small epitope aptamer provides information relating to amino acid content of protein(s) bound by the small epitope antibody or small epitope aptamer. Small epitope antibodies, small epitope aptamers and other protein-binding molecules that may be used in accordance with the invention are further described herein. Embodiments of the fractionation methods of the invention described herein with respect to protein-binding molecules encompass the use of small epitope antibodies and the use of small epitope aptamers, and embodiments described with respect to formation of small epitope antibody-protein complexes and small epitope aptamer-protein complexes also apply to formation of other protein-binding molecule-protein complexes.

The methods generally comprise fractionating proteins in a sample that contains a mixture of proteins into fractions by contacting proteins in the sample with a plurality of first protein-binding molecules, and further fractionating protein bound to the plurality of first protein-binding molecules by contacting proteins in a fraction with a plurality of second protein-binding molecules. As used herein, "plurality" refers to at least two different protein-binding molecules. In some embodiments, each of the fractions produced by contacting proteins with the plurality of first protein-binding molecules is further fractionated with a plurality of second protein-binding molecules. Each fraction may be contacted with the same plurality of second protein-binding molecules or fractions may be contacted with different protein-binding molecules. In some embodiments, proteins are digested with a protein cleaving agent and a plurality of first protein-binding molecules bind to a plurality of C-terminal epitopes and a plurality of second protein-binding molecules bind to a plurality of internal epitopes. A C-terminal epitope refers to a small epitope at the carboxyl terminus of a protein, polypeptide fragment, etc. produced by digestion with a protein cleaving agent. The C-terminal epitopes produced by a protein cleaving agent will usually contain a constant or "constrained" amino acid at the extreme carboxyl end of the protein fragment. An "internal epitope" refers to an epitope that is within a protein, polypeptide fragment, etc. and is usually different than a C-terminal epitope. Internal epitopes do not have a constrained amino acid at any position of the epitope. Proteins bound to the second protein-binding molecules may be detected in a method for characterizing protein in a sample. In some embodiments, proteins or protein fragments are bound to the first protein-binding molecules specific for C-terminal epitopes, the complexes are removed and unbound proteins or protein fragments (true C-terminus fragments) are detected. In some embodiments, after proteins are bound to the second protein-binding molecules, unbound proteins may be detected. In some embodiments, at least one of the first and second fractionations comprise binding of proteins to small epitope antibodies as described herein. In some embodiments, at least one of the first and second fractionations comprise binding of proteins to small epitope aptamers. In other embodiments, at least one of the first and second fractionations comprises binding to a protein-binding molecule, such as an antibody that binds to a specific protein or to a class of proteins, a molecular imprint, a lectin, or a capture compound (for example, as described in U.S. Patent Application No. 2004/0209255). Use of the methods of the invention thereby provides a means for reducing the complexity of a protein mixture, facilitating subsequent use and/or characterization of the enriched protein components of the sample.

As a general overview, the methods comprise fractionating a protein-containing sample, whereby a first set of protein fractions results, and further fractionating at least one of the first protein fractions, whereby a second set of protein fractions results. The fractionations are effected with protein-binding molecules, such as, for example, small epitope antibodies or small epitope aptamers. Proteins in the fractions resulting from the second fractionation may be detected, thereby providing information about the protein content in the sample. In some embodiments, after the first and/or second or subsequent fractionation, the unbound protein may be detected, thereby providing information about the protein content of the sample. In some embodiments, the methods further comprise treatment of the sample with a protein cleaving agent prior to or after the first or second fractionation. In some embodiments, proteins in the sample are labeled with a detectable label. In some embodiments, the second fractionation comprises contacting proteins in fractions resulting from the first fractionation with a plurality of protein-binding molecules, such as, for example, small epitope antibodies or small epitope aptamers, wherein each protein-binding molecule comprises a unique detectable label.

As noted in the definition, and as used herein, "sample" encompasses a variety of sample types, including those obtained from an individual. In some embodiments, the sample comprises blood, plasma, serum, urine, stool, cerebrospinal fluid, synovial fluid, amniotic fluid, saliva, lung lavage, semen, milk, nipple aspirate, prostatic fluid, mucous, or tears. Suitable samples for use in the methods of the invention are described further herein.

In some embodiments, methods of the invention comprise the use of "small epitope antibodies" or the use of "small epitope aptamers" that recognize epitopes that are present in a multiplicity of proteins (such as, for example, an epitope consisting of or consisting essentially of 3 linear amino acids, 4 linear amino acids, or 5 linear amino acids). Small epitope antibodies suitable for use in the methods of the invention are extensively described herein and exemplified in the Examples. Such antibodies are also described in pending U.S. application Ser. Nos. 10/687,174 (publication no. 2004/0166106) and 10/921,380 (publication no. 2005/0131219), and in PCT Publication Nos. WO 04/035742 and WO 05/019831. Small epitope aptamers suitable for use in the methods of the invention may be produced by methods known in the art and described herein.

By virtue of the specificity of the small epitope antibodies and small epitope aptamers, proteins (e.g., polypeptides) are fractionated based on the presence and/or amount of a small epitope within a protein recognized by a small epitope antibody or small epitope aptamer used in the methods of the invention. Methods using the protein prepared via the methods of the invention are further described herein. As is evident, "reducing the complexity of a sample" or "fractionation" as used herein, encompasses isolating, purifying, separating, enriching and/or purifying proteins (e.g., polypeptides) from a sample. Accordingly, the invention provides methods for purifying and/or enriching protein, methods for isolating protein, methods for separating protein, methods for preparing protein for characterization, methods for preparing protein for mass spectrometry analysis, methods for identifying protein (such as one or a group of proteins), methods for discovering new protein, methods for expression profiling, and methods for quantification of protein in a sample.

In one embodiment, the invention provides methods for reducing the complexity of a protein-containing sample, said methods comprising: (a) contacting a sample with a first set of small epitope antibodies under conditions that permit binding, thereby forming first small epitope antibody-protein complexes; (b) contacting proteins from the first small epitope-antibody complexes with a second set of small epitope antibodies, thereby forming second small epitope antibody-protein complexes; and (c) detecting protein bound to the second small epitope antibodies. In some embodiments, the second small epitope antibodies each comprise a unique detectable label, and detection comprises detecting the detectable labels. In some embodiments, the proteins comprise a first detectable label and the second small epitope antibodies each comprise a unique second detectable label, and detection comprises detecting both the first and the second detectable labels. Proteins may optionally be separated from the second small epitope antibodies prior to detection. In some embodiments, the proteins comprise a detectable label and detection comprises detecting the unbound protein fraction.

In one embodiment, the invention provides methods for reducing the complexity of a protein-containing sample, said methods comprising: (a) contacting a sample with a protein cleaving agent to form polypeptide fragments; (b) contacting the polypeptide fragments with a first set of small epitope antibodies which bind to C-terminal epitopes under conditions that permit binding, thereby forming first small epitope antibody-polypeptide fragment complexes; (c) contacting proteins from the first small epitope antibody-polypeptide fragment complexes with a second set of small epitope antibodies which bind to internal epitopes, thereby forming second small epitope antibody-polypeptide fragment complexes; and (d) detecting protein bound to the second small epitope antibodies. In some embodiments, the second small epitope antibodies each comprise a unique detectable label, and detection comprises detecting the detectable labels. In some embodiments, the protein comprises a first detectable label and the second small epitope antibodies each comprise a unique second detectable label, and detection comprises detecting both the first and the second detectable labels. Polypeptide fragments may optionally be separated from the second small epitope antibodies prior to detection. In some embodiments, the protein sample comprises a detectable label and detection comprises detecting the unbound polypeptide fragment fraction.

In one embodiment, the invention provides methods for reducing the complexity of a protein-containing sample, said methods comprising: (a) contacting a sample with a first set of small epitope aptamers under conditions that permit binding, thereby forming first small epitope-aptamer complexes; (b) contacting proteins from the first small epitope-aptamer complexes with a second set of small epitope aptamers, thereby forming second small epitope-aptamer complexes; and (c) detecting protein bound to the second small epitope aptamers. In some embodiments, the second small epitope aptamers each comprise a unique detectable label, and detection comprises detecting the detectable labels. In some embodiments, the proteins comprise a first detectable label and the second small epitope aptamers each comprise a unique second detectable label, and detection comprises detecting both the first and the second detectable labels. Proteins may optionally be separated from the second small epitope aptamers prior to detection. In some embodiments, the proteins comprise a detectable label and detection comprises detecting the unbound protein fraction.

In one embodiment, the invention provides methods for reducing the complexity of a protein-containing sample, said methods comprising: (a) contacting a sample with a protein cleaving agent to form polypeptide fragments; (b) contacting the polypeptide fragments with a first set of small epitope aptamers which bind to C-terminal epitopes under conditions that permit binding, thereby forming first small epitope aptamer-polypeptide fragment complexes; (c) contacting proteins from the first small epitope aptamer-polypeptide fragment complexes with a second set of small epitope aptamers which bind to internal epitopes, thereby forming second small epitope aptamer-polypeptide fragment complexes; and (d) detecting protein bound to the second small epitope aptamers. In some embodiments, the second small epitope aptamers each comprise a unique detectable label, and detection comprises detecting the detectable labels. In some embodiments, the protein comprises a first detectable label and the second small epitope aptamers each comprise a unique second detectable label, and detection comprises detecting both the first and the second detectable labels. Polypeptide fragments may optionally be separated from the second small epitope aptamers prior to detection. In some embodiments, the protein sample comprises a detectable label and detection comprises detecting the unbound polypeptide fragment fraction.

In some embodiments, the invention further provides methods for purifying and/or enriching protein, isolating protein, separating protein, preparing protein for characterization, preparing protein for mass spectrometry analysis, identifying protein (such as one or more protein, or a group of proteins), discovering a new protein, expression profiling, and/or quantification of protein in a sample, using the methods described herein for fractionation of proteins in a protein-containing sample, i.e., reducing the complexity of a sample.

In another aspect, the invention also encompasses methods using the protein fractionated via any of the methods of the invention as described herein, for example, methods of expression profiling, methods of identifying proteins, methods for identifying protein degradation products, methods for identifying change in post-translational modification, and methods for determining the mass, the amount and/or identity of protein(s) in a sample. For example, these methods can be applied in such areas as protein discovery, expression profiling, drug discovery and diagnostics.

In some embodiments, a protein-containing sample is fractionated with any of about 10, 20, 30, 40, 50, 75, 100, 125, 150, 200, 300, 400, 500, 1000, or more protein-binding molecules, such as small epitope antibodies or small epitope aptamers. In some embodiments, the sample is fractionated with any of at least about 10, 20, 30, 40, 50, 75, 90, 100, 125, 150, 200, 300, 400, 500, 1000, or more protein-binding molecules, such as small epitope antibodies or small epitope aptamers. In some embodiments, the sample is fractionated with any of at least about 10, 20, 30, 40, 50, 75, 90, 100, 125, 150, 200, 300, 400 or 500, with an upper limit of any of any of about 20, 30, 40, 50, 75, 100, 125, 150, 200, 300, 400, 500, or 1000 protein-binding molecules, such as small epitope antibodies or small epitope aptamers.

In some aspects, the invention provides compositions and kits comprising 10 or more protein-binding molecules, such as small epitope antibodies or small epitope aptamers, for use in any of the methods of the invention. In one embodiment, the invention provides a kit comprising at least about 100 protein-binding molecules, such as small epitope antibodies or small epitope aptamers, for use in a first fractionation procedure in accordance with the methods described herein, and at least about 100 protein-binding molecules, such as small epitope antibodies or small epitope aptamers, for use in a second fractionation of a least one fraction produced in the first fractionation procedure in accordance with the methods described herein, wherein the protein-binding molecules for use in the first fractionation and the protein-binding molecules for use in the second fractionation may be the same or different. In some embodiments, the kits comprise a plurality of protein-binding molecules, such as small epitope antibodies or small epitope aptamers, for use in the second fractionation, wherein protein-binding molecule comprises a unique detectable label. In some embodiments, the kits further comprise at least one protein cleaving agent. In some embodiments, the kits further comprise instructions for carrying out any of the methods described herein. The invention also provides proteins or polypeptide fragments thereof prepared and/or characterized by any of the fractionation methods described herein.

General Techniques

The practice of the present invention will employ, unless otherwise indicated, conventional techniques of molecular biology (including recombinant techniques), microbiology, cell biology, biochemistry, chemistry and immunology, which are within the skill of the art.

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible polypeptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies (as opposed to polyclonal antibodies) are highly specific, in the sense that they are directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention, for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein "epitope" refers to the part of a macromolecule that is recognized by a protein-binding molecule. Traditionally, epitope refers to the part of a macromolecule that is recognized by the immune system, specifically by antibodies, B cells, helper T cells and cytotoxic T cells to produce an immune response. As used herein, epitopes may be recognized and bound by a variety of protein-binding molecules including but not limited to, antibodies, nucleic acid ligands (e.g. aptamers), affibodies, anticalins, monobodies, nanobodies, etc.

Many epitopes are three-dimensional surface features of an antigen molecule (i.e. conformational epitopes) and can be bound precisely by specific antibodies or other protein-binding molecules. Epitopes may also be linear, e.g. wherein the epitope is defined by a primary amino acid sequence and not the tertiary structure of the protein.

As used herein, "small epitope" refers to a short, linear peptide of 2, 3, 4, 5, 6, 7, 8, 9, or 10 amino acids. Encompassed within this definition, "small epitope" may refer to a peptide of 3, 4, or 5 sequential (consecutive) amino acids. Alternatively, "small epitope" may refer to a discontinuous amino acid sequence within a polypeptide consisting essentially of 2, 3, 4, 5, 6, 7, 8, 9, or 10 amino acids.

As used herein, "C-terminal epitope" or a "small epitope comprising a C-terminal amino acid" refers to an epitope at the carboxyl terminus of a protein, a polypeptide fragment, etc. Encompassed within this definition, a "C-terminal epitope" or a "small epitope comprising a C-terminal amino acid" may refer to an epitope at the carboxyl terminus of a polypeptide fragment after cleavage with a protein cleaving agent. As used herein, "internal epitope" refers to an epitope that is within a protein, polypeptide fragment, etc. and is usually different than a C-terminal epitope.

An epitope that "specifically binds" or "preferentially binds" (used interchangeably herein) to an antibody is a term well understood in the art, and methods to determine such specific or preferential binding are also well known in the art. These terms and methods may be extended to cover other protein-binding molecules, e.g. aptamers. A molecule is said to exhibit "specific binding" or "preferential binding" if it reacts or associates more frequently, more rapidly, with greater duration and/or with greater affinity with a particular cell or substance than it does with alternative cells or substances. As used herein, a "binding molecule" e.g. antibody or aptamer "specifically binds" or "preferentially binds" to a target if it binds with greater affinity, avidity, more readily, and/or with greater duration than it binds to other substances. For example, an antibody that specifically or preferentially binds to an epitope is an antibody that binds this epitope with greater affinity, avidity, more readily, and/or with greater duration than it binds to other epitopes. It is also understood by reading this definition that, for example, a binding molecule (e.g. antibody or aptamer) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "sample" encompasses a variety of sample types, including those obtained from an individual. The definition encompasses blood and other liquid samples of biological origin, solid tissue samples such as a biopsy specimen or tissue cultures or cells derived therefrom, and the progeny thereof. A sample can be from a microorganism (e.g., bacteria, yeasts, viruses, viroids, molds, fungi) plant, or animal, including mammals such as humans, rodents (such as mice and rats), and monkeys (and other primates). A sample may comprise a single cell or more than a single cell. The definition also includes samples that have been manipulated in any way after their procurement, such as by treatment with reagents, solubilization, or enrichment for certain components, such as proteins or polynucleotides. The term "sample" encompasses a clinical sample, and also includes cells in culture, cell supernatants, cell lysates, serum, plasma, biological fluid, human tissue propagated in animals, and tissue samples. Examples of a sample include blood, plasma, serum, urine, stool, cerebrospinal fluid, synovial fluid, amniotic fluid, saliva, lung lavage, semen, milk, nipple aspirate, prostatic fluid, mucous, and tears.

The "complexity" of a sample means the number of different protein species, including number of different proteins as well as number of different protein variants (including splice variants, polymorphisms, and protein degradation products).

"Detect" refers to identifying (determining) the presence, absence and/or amount of the object or substance to be detected, and as described herein, detection may be qualitative and/or quantitative.

"Multiplex" refers to simultaneous characterization, e.g., detection, identification, quantitation, of more than one molecule in a sample being analyzed.

An "aptamer" or "nucleic acid ligand" refers to a nucleic acid, e.g., RNA, DNA, or modified RNA or DNA, that specifically binds to a target molecule, e.g., amino acid, carbohydrate, antibiotics, protein, by virtue of the three-dimensional structure of the nucleic acid, which provides specific contact points for interaction with the target molecule.

"Fractionation" refers to separation of a sample or components of a sample into separate portions or "fractions." Generally, after fractionation of a sample, the composition (e.g., mixture of proteins) in at least some of the fractions is different than the sample from which the fraction was derived and is reduced in complexity (e.g., contains fewer proteins) in comparison to the sample from which the fraction was derived.

As used herein, the singular form "a", "an", and "the" includes plural references unless indicated otherwise. For example, "an" antibody includes one or more antibodies and "a protein" means one or more proteins.

"Microarray" and "array," as used interchangeably herein, comprises a surface with an array, preferably ordered array, of putative binding sites for proteins.

"Unique detectable label" refers to a detectable molecule or substance which is uniquely coded such that it may be distinguished from other unique detectable labels.

Methods of the Invention

As a general overview, the methods comprise fractionation of proteins in a protein-containing sample in at least two "dimensions," comprising fractionating proteins by contacting proteins in the sample with a first plurality of protein-binding molecules (i.e., two or more different protein-binding molecules) to produce a first set of fractions each containing a subset of proteins from the original sample, and further fractionating the proteins in at least one first fraction into a second set of fractions, wherein proteins in each second fraction are contacted with one or more second protein-binding molecules. Proteins bound to the second protein-binding molecule(s) in each of the second set of fractions are detected (optionally, proteins are separated from protein-binding molecules prior to detection). Methods of the invention are useful for characterizing protein in a sample, for example, determining the identity, amount, and/or presence or absence of at least one protein in the original sample and/or in a second fraction. "Fractionation," as used herein, encompasses isolating, purifying, separating, enriching and/or purifying proteins or peptides (e.g., polypeptides) from a sample (including removing the proteins or peptides from the environment of the sample).

Methods of the invention provide a powerful multiplex analysis tool by utilizing fractionation in at least two "dimensions." For example, a 100 by 100 fractionation (fractionation into 100 fractions, and fractionation of each of those fractions into 100 fractions) will produce 10,000 different pools derived from an original complex sample. In some embodiments, proteins in a sample are labeled with a universal label or tag, and protein-binding molecules which are used in at least one of the fractionation steps (for example, small epitope antibodies or small epitope aptamers) are each labeled with uniquely identifiable, coded, labels or tags, and the protein signal and antibody signal are detected simultaneously or sequentially to characterize proteins in the sample. In some embodiments, more than two fractionations are performed, for example, 3, 4, 5, or more fractionations.

In some embodiments, the methods further comprise treating the sample with a protein cleaving agent to form polypeptide fragments. Protein cleaving agents that cleave at specific amino acid sequences are most useful, (for example, trypsin which cleaves at Arg and Lys residues or V8 protease which cleaves at Glu residues). Digestion with a protein cleaving agent produces protein fragments with a constant or constrained C-terminal amino acid residue (with the possible exception of the true C-termini of the original proteins in the sample). A constrained C-terminal amino acid residue decreases the number of small epitopes available for detection by protein-binding molecules and may be used as a means to simplify analysis.

In one embodiment, the protein cleaving agent is added prior to fractionation of protein in the protein-containing sample with protein-binding molecules. In another embodiment, the protein cleaving agent is added prior to contacting protein in a fraction from a first fractionation with a second plurality of protein-binding molecules. In another embodiment, the protein cleaving agent is added after a second or subsequent fractionation and prior to detecting protein. In one embodiment, the protein sample is treated with a protein cleaving agent, the protein is fractionated with protein-binding molecules and the unbound polypeptide fragment(s) is detected. In another embodiment, the protein sample is treated with a protein cleaving agent, the protein fragments are fractionated with protein-binding molecules specific for C-terminal epitopes, the complexes are removed and the unbound polypeptide fragment(s) is detected (i.e. the true C-termini of proteins in original sample). In one embodiment, the protein-binding molecules used for at least one fractionation are small epitope antibodies, protein is separated from small epitope antibody-protein complexes prior to treatment with a protein cleaving agent, and the resulting polypeptide fragments are detected. In one embodiment, the protein-binding molecules used for at least one fractionation are small epitope aptamers, protein is separated from small epitope aptamer-protein complexes prior to treatment with a protein cleaving agent, and the resulting polypeptide fragments are detected. In one embodiment, the protein-binding molecules used for at least one fractionation are small epitope aptamers, the protein is fractionated after treatment with a cleaving agent, the protein is separated from the small epitope aptamer-protein complexes, and the polypeptide fragments are detected.

In some embodiments, a sample or fraction is divided into a plurality of portions (i.e., two or more portions), and each of the portions is contacted with one or more protein-binding molecule(s), such as, for example, a small epitope antibody, a small epitope aptamer, a mixture of two or more different small epitope antibodies or a mixture of two or more different small epitope aptamers.

A sample or fraction may be divided into any of at least about 10, 20, 30, 40, 50, 60, 70, 80, 90, 100, 200, 300, 400, 500, 600, 700, 800, 900, or 1000 portions. In one embodiment, a sample or fraction is divided into portions and each portion is contacted with one or more protein-binding molecule(s), such as, for example, one or more small epitope antibody(ies) or one or more small epitope aptamer(s) in each of the wells of a microtiter plate, for example, a 96-well or 384-well plate.

In some embodiments, a sample or fraction is fractionated by contact of the sample or fraction with and binding of proteins in the sample or fraction to protein-binding molecules immobilized on a solid matrix. In one embodiment, a sample or fraction is contacted with protein-binding molecules immobilized on pins, wherein each pin contains one or more protein-binding molecule(s), such as, for example, one or more small epitope antibody(ies) or small epitope aptamers. Proteins may be eluted from each pin for further fractionation and/or detection. In another embodiment, a sample or fraction is contacted with protein-binding molecules immobilized on beads (e.g., microparticles), wherein each bead contains one or more protein-binding molecule(s), such as, for example, one or more small epitope antibody(ies) or one or more small epitope aptamer(s). Proteins may be eluted from each bead for further fractionation and/or detection. In another embodiment, a sample or fraction is contacted with protein-binding molecules immobilized as an array on a solid matrix. Proteins may be eluted from the protein-binding molecules of the array for further fractionation and/or detection.

In some embodiments, a protein-containing sample is fractionated with any of about 10, 20, 30, 40, 50, 75, 100, 125, 150, 200, 300, 400, 500, 1000, or more protein-binding molecules. In some embodiments, the sample is fractionated with any of at least about 10, 20, 30, 40, 50, 75, 90, 100, 125, 150, 200, 300, 400, 500, 1000, or more protein-binding molecules. In some embodiments, the sample is fractionated with any of at least about 10, 20, 30, 40, 50, 75, 90, 100, 125, 150, 200, 300, 400 or 500 protein-binding molecules, with an upper limit of any of about 20, 30, 40, 50, 75, 100, 125, 150, 200, 300, 400, 500, or 1000 protein-binding molecules.

The invention further provides methods for purifying and/or enriching protein, isolating protein, separating protein, preparing protein for characterization (e.g., subsequent analysis), preparing protein for mass spectrometry analysis, identifying protein, discovering new protein, and/or quantification of protein in a sample, wherein protein in the sample is fractionated according to any of the methods described herein.

The invention provides proteins characterized, fractionated, or enriched according to any of the methods described herein.

As is evident, in the methods described herein, one or more steps may be combined and/or performed sequentially (often in any order, as long as proteins are fractionated and detectable), and, as is evident, the invention includes various combinations of the steps described herein.

It is further understood that the protein components of the sample that remain following treatment with protein-binding molecules (i.e., the unbound components) may also be suitable for characterization. Thus, in some embodiments, methods of characterization as described herein encompass use of this unbound protein fraction.

The proteins isolated or enriched using the methods of the invention can be used for a variety of purposes. For purposes of illustration, methods of characterizing proteins using the proteins enriched and/or purified by the methods of the invention, are described. Methods of detecting or identifying a protein, genotyping (protein mutation detection), identifying splice variants, determining the presence or absence of a protein of interest, expression profiling, methods for identifying protein degradation products, methods for identifying change in post-translational modification, and methods of protein discovery are also described.

For simplicity and convenience, reference is generally made to "protein(s)." It is understood that reference to protein encompasses "polypeptides" (interchangeably termed "polypeptide fragments"). As is evident from the discussion herein, in some embodiments, a protein cleaving agent is used to generate polypeptide fragments.

In addition to proteins, the methods of the invention may be used to fractionate any chemical moiety of sufficient complexity that it can be recognized by specific binding molecules, such as, for example, antibodies, e.g., lipids, polysaccharides, polynucleotides, metabolic compounds. The methods may also be used to label and/or sort intact cells into different pools using proteins present on the cell surface. In one embodiment, the methods may be used to determine nucleic acid composition in a sample, by fractionating nucleic acids that have been digested with restriction enzymes and tagged with epitope-labeled adapters (for example, 3' overhangs could be tagged with an epitope specific to the particular restriction enzyme used), and binding small epitope antibodies to the tagged nucleic acids. The invention also provides polynucleotides, lipids, polysaccharides, cells, or other moieties characterized, fractionated, or enriched according to the methods of the invention.

Methods Using Protein Binding Molecules

Antibodies have been widely used to provide molecular recognition in a wide range of applications. However, technologies that allow specific detection, fractionation and quantification of molecules continue to evolve. Techniques now allow the generation and production of synthetic and non-native binding molecules including, but not limited to, protein molecules and nucleic acid molecules. For example, the development of aptamers or nucleic acid ligands makes possible the isolation of oligonucleotide sequences with the capacity to recognize virtually any class of target molecule with high affinity and specificity. Aptamers have been shown to recognize epitopes on target molecules, including both conformational and linear/continuous epitopes. (See, e.g. Xu and Ellington (1996) *PNAS* 93:7475-7480; Jayasena (1999) *Clinical Chem.* 45:1628-1650.)

Additional technologies are being developed to generate other binding molecules with high affinity and specificity including, but not limited to, synthetic antibody mimics, affibodies, anticalins, nanobodies and monobodies. Although some methods herein are described using antibodies and/or aptamers, it should be understood that other protein-binding molecules may be used in the methods of the invention.

In some embodiments, the invention provides methods using antibodies that bind (generally, specifically bind) small epitopes, termed "small epitope antibodies," for fractionation of a protein-containing sample or fraction. With respect to all methods described herein, reference to a small epitope antibody also includes compositions comprising one or more of these antibodies. These compositions may further comprise buffers and/or components to enhance stability, which are well known in the art.

In some embodiments, the invention provides methods using aptamers that have been selected to bind (generally, specifically bind) small epitopes for fractionation of a protein-containing sample or fraction. These aptamers will be referred to as "small epitope aptamers". With respect to all methods described herein, reference to a small epitope aptamer also includes compositions comprising one or more of these aptamers. These compositions may further comprise buffers and/or components to enhance stability, which are well known in the art.

"Small epitope antibody" or "small epitope aptamer" as used herein refers to an antibody or aptamer that recognizes an epitope that is present in a multiplicity of proteins (such as an epitope consisting of or consisting essentially of 3 linear amino acids, 4 linear amino acids, or 5 linear amino acids). The term "small epitope binding molecule" includes, but is not limited to, small epitope antibody and small epitope aptamer. Small epitope binding molecules suitable for use in the methods of the invention are extensively described herein and exemplified in the Examples. By virtue of the specificity of the small epitope binding molecules, such as e.g., small epitope antibodies and small epitope aptamers, proteins or peptides (e.g., polypeptides) are separated, enriched and/or purified depending on the presence and/or amount of the small epitope within the protein that is recognized by the small epitope binding molecule(s) used in the methods of the invention.

Small epitope binding molecules bind to protein in a protein mixture based on the presence or absence or amount of small epitopes within proteins within the protein mixture, thereby forming small epitope binding molecule-protein complexes. In some embodiments, proteins are enriched (i.e., fractionated) by virtue of binding to small epitope binding molecules and formation of small epitope binding molecule-protein complexes. A protein mixture may be fractionated with a plurality of small epitope binding molecules, whereby fractions each comprising protein(s) comprising and enriched for small epitope(s) recognized by one or more small epitope binding molecules are generated. As used herein, "enriched" refers to an increase in concentration and/or purity of a protein or peptide in comparison with the concentration and/or purity of the protein or peptide in the sample from which it was derived. Use of the methods of the invention may therefore serve to reduce the complexity of a protein mixture, facilitating subsequent use and/or characterization of the resulting enriched protein components. Insofar as the amino acid sequence or composition of a small epitope bound by a small epitope binding molecule is known, binding by the binding molecule provides information relating to amino acid sequence and/or content of protein(s) bound by the small epitope binding molecule. As described herein, epitope identity information (i.e., the amino acid content and/or sequence recognized by a small epitope binding molecule) may be used in combination with other methods of the invention to characterize, e.g., identify proteins. Small epitope antibodies and small epitope aptamers are further described herein.

In some embodiments, the method comprises: (a) fractionating protein in a protein-containing sample with a first plurality of small epitope binding molecules (i.e., two or more different small epitope binding molecules) to produce fractions; (b) contacting protein in a fraction with a second plurality of small epitope binding molecules (i.e., two or more different small epitope binding molecules); and (c) detecting protein bound to each of the small epitope binding molecules in the second plurality of small epitope binding molecules. The first plurality of first small epitope binding molecules may be the same or different than the second plurality of small epitope binding molecules. Proteins may optionally be separated from the second small epitope binding molecules prior to detection.

In some embodiments, a protein-containing sample is fractionated with any of about 10, 20, 30, 40, 50, 75, 100, 125, 150, 200, 300, 400, 500, 1000, or more small epitope binding molecules. In some embodiments, the sample is fractionated with any of at least about 10, 20, 30, 40, 50, 75, 90, 100, 125, 150, 200, 300, 400, 500, 1000, or more small epitope binding molecules. In some embodiments, the sample is fractionated with at any of least about 10, 20, 30, 40, 50, 75, 90, 100, 125, 150, 200, 300, 400 or 500 small epitope binding molecules, with an upper limit of any of about 20, 30, 40, 50, 75, 100, 125, 150, 200, 300, 400, 500, or 1000 small epitope binding molecules.

In some embodiments, a first plurality of about 100 small epitope binding molecules is used to produce a set of about 100 first fractions and one or more first fraction(s) is contacted with a second plurality of about 100 small epitope binding molecules to produce about 100 second fractions from each first fraction. The first plurality of small epitope binding molecules and the second plurality of small epitope binding molecules may be the same or different.

In methods in which small epitope binding molecules are used for fractionation, proteins comprising one or more epitope(s) bound by a small epitope binding molecule are isolated, separated, enriched and/or purified (i.e., removed from the environment of the original sample or a fraction produced from the original sample). In some embodiments, the methods further comprise separating protein from a binding molecule-protein complex in the first and/or second set of fractions.

In some embodiments, the method comprises: (a) contacting protein in a protein-containing sample with a plurality of small epitope binding molecules; (b) fractionating protein from the small epitope binding molecule-protein complexes into fractions; and (c) detecting protein in each fraction. Generally, proteins comprising one or more epitope(s) bound by a small epitope binding molecule are isolated, separated, enriched and/or purified (i.e., removed from the environment of the original sample). In some embodiments, the methods further comprise separating protein from the binding molecule-protein complexes prior to further fractionation and/or prior to detection.

Methods and conditions for antibody binding and separation of antibody-protein complexes are well known in the art and further described herein. Methods and conditions for aptamer binding and separation of aptamer-protein complexes are known in the art and further described herein. In some embodiments, protein in a sample or fraction is partially or wholly denatured when it is contacted with the small epitope binding molecules, but denaturation is not required in every embodiment.

In some embodiments, contacting a sample or fraction with two or more small epitope binding molecules is sequential (as when one binding molecule is contacted with the sample, then removed, another binding molecule is contacted with the sample and removed, and so on). In other embodiments, contacting a sample or fraction with two or more small epitope binding molecules is in parallel, for example, as when a group of binding molecules are contacted with the sample simultaneously. In some embodiments, several groups of two or more binding molecules are serially contacted with the sample or fraction, for example, group 1 is contacted and removed, group 2 is contacted and removed, and so on.

In some embodiments, the methods further comprise treating the sample with a protein cleaving agent to form polypeptide fragments. In one embodiment, the protein cleaving agent is added prior to contacting protein in a protein-containing sample with a plurality of small epitope binding molecules. In another embodiment, the protein cleaving agent is added prior to fractionating protein from the small epitope binding molecule-protein complexes into fractions. In another embodiment, the protein cleaving agent is added prior to detection of protein in each fraction. In one embodiment, protein is separated from small epitope binding molecule-protein complexes prior to treatment with a protein cleaving agent and the resulting polypeptide fragments are fractionated and detected. In one embodiment, fractionation of protein in the small epitope binding molecule-protein complexes into fractions comprises treatment with a protein cleaving agent, and the resulting polypeptide fragments are separated by size or physical properties to form fractions, and protein in each fraction is detected.

In some embodiments, a sample or fraction is contacted with small epitope binding molecules immobilized on a solid matrix, for example, on pins, on beads, or in an array on a solid substrate.

In some methods of the invention, at least two fractionations of protein in a sample are performed, wherein one or both of the at least two fractionations comprise use of small epitope antibodies. More than two fractionations can be performed, e.g., at least 3, 4, or 5 fractionations, with at least one of the fractionations comprising the use of small epitope antibodies.

In some methods of the invention, at least one fractionation comprises the use of small epitope antibodies, and one or more additional fractionations comprise the use of small epitope antibodies or another fractionation condition, such as, for example, use of other protein-binding molecules that bind to a specific protein or class of proteins, such as, for example, aptamers, antibodies, molecular imprints, lectins, or capture compounds (e.g., described in U.S. Application No. 2004/0209255), chromatography, (e.g., HPLC), or electrophoresis, (e.g., capillary electrophoresis).

In some methods of the invention, at least one fractionation comprises the use of small epitope aptamers, and one or more additional fractionations comprise the use of small epitope aptamers or another fractionation condition, such as, for example, use of other protein-binding molecules that bind to a specific protein or class of proteins, such as, for example, antibodies, molecular imprints, lectins, or capture compounds, chromatography, (e.g., HPLC), or electrophoresis, (e.g., capillary electrophoresis).

It is understood that a sample or fraction may be contacted with other protein-binding molecules in conjunction with small epitope antibodies, including antibodies that are not small epitope antibodies, and other protein-binding molecules. Such protein-binding molecules may be used simultaneously, sequentially, before or after treatment with small epitope antibodies.

Fractionation

Methods of the invention include fractionation of a protein-containing sample in at least two "dimensions," i.e., a first fractionation of a protein-containing sample into a plurality of first fractions, and fractionation of at least one first fraction into a plurality of second fractions. Generally, the protein-containing sample is fractionated into any of at least about 10, 20, 30, 40, 50, 60, 70, 80, 90, 100, 200, 300, 400, 500, 600, 700, 800, 900, or 1000 fractions, and a first fraction is fractionated into any of at least about 10, 20, 30, 40, 50, 60, 70, 80, 90, 100, 200, 300, 400, 500, 600, 700, 800, 900, or 1000 second fractions. In one embodiments, the method comprises fractionating a protein-containing sample into about 100 first fractions, and fractionating each of the first fractions into about 100 second fractions.

Fractionation may comprise physical separation of a sample or fraction into a plurality of portions each of which is contacted with one or more protein-binding molecules. For example, a sample or fraction may be divided into separate wells of a microtiter plate, and contacted with one or more protein-binding molecules per well. Alternatively, fractionation may comprise contacting of an entire sample or fraction with a plurality of protein-binding molecules that are physically separated, for example, in different areas of a support in an array, on pins, or on beads.

At least one fractionation is achieved by using a plurality of protein-binding molecules each with a different specificity. For example, a plurality of small epitope antibodies may be used, each of which recognizes a different small epitope. Or a plurality of small epitope aptamers may be used, each of which has been designed and selected to recognize a different small epitope. Other protein-binding molecules which may be used in accordance with the methods of the invention include aptamers, antibodies, lectins, molecular imprints, or capture compounds (e.g., as described in U.S. Patent Application No. 2004/0209255), each of which recognizes a specific protein or class of proteins. Other examples of protein-binding molecules include proteins comprising immunoglobulin superfamily domains (see, for example, Halaby et al. (1999) *Protein Engineering* 12(7):563-571; Barclay (2003) *Seminars in Immunology* 15:215-223). Some binding molecules are constructed from a member of the immunoglobulin superfamily wherein the native CDR loops are replaced with protein sequences from antibodies. Other binding molecules are based upon small protein scaffolds, such as the IgG binding domain of Protein A (see e.g. Affibodies®, www.affibody.com). Other binding molecules include molecularly engineered antibody or antibody-like molecules which have been reduced to their smallest structural unit (see e.g., www.domantis.com), and naturally small antibodies from other species such as nanobodies from camels or llamas, which may or may not be molecularly manipulated, (see e.g., www.ablynx.com). Other examples of protein-binding molecules are anticalins, for example, based on lipocalins, such as retinol binding protein. Anticalins have binding pockets with a smaller surface area than antibodies. (See, for example, Weiss and Lowman (2000) *Chemistry & Biology* 7:R177—R184; Skerra (2000) *Biochim et Biophys Acta* 1842:337-350; Schlehuber and Skerra (2005) *Drug Discovery Today* 10(1):23-33; Beste et al. (1999) *Proc Natl Acad Sci* 96:1898-1903.) Further examples of protein-binding molecules include synthetic scaffolds. (See, for example, Shin (2004) *Pure Appl. Chem.* 76(7-8): 1579-1590; Forrer et al. (2004) *ChemBioChem* 5:183-189; Nygren and Skerra (2004) *J. Immunological Methods* 290:3-28).

In some embodiments, protein-binding molecules are used in two "dimensions," i.e., a plurality of protein-binding molecules is used for fractionation of a protein-containing sample into first fractions and at least one first fraction is further fractionated into second fractions with a plurality of protein-binding molecules which may be the same or different than the protein-binding molecules that were used for the first fractionation.

In some embodiments, protein-binding molecules are used in one dimension, and fractionation in another dimension is achieved based on chemical or physical properties of the proteins in a sample or fraction. For example, proteins in a sample may be fractionated into first fractions with protein-binding molecules, and one or more first fractions may be further fractionated into second fractions based on chemical or physical properties, for example with a technique such as chromatography (e.g., HPLC), electrophoresis (e.g., capillary electrophoresis, isoelectric focusing, isotachophoresis), general binding characteristics (e.g., hydrophobic surface adsorption), differential precipitation, or molecular weight separation (e.g., gel filtration, dialysis). Alternatively, proteins in a sample may be fractionated into first fractions based on chemical or physical properties as described above, and one or more first fraction may be further fractionated into second fractions with protein-binding molecules.

In some embodiments, at least one fractionation is effected with protein-binding molecules immobilized on a solid matrix. For example, each of a plurality of different protein-binding molecules may be immobilized at different sites on a solid matrix as an array, with fractionation achieved by contacting a protein-containing sample or fraction with the array. After binding of proteins in the sample of fraction to protein-binding molecules in the array, the proteins that have bound to one or more protein-binding molecule may be eluted for further fractionation and detection. In one embodiment, proteins are eluted into the wells of a microtiter plate, for example, a 96-well or 384-well plate for further fractionation.

In some embodiments, protein-binding molecules are immobilized on a solid matrix in the form of pins, each of which contains at least one (i.e., one or a multiplicity) immobilized protein-binding molecule(s), and fractionation is achieved by contacting a protein-containing sample or fraction with the pins and allowing proteins in the sample or fraction to bind to the protein-binding molecules on the pins.

In some embodiments, protein-binding molecules are immobilized on beads, each of which contains at least one (i.e., one or a multiplicity) immobilized protein-binding molecule(s), and fractionation is achieved by contacting a protein-containing sample or fraction with the beads and allowing proteins in the sample or fraction to bind to the protein-binding molecules on the beads. In one embodiment, the beads are different sizes and the method comprises separation of the beads based on size (e.g., via flow cytometry) after binding of proteins in the sample or fraction to the protein-binding molecules on the beads. If the proteins and/or protein-binding molecules are labeled, detection of proteins bound to the beads may be achieved simultaneously with size separation of the beads, or proteins may be eluted from the beads after size separation of the beads and then detected.

Detection

Methods of the invention comprise detection of proteins fractionated as described herein. Detection may be direct, i.e., via a detectable label attached to the protein, or indirect, i.e., via detection of a molecule bound to or associated with a molecule or moiety attached to the protein. In some embodiments, a label attached to a fractionated protein is detected. In some embodiments, a label attached to a protein-binding molecule bound to a protein is detected. In some embodiments, both a label attached to a fractionated protein and a label attached to a protein-binding molecule bound to a protein are detected.

In methods of the invention, detection of fractionated proteins comprises detection of labeled protein-binding molecules, labeled proteins, or both labeled protein-binding molecules and labeled proteins.

In some embodiments, proteins are labeled, and the method comprises detection of labeled proteins. Proteins may be labeled prior to, during, or after fractionation.

"Label" as used herein refers to a composition capable of producing a detectable signal. A label is any composition detectable by spectroscopic, photochemical, biochemical, immunochemical, electrical, optical, chemical, or any other means by which the label may be detected quantitatively and/or qualitatively. The term "label" refers to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. A label may be attached via a linker. Examples of labels include, but are not limited to, biotin, avidin, streptavidin, digoxigenin, fluorophors (e.g., fluoroescein, acetylaminofluorene), chromophors, magnetically responsive compounds, antibody epitope-containing compounds, haptens, radiolabels (e.g., $^{125}$I, $^{32}$P, $^{33}$P, $^{3}$H, $^{14}$C, $^{35}$S), detectable isotopes (e.g., $^{2}$H), chemiluminescent labels, bioluminescent labels, enzymes, or magnetic labels such as magnetic beads.

The label may also be a compound that is a member of a binding pair, one member of which bears a detectable moiety or physical property. The terms "binding partner," "member of a binding pair," or "cognate ligand" refer to molecules that specifically bind other molecules to form a binding complex, such as, for example, antibody/antigen, lectin/carbohydrate, nucleic acid/nucleic acid, receptor/receptor ligand, avidin/biotin or streptavidin, etc. The label may also be a moiety that is suitable for detection by mass spectrometry.

A label may be a member of a signal producing system that acts in concert with one or more additional members of the same system to provide a detectable signal. Illustrative of such labels are members of a specific binding pair, such as a ligand, e.g., biotin, fluorescein, digoxigenin, antigen, polyvalent cation, or a chelator group, where the member specifically binds to one or more additional members of the signal producing system, wherein the additional member(s) provide a detectable signal either directly or indirectly, e.g., antibody conjugated to a fluorescent moiety or an enzymatic moiety capable of converting a substrate to a chromogenic product, e.g., alkaline phosphatase conjugated antibody. The label is subsequently detected by colorimetry or chemiluminescence, for example as described by Coutlee, et al. (1989) *J. Clin. Microbiol.* 27:1002-1007. In one embodiment, bound alkaline phosphatase is detected by chemiluminescence with a reagent such as a Lumi-Phos™ luminometer (source Scientific Systems, Inc., Garden Grove, Calif.).

Fluorescent labels include coumarin and its derivatives (e.g., 7-amino-4-methylcoumarin, aminocoumarin), BODIPY dyes (e.g., BODIPY FL, cascade blue), fluorescein and its derivatives (e.g., fluorescein isothiocyanate, Oregon green), rhodamine dyes (e.g., Texas red, tetramethylrhodamine, eosins and erythrosins), cyanine dyes (e.g., Cy3 and C65), macrocyclic chelates of lanthanide ions (e.g., QUANTUM DYE™), and fluorescent energy transfer dyes (e.g., thiazole orange-ethidium heterodimer, TOTAB, etc.).

Proteins may be labeled by incorporating a label at the C-terminus, N-terminus, and/or at one or more interior amino acid residues (i.e., amino acid residues that comprise a reactive nucleophilic moiety, for example, Lys, Arg, Cys). In some embodiments, proteins are differentially labeled with different labels at different positions in the polypeptide. In some embodiments, proteins are labeled and then cleaved, chemically or enzymatically, to produce polypeptide fragments, and only the labeled fragments are detected, thereby simplifying analysis. Incorporation of a label may also be used to separate labeled fragments from non-labeled fragments. For example, the N-termini of proteins could be labeled with biotin and then separated from non-labeled fragments after chemical or enzymatic cleavage of the polypeptides by binding to a reagent containing avidin or streptavidin, thus producing a protein mixture essentially containing only N-terminal fragments.

In some embodiments, protein-binding molecules, e.g., protein-binding molecules used for fractionation of a sample or fraction, are labeled, and the method comprises detection of the labels attached to the protein-binding molecules. In some embodiments, the protein-binding molecules each comprise a "unique detectable label," each of which is uniquely coded such that it may be distinguished from other unique detectable labels attached to other protein-binding molecules. Examples of unique detectable labels for use in accordance with the methods of the invention include, but are not limited to, color-coded microspheres of known fluorescent light intensities (see e.g., microspheres produced by Luminex, www.luminexcorp.com); microspheres containing quantum dot nanocrystals, for example, containing different ratios and combinations of quantum dot colors (see e.g., Qdot® nanocrystals, www.probes.invitrogen.com); glass coated metal nanoparticles (see e.g., SERS nanotags produced by Nanoplex Technologies, Inc., www.nanoplextech.com); barcode materials (see e.g., sub-micron sized striped metallic rods such as Nanobarcodes® Particles produced by Nanoplex Technologies, Inc.), encoded microparticles with colored bar codes (see e.g., CellCard™ produced by Vitra Bioscience, www.vitrabio.com), glass microparticles with digital holographic code images (see e.g., CyVera microbeads produced by Illumina, www.illumina.com); chemiluminescent dyes, combinations of dye compounds; and beads of detectably different sizes.

In one embodiment, a plurality of small epitope binding molecules (i.e., two or more different small epitope binding molecules) is used for fractionation, wherein each of the different small epitope binding molecules comprises a unique detectable label, and the method comprises detection of the unique detectable labels in small epitope binding molecule-protein complexes. Fractionated protein may be detected by detection of labels attached to the small epitope binding molecules. Labeled binding molecules may be detected in small epitope binding molecule-protein complexes, or after separation of proteins from the complexes. Proteins will have unique "signatures" based on a unique pattern of binding of one or a plurality of small epitope binding molecules to a particular protein, dependent upon the epitopes within the protein that are recognized by small epitope binding molecules used in the fractionation method. Detection may be based on an assessment of the combination of labeled binding molecules bound to each protein in a fraction.

Protein Cleaving Agents

In some embodiments, the methods comprise treating proteins with a protein cleaving agent, whereby polypeptide fragments are generated. The protein cleaving agent may be an enzyme (such as chymotrypsin or trypsin) or a chemical agent (such as cyanogen bromide). Protein cleaving agents that cleave at specific amino acid sequences are useful, (for example, trypsi cleaves at Arg and Lys residues, or V8 protease cleaves at Glu residues). Digestion with a protein cleaving agent that cleaves at specific amino acid residues produces protein fragments with a constant or constrained C-terminal amino acid residue (with the possible exception of the true C-termini of the original proteins in the sample). A constrained C-terminal amino acid residue decreases the number of small epitopes available for detection by protein-binding molecules and may be used as a means to simplify analysis.

Treatment with a protein cleaving agent may be performed on protein in a protein-containing sample prior to fractionation, protein in a fraction after fractionation, protein in a protein-binding molecule-protein complex, or protein separated from a protein-binding molecule-protein complex, to generate polypeptide fragments, which may be detected in a method for characterizing proteins in a sample as described herein. Protein cleaving agents and methods for treatment with protein cleaving agents are well known in the art and further described herein. As described above, proteins may optionally be labeled prior to cleavage with a protein cleaving agent, and detection may comprise detecting labeled polypeptide fragments.

In one embodiment, the invention provides methods for characterizing protein in a protein-containing sample, comprising fractionating protein in the sample into fractions (e.g., with a plurality of protein-binding molecules, such as small epitope antibodies or small epitope aptamers), contacting protein in one or more fractions with a plurality of protein-binding molecules, such as small epitope antibodies or small epitope aptamers, thereby forming protein-binding molecule-protein complexes (for example, small epitope antibody-protein complexes or small epitope aptamer-protein complexes), separating protein from the complexes, treating the protein with a protein cleaving agent, whereby polypeptide fragments are generated, and detecting polypeptide fragments generated from proteins in the protein-containing sample.

In another embodiment, the invention provides methods for characterizing protein in a protein-containing sample, comprising fractionating protein in the sample into fractions (e.g., with a plurality of protein-binding molecules, such as small epitope antibodies or small epitope aptamers), contacting protein in one or more fractions with a plurality of protein-binding molecules, such as small epitope antibodies or small epitope aptamers, thereby forming binding molecule-protein complexes (for example, small epitope antibody-protein complexes or small epitope aptamer-protein complexes), treating the complexes with a protein cleaving agent to produce polypeptide fragments, and detecting polypeptide fragments generated from proteins in the protein-containing sample.

In another embodiment, the invention provides methods for characterizing protein in a protein-containing sample, comprising treating protein in the sample with a protein cleaving agent to produce polypeptide fragments, fractionating the polypeptide fragments into fractions, further fractionating polypeptide fragments in one or more of the fractions, and detecting fractionated polypeptide fragments. Generally, one or both of the fractionations is performed by binding to a plurality of protein-binding molecules, such as small epitope antibodies or small epitope aptamers.

In another embodiment, the invention provides methods for characterizing protein in a protein-containing sample, comprising fractionating protein in the sample into fractions, treating protein in the fractions with a protein cleaving agent to produce polypeptide fragments, further fractionating the polypeptide fragments from one or more fraction, and detecting fractionated polypeptide fragments. Generally, one or both of the fractionations is performed by binding to a plurality of protein-binding molecules, such as small epitope antibodies or small epitope aptamers.

In another embodiment, the invention provides methods for characterizing protein in a protein-containing sample, comprising treating protein in the sample with a protein cleaving agent to produce polypeptide fragments, fractionating the polypeptide fragments with small epitope binding molecules into fractions, and detecting unbound polypeptide fragments. In some embodiments, the fractionation comprises at least one fractionation comprising binding molecules that recognize C-terminal small epitopes. In some embodiments, the fractionation comprises at least one fractionation comprising binding molecules that recognize internal small epitopes.

In another embodiment, the methods for characterizing protein in a protein-containing sample comprising treating protein in the sample with a protein cleaving agent to produce polypeptide fragments, fractionating the polypeptide fragments with a first set of small epitope binding molecules which bind to C-terminal epitopes, further fractionating one or more of the fractions with a second set of small epitope binding molecules which bind to internal epitopes.

Pretreatment of Protein Containing Sample

In some embodiments, the sample is treated with one or more agents, such as antibodies, that bind to one or more proteins, preferably proteins that are known to be abundant in the sample, prior to the first and/or second fractionation in accordance with the methods described herein.

For example, in a serum sample, pretreatment may comprise antibodies that bind to albumin, immunoglobulin, and/or other abundant proteins. In one embodiment, proteins in the sample are cleaved with a protein cleaving agent prior to contact with the one or more antibodies that bind to one or more known abundant proteins. In another embodiment, proteins in the sample are cleaved with a protein cleaving agent after contact with the one or more antibodies that bind to one or more known proteins, such as abundant proteins. In one embodiment, the bound protein(s) (such as abundant protein(s)) are removed from the sample prior to fractionation, e.g., prior to contact with a plurality of protein-binding molecules.

In one embodiment, the method comprises "debulking" of a sample prior to fractionation by treatment with one or more antibodies that bind to one or more known proteins in the sample, such as abundant protein(s) (optionally followed by removal of bound proteins), cleavage of proteins in the sample with a protein cleaving agent, and contact of cleaved proteins with a plurality of protein-binding molecules, such as small epitope antibodies or small epitope aptamers. In another embodiment, the method comprises treatment of the sample with a protein cleaving agent, debulking of the sample by treatment with one or more antibodies that bind to one or more known proteins, such as abundant protein(s) and/or cleaved polypeptide fragments in the sample (optionally followed by removal of the bound protein(s) and/or polypeptide fragments), and contact of the remaining proteins and/or cleaved polypeptide fragments with a plurality of protein-binding molecules, such as small epitope antibodies or small epitope aptamers. In another embodiment, the method comprises debulking of the sample by treatment with one or more antibodies that bind to one or more known proteins, such as abundant protein(s) (optionally followed by removal of the bound protein(s)), contacting the sample with a plurality of protein-binding molecules, such as small epitope antibodies or small epitope aptamers, to form protein-binding molecule-protein complexes (e.g., small epitope antibody-protein complexes or small epitope aptamer-protein complexes), and treatment of the complexes with a protein cleaving agent.

In one embodiment, the method comprises debulking of the sample with one or more antibodies that bind to one or more known proteins in the sample, such as abundant protein(s), followed by multiplex fractionation of debulked proteins (e.g., abundant proteins or proteins bound to or associated with abundant proteins), or fragments thereof (e.g., produced by proteolytic digestion or chemical cleavage), in accordance with the methods as described herein.

In another embodiment, the method comprises treatment of the sample with a protein cleaving agent to produce polypeptide fragments, debulking of the sample by treatment with a plurality of protein-binding molecules that recognize at least one C-terminal small epitope at the end of the polypeptide fragments. After removal of the protein-binding molecule-polypeptide fragment complexes characterization of the protein sample is simplified by analysis of the remaining unbound, true C-terminal fragments.

Methods of Characterizing a Protein

The invention provides methods for characterizing (for example, identifying, detecting (presence or absence) and/or quantifying) a protein or polypeptide fragment of interest. Methods of the invention generate fractions of the sample which comprise fewer proteins than in the starting sample, facilitating subsequent characterization of the protein comprised in a fraction. Methods for identifying, detecting, and quantifying proteins are well known in the art. In some embodiments, proteins are detectably labeled, and detection of proteins comprises detection of the detectable label. In one embodiment, the label comprises biotin and detection comprises binding of a fluorescent streptavidin label, and detection of fluorescence. Quantification may comprise assessment of the amount of label detected (e.g., strength of signal) with respect to one or more proteins in a fraction. Identification of one or more proteins may comprise comparison of one or more characteristics of a protein in a fraction (e.g., size, chemical, or physical characteristics, or binding to a combination of small epitope antibodies that each recognizes a known small epitope) with characteristics of a known protein.

Thus, the invention provides methods for characterizing a protein comprising fractionating proteins in a protein-containing sample and analyzing the proteins (interchangeably termed "products") which are fractionated by any of the methods described herein.

In one aspect, the invention provides methods for characterizing a protein comprising: analyzing proteins (interchangeably termed "products"), wherein the protein is prepared using any of the methods for fractionating proteins in a sample described herein (including: methods for purifying and/or enriching a protein, methods for isolating a protein, methods for separating a protein, methods for preparing a protein fraction for characterization, methods for preparing a protein fraction for mass spectrometry analysis, methods for identifying a protein (such as one or more protein, or a group of proteins), methods for discovering a new protein, methods for quantification of protein in a sample, methods for determining presence or absence of a protein in a sample, and methods for expression profiling).

Analyzing proteins can be performed by any method known in the art or described herein. Methods for analyzing proteins are well known in the art, and include: sodium dodecyl sulphate-polyacrylamide gel electrophoresis ("SDS-PAGE"), isoelectric focusing, high pressure liquid chromatography ("HPLC"), FPLC, thin layer chromatography, affinity chromatography, gel-filtration chromatography, ion exchange chromatography, and other standard biochemical analyses, immunodetection, protein sequencing, analysis with protein arrays, mass spectrometry (including MS/MS, IMS/MS, LC/MS and GC/MS), and the like. Thus, the invention includes those further analytical and/or quantification methods as applied to any of the products of the methods herein.

Proteins may be analyzed or detected by detection of a detectable label attached to a protein-binding molecule, such as a small epitope antibody or small epitope aptamer, which binds proteins in a sample or fraction and/or a detectable label attached to proteins or polypeptide fragments in a sample or fraction. Detection of a label may be direct or indirect. As used herein, "direct" detection refers to detection of a label that is covalently attached to a protein being analyzed (e.g., detection of a fluorescent label that is covalently attached to a protein), and "indirect" refers to detection of a label via non-covalent association of a molecule or moiety with a label that is attached to a protein being analyzed (e.g., detection of streptavidin binding to a biotin label covalently attached to a protein). In some embodiments, fractionated proteins comprise a detectable label, such as, for example, biotin, avidin, streptavidin, fluorophors, an enzymatic label, or a radiolabel, and protein-binding molecules bound to the fractionated proteins each comprise a unique detectable label, examples of which are described above, and analyzing proteins comprises detection of both the label attached to the proteins and the unique detectable labels attached to the protein-binding molecules.

In some embodiments, the step of analyzing comprises determining amount of said proteins, whereby the amount of protein(s) prepared, enriched and/or separated is quantified. It is understood that the amount of enriched protein(s) may be determined using quantitative and/or qualitative methods. Determining amount of protein product includes determining whether product is present or absent.

In some embodiments, the step of analyzing comprises identifying one or more proteins or polypeptide fragments. Methods for identifying a protein are known in the art, and include: immunodetection, protein sequencing, and the like. In some embodiments, essentially all of the enriched proteins (purified or enriched from a sample) are identified. In some embodiments in which small epitope antibodies or small epitope aptamers are used for fractionation, the identity of the epitope(s) to which the small epitope antibody(ies) or small epitope aptamer(s) bind is used to assist identification of the enriched proteins. In some embodiments, a protein is identified using any one or more of the following characteristics: sequence; mass; m/z ratio (in embodiments involving mass spectrometric analysis), amino acid composition, and any other method that provides sufficient information to identify a protein. As used herein, "identify" includes identifying known (previously characterized proteins) as well as discovery of previously unknown or uncharacterized proteins (including protein variants such as mutant proteins, differentially modified proteins (e.g., varying carbohydrate content) and splice variants). In some embodiments, a multiplicity, a large multiplicity or a very large multiplicity of proteins are identified. In other embodiments, any of at least about 2, 3, 4, 5, 10, 20, 30, 40, 50, 60, 70, 80, 90, 100, 500, or 1000 or more proteins are identified.

In some embodiments, the step of analyzing includes analysis for the detection of any alterations in the protein, as compared to a reference protein which is identical (at least in part) to the protein sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants, and/or post-translational modifications, such as variation in amount of glycosylation, and protein degradation or by-products. Sequence alterations include mutations (such as deletion, substitution, insertion and/or transversion of one or more amino acid).

Expression Profiling

The methods of the invention are suitable for use in determining the expression level of one or more proteins in a sample. As described above, fractionated proteins can be detected and/or quantified by various methods, as described herein and/or known in the art. It is understood that amount of protein product may be determined using quantitative and/or qualitative methods. Determining amount of product includes determining whether product is present or absent. Thus, an expression profile can include information about presence or absence of one or more proteins or protein sequences of interest. "Absent" or "absence" of product, and "lack of detection of product" as used herein includes insignificant, or de minimus levels.

In some embodiments, the amounts of proteins in two or more samples are compared. Typically, the samples have overlapping protein profiles. Using the methods of the present invention, the amounts of the proteins can be compared to determine how the profiles differ in the nature and amount of proteins that are present. These methods are useful for identifying a change in the nature or amount of a protein that is indicative of a disease state (e.g., a disease biomarker, PSA, BRCA1, etc.) or treatment efficacy, toxic effects of an agent, or presence of a pathogen (e.g., HIV, bacterial pathogens, viral pathogens, prions, etc), etc. These methods are also useful for discovering proteins that are associated with disease states for drug discovery purposes, diagnostic purposes, etc. In particular, it is useful to compare the protein profiles of samples that are from different subjects or have been subjected to different conditions or treatments.

For example, in certain embodiments, the first sample is an untreated control sample and the second sample has been subjected to an agent or condition. Examples of agents include, but are not limited to: a chemotherapeutic agent, ultraviolet light, a medical device (e.g., a stent defibrillator), an exogenous gene, and a growth factor. Those of skill in the art will recognize that there are many ways to introduce an exogenous gene into a cell (see, e.g., Ausubel et al., eds., (1994), supra). In other embodiments, the first sample is a diseased sample and the second sample is a non-diseased sample. In addition, agents can take the form of candidate drugs. For example, the proteins in a first sample treated with a candidate drug can be compared to a second sample which is a negative or positive control. The influence of the candidate drug on the amount of a protein present in the first sample as compared to the second sample can be an indication of the candidate drug's efficacy or toxicity. Those of skill in the art will appreciate that these methods can be adapted to analyze the effects of any agent on a disease state or amount of a disease marker present in a sample. In one embodiment, the methods are used to identify protein(s) that are associated with treatment with an agent (such as a candidate drug). Such proteins may be associated with efficacy of the agent, and thereby serve as a proxy for a clinical endpoint.

Biomarkers

Biomarker protein(s) can be identified using the fractionation methods described herein for expression profiling and characterization of proteins in a sample. A biomarker is a protein of interest, for which the detection, monitoring, quantitation, and/or characterization is of interest. In some embodiments, a biomarker is correlated with a specific condition or treatment, such as a disease or condition, treatment with a drug (including efficacy of drug treatment and/or toxicity), treatment with a medical device, and the like. In other embodiments, a biomarker is expressed in a tissue or cell of interest (e.g., a tumor, an organ, etc.). As used herein, a biomarker protein may be a newly identified protein or protein variant (such as a mutant protein, splice variant, a protein with altered post-translational modification, etc.). In other embodiments, a biomarker is a tissue-specific marker.

A biomarker can be used as a surrogate marker in diagnosis (including staging of disease, in some embodiments), prognosis, evaluation and/or selection of therapies, monitoring of disease progression, monitoring of efficacy of treatment, and/or treatment of disease. In some embodiments, a biomarker is detected and/or quantified by any method known in the art, and/or any method described herein, whereby expression of the biomarker (presence or absence of biomarker, or differential expression of the biomarker) indicates the presence of a disorder or a condition. In one embodiment, increase in level of a biomarker indicates the presence of a disorder or condition. In another embodiment, decrease in level of a biomarker indicates the presence of a disorder or condition. In some embodiments, biomarker expression is used to evaluate the efficacy of a particular therapeutic treatment regimen in animal studies, in clinical trials, or to monitor the treatment of an individual subject. In some embodiments, the biomarker serves as a proxy for a desired clinical endpoint. In other embodiments, the biomarker is correlated with efficacy of an agent, as when biomarker expression is predictive of efficacy of treatment with an agent (such as a drug). In one embodiment, increase in level of a biomarker indicates efficacy or progress of treatment. In another embodiment, decrease in level of a biomarker indicates efficacy or progress of treatment.

The biomarker can be used as a marker for toxicity, including, toxicity of an agent such as a pharmaceutical, new drug candidate, cosmetic, or other chemical. In some embodiments, detection of biomarker expression may also be used to monitor for environmental exposure to an agent, such as a toxin or a pathogen. In one embodiment, increase in level of a biomarker indicates toxicity or exposure to an agent. In another embodiment, decrease in level of a biomarker indicates toxicity or exposure to an agent.

A biomarker can be used to screen a plurality or library of molecules and compounds for specific binding affinity, including, for example, DNA molecules, RNA molecules, peptide nucleic acids, polypeptides, mimetics, small molecules, and the like. In one embodiment, an assay involves providing a plurality of molecules and/or compounds, combining a biomarker with the plurality of molecules and/or compounds under conditions to allow specific binding, and detecting specific binding to identify at least one molecule or compound which specifically binds the biomarker.

Similarly, one or more biomarkers, or portions thereof, can be used to screen a plurality or library of molecules and/or compounds in any of a variety of screening assays to identify a ligand. Methods for screening are well known in the art. The assay can be used to screen, for example, aptamers, DNA molecules, RNA molecules, peptide nucleic acids, polypeptides, mimetics, proteins, antibodies, agonists, antagonists, immunoglobulins, inhibitors, small molecules, pharmaceutical agents or drug compounds and the like, which specifically bind the biomarker.

In another embodiment, one or more antibodies comprising an antigen binding site that specifically binds a biomarker can be used for the detection of the biomarker (including in vitro and in vivo detection). In another example, an antibody that specifically binds a biomarker can be linked to an in vivo imaging reagent, such as, for example, $^3$H, $^{111}$In, $^{125}$I, (see Esteban et al. (1987) *J. Nucl. Med.* 28.861-870), and used in an in vivo imaging application.

Compositions and Kits

The invention provides compositions for use in fractionation of proteins in a protein containing sample, as described herein, for applications such as methods for characterizing protein in a sample, methods for reducing the complexity of a sample, methods for purifying and/or enriching a protein or a plurality of proteins, methods for isolating and/or separating a protein or a plurality of proteins, and/or methods for preparing a protein, a plurality of proteins, or a protein fraction for characterization, methods for preparing a protein, a plurality of proteins, or a protein fraction for mass spectrometry analysis, methods for identifying a protein or a plurality of proteins, methods for discovering one or more new proteins, methods for detection and/or quantification of a protein or a plurality of proteins in a sample, methods for characterizing a one or more proteins, methods for expression profiling, methods for identifying protein degradation products, methods for identifying change(s) in post-translational modification, and/or methods for determining the mass, the amount and/or identity of protein(s) in a sample.

Compositions for use in the methods of the invention may comprise protein-binding molecules, such as small epitope antibodies or small epitope aptamers. In some embodiments, compositions are provided comprising one or more protein-binding molecules, wherein each different protein-binding molecule comprises a unique detectable label.

The invention also provides protein "products" enriched, purified, isolated, prepared, separated, and/or fractionated using any of the methods of the invention described herein. The invention also provides proteins or protein fragments characterized (e.g., detected, identified, quantified, etc.) using any of the methods of the invention described herein and compositions comprising such products. In embodiments in which small epitope antibodies or small epitope aptamers are used for fractionation, such proteins comprise a cognate small epitope that is recognized by the small epitope antibody or small epitope aptamer (to which the protein was bound). The invention also provides protein-binding molecule-protein complexes, e.g., small epitope antibody-protein complexes and small epitope aptamer-protein complexes, or protein-binding molecule-protein fragment complexes, e.g., small epitope antibody-protein fragment complexes and small epitope antibody-protein fragment complexes (for methods wherein the proteins are contacted with a protein cleaving agent prior to contact with protein-binding molecules), prepared or isolated by any of the methods described herein. In some embodiments, the invention provides a plurality of protein-binding molecule-protein complexes, e.g., small epitope antibody-protein complexes or small epitope aptamer-protein complexes, prepared according to the methods of the invention, wherein each protein-binding molecule comprises a unique detectable label. The invention also provides proteins or protein fragments separated from a protein-binding molecule-protein complex, e.g., a small epitope antibody-protein complex or a small epitope aptamer-protein complex, or protein-binding molecule-protein fragment complex, e.g., a small epitope antibody-protein fragment complex or a small epitope aptamer-protein fragment complex, according to any of the methods described herein, and/or protein fragments prepared from proteins after separation from protein-binding molecules, such as small epitope antibody(ies).

In another aspect, the invention includes compositions and/or kits comprising intermediates (such as complexes, e.g., small epitope antibody-protein complex or small epitope aptamer-protein complex) produced by any aspect of the methods of the invention. The invention also provides incubation mixtures comprising protein-containing samples and protein-binding molecules, e.g., small epitope antibodies, small epitope aptamers, and/or protein-binding molecule-protein complexes, e.g., small epitope antibody-protein complexes or small epitope aptamer-protein-complexes as described herein.

The invention also provides kits for use in the instant methods. Kits of the invention may include one or more containers each comprising one or more protein-binding molecules, such as small epitope antibody(ies) or small epitope aptamer(s). A kit may comprise any of about 10, 20, 30, 40, 50, 75, 100, 125, 150, 200, 300, 400, 500, 1000, or more protein-binding molecules, such as small epitope antibodies or small epitope aptamers. In some embodiments, a kit comprises a plurality of protein-binding molecules containing any of at least about 10, 20, 30, 40, 50, 75, 90, 100, 125, 150, 200, 300, 400, 500, 1000, or more protein-binding molecules, such as small epitope antibodies or small epitope aptamers. In some embodiments, a kit comprises a plurality of protein-binding molecules containing any of at least about 10, 20, 30, 40, 50, 75, 90, 100, 125, 150, 200, 300, 400 or 500, with an upper limit of any of about 20, 30, 40, 50, 75, 100, 125, 150, 200, 300, 400, 500, or 1000 protein-binding molecules, such as small epitope antibodies or small epitope aptamers.

In some embodiments, a kit comprises a first plurality of protein-binding molecules, such as small epitope antibodies or small epitope aptamers, for fractionation of a sample, and a second plurality of protein-binding molecules, such as small epitope antibodies or small epitope aptamers, for further fractionation of the fractions produced with the first plurality of protein-binding molecules. In some embodiments, the first and second pluralities of protein-binding molecules, such as small epitope antibodies or small epitope aptamers, each comprise any of at least about 10, 20, 30, 40, 50, 75, 90, 100, 125, 150, 200, 300, 400 or 500, with an upper limit of any of about 20, 30, 40, 50, 75, 100, 125, 150, 200, 300, 400, 500, or 1000 protein-binding molecules.

In some embodiments, the kits include protein-binding molecules, such as small epitope antibodies or small epitope aptamers, each labeled with a unique detectable label. In one embodiment, a kit comprises a first plurality of protein-binding molecules, such as small epitope antibodies or small epitope aptamers for fractionation of a sample, and a second plurality of protein-binding molecules, such as small epitope antibodies or small epitope aptamers, for further fractionation one or more fractions produced with the first plurality of protein-binding molecules, wherein the each different protein-binding molecule in the second plurality of protein-binding molecules comprises a unique detectable label. In one embodiment, a kit comprises about a first plurality of about 100 protein-binding molecules, such as small epitope antibodies or small epitope aptamers, for fractionation of a sample, and a second plurality of about 100 protein-binding molecule, such as small epitope antibodies or small epitope aptamers, for further fractionation of the fractions produced with the first plurality of protein-binding molecules, wherein each of the second plurality of protein-binding molecules each comprises a unique detectable label.

In some embodiments, the kits further comprise at least one protein cleaving agent. The protein cleaving agent may comprise an enzyme or a chemical cleaving agent.

In some embodiments, a kit further comprises instructions for use in accordance with any of the methods of the invention described herein, such as methods for reducing the complexity of a sample, methods for purifying and/or enriching a protein or a plurality of proteins, methods for isolating and/or separating a protein or a plurality of proteins, and/or methods for preparing a protein, a plurality of proteins, or a protein fraction for characterization, methods for preparing a protein, a plurality of proteins, or a protein fraction for mass spectrometry analysis, methods for identifying a protein or a plurality of proteins, methods for discovering one or more new proteins, methods for detection and/or quantification of a protein or a plurality of proteins in a sample, methods for characterizing a one or more proteins, methods for expression profiling, methods for identifying protein degradation products, methods for identifying change(s) in post-translational modification, and/or methods for determining the mass, the amount and/or identity of protein(s) in a sample. Instructions may be provided in printed form, on magnetic media, such as a CD or DVD, or in the form of a website address at which the instructions may be obtained.

The kits are in suitable packaging. Suitable packaging includes, but is not limited to, vials, bottles, jars, flexible packaging (e.g., sealed Mylar or plastic bags), and the like. In some embodiments, the kit comprises a container and a label or package insert(s) on or associated with the container. The label or package insert may indicate that the small epitope antibody(ies) or small epitope aptamers are useful for any of the methods described herein, e.g., method for reducing the complexity of a sample, or method for identifying a protein, characterizing a protein, and/or expression profiling. Instructions may be provided for practicing any of the methods described herein.

Components and Reaction Mixtures Useful in the Methods of the Invention

Small Epitope Antibody

In some embodiments, the methods of the invention use small epitope antibodies. As used herein, a "small epitope antibody" is an antibody that binds (generally specifically binds) a small peptide epitope. By virtue of the epitope specificity, small epitope antibodies generally recognize a multiplicity of proteins that comprise the small epitope to which the antibody binds. Insofar as the small epitope bound by the antibody is known, binding by a small epitope antibody provides information relating to amino acid content and/or sequence of protein(s) bound by the small epitope antibody. Small epitope antibodies are described, for example, in co-pending U.S. patent application Ser. Nos. 10/687,174 (publication no. 2004/0166106) and 10/921,380 (publication no. 2005/0131219), and in PCT Publication Nos. WO 04/035742 and WO 05/019831. Small epitope antibodies and methods of making small epitope antibodies are further discussed herein and exemplified in the Examples.

In some embodiments, the small epitope antibodies comprise a set of antibodies that recognize small epitopes with a constant or constrained C-terminal residue. A constant or constrained C-terminal residue may arise, for example, after a protein sample is treated with a protein cleaving agent that recognizes a specific amino acid (i.e. V8 protease cleaves at glutamic acid). Cleavage with V8 protease results in polypeptide fragments with a constant glutamic acid at the C-terminal end (with the exception of the true C-terminus of the protein). A constant or constrained C-terminal residue at the end of a small epitope reduces the total possible number of epitopes to be recognized, thereby reducing the number of small epitope antibodies needed to characterize a protein sample.

An antibody can encompass monoclonal antibodies, polyclonal antibodies, antibody fragments (e.g., Fab, Fab', $F(ab')_2$, Fv, Fc, etc.), chimeric antibodies, single chain (ScFv), mutants thereof, fusion proteins comprising an antibody portion, and any other modified configuration of the immunoglobulin molecule that comprises an antigen recognition site of the required specificity. The antibodies may be murine, rat, rabbit, human, or any other origin (including humanized antibodies). Small epitope antibodies may be produced by a number of methods known in the art, including, for example, production by a hybridoma, recombinant production, or chemical synthesis.

In another aspect, and as exemplified in the Examples, small epitope antibodies (e.g., human, humanized, mouse, rabbit, chimeric) may be made by using immunogens which express one or more small peptide epitopes, such as a small linear peptide epitope consisting of or consisting essentially of 3, 4, 5, 6, 7, 8, 9 or 10 amino acids.

Immunogens may be produced, for example, by chemical synthesis. Methods for synthesizing polypeptides are well known in the art. In some embodiments, the polypeptide immunogen is synthesized with a terminal cysteine to facilitate coupling to either KLH or BSA, as is known in the art. The terminal cysteine can be incorporated at the amino terminus of the polypeptide (which may minimize steric effects during immunization and screening), or at the carboxy terminus. In other embodiments, the polypeptide immunogen is synthesized as a multiple antigen polypeptide, or MAP.

The route and schedule of immunization of the host animal are generally in keeping with established and conventional techniques for antibody stimulation and production, as further described herein. General techniques for production of human, rabbit and mouse antibodies are known in the art and are described herein. Typically, the host animal is inoculated intraperitoneally with an amount of immunogen, including as described herein.

Hybridomas can be prepared from lymphocytes from an immunized host animal and immortalized myeloma cells using the general somatic cell hybridization technique of Kohler, B. and Milstein, C. (1975) *Nature* 256:495-497 or as modified by Buck, D. W. et al., (1982) *In Vitro*, 18:377-381. Available myeloma lines, including but not limited to, X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the small epitope antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas or progeny cells of the parent hybridomas that produce small epitope antibodies (such as monoclonal antibodies) may be used as source of antibodies or derivatives thereof, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human or other species of small epitope receptor, or a fragment of the human or other species of small epitope receptor, or a human or other species of small epitope receptor or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, SOCl2, or R1N=C=NR, where R and R1 are different alkyl groups can yield a population of antibodies (e.g., monoclonal antibodies).

If desired, the small epitope antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. It may be desirable to genetically manipulate the antibody sequence to obtain greater affinity to the small epitope and/or greater and/or altered specificity to the small epitope. It will be apparent to one of skill in the art that one or more polynucleotide changes can be made to the small epitope antibody and still maintain its binding ability to the small epitope.

Antibodies may be made recombinantly and expressed using any method known in the art. In another alternative, antibodies may be made recombinantly by phage display technology. See, for example, U.S. Pat. Nos. 5,565,332; 5,580,717; 5,733,743 and 6,265,150; Winter et al. (1994) *Annu. Rev. Immunol.* 12:433-455; Bradbury and Marks (2004) *J Immunological Methods* 290:29-49. In other embodiments, antibodies may be produced by yeast display (see, for example, Feldhaus and Siegel (2004) *J. Immunological Methods* 290:69-80) or by ribosome display (see, for example, Roberts and Szostak (1997) *Proc Natl Acad Sci* 94:12297-12302; Schaffitzel et al. (1999) *J. Immunological Methods* 231:119-135; Lipovsek and Plückthun (2004) *J. Immunological Methods* 290:51-67; http://www.discerna.co.uk/research.htm).

Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco), transgenic milk, or in other organisms. Methods for expressing antibodies recombinantly in plants or milk have been disclosed. See, for example, Peeters et al. (2001) *Vaccine* 19:2756; Lonberg, N. and D. Huszar (1995) *Int. Rev. Immunol* 13:65; and Pollock et al. (1999) *J Immunol Methods* 231:147. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for the desired small epitope.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

DNA encoding small epitope antibodies may be isolated and sequenced, as is known in the art. Generally, the monoclonal antibody is readily isolated and sequenced using conventional procedures (e.g., by using oligonucleotide probes that are capable of binding specifically to genes encoding the heavy and light chains of the monoclonal antibodies). The hybridoma cells serve as a preferred source of such cDNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al. (1984) Proc. Nat. Acad. Sci. 81: 6851, or by covalently joining to the immunoglobulin coding sequence all or part of the coding sequence for a non-immunoglobulin polypeptide. In that manner, "chimeric" or "hybrid" antibodies are prepared that have the binding specificity of a small epitope antibody (such as a monoclonal antibody) herein.

Small epitope antibodies may be characterized using methods well-known in the art, some of which are described in the Examples. For example, one method is to identify the epitope to which it binds, including solving the crystal structure of an antibody-antigen complex, competition assays, gene fragment expression assays, and synthetic polypeptide-based assays, as described, for example, in Chapter 11 of Harlow and Lane, *Using Antibodies, a Laboratory Manual*, Cold Spring Harbor Laboratory Press, Cold Spring Harbor, N.Y., 1999. In an additional example, epitope mapping can be used to determine the sequence to which a small epitope antibody binds. Epitope mapping is commercially available from various sources, for example, Pepscan Systems (Edelhertweg 15, 8219 PH Lelystad, The Netherlands). Polypeptides of varying lengths (e.g., at least 4-6 amino acids long) can be isolated or synthesized (e.g., recombinantly) and used for binding assays with an anti-small epitope antibody. In another example, the epitope to which the small epitope antibody binds can be determined in a systematic screening by using overlapping polypeptides derived from the small epitope extracellular sequence and determining binding by the small epitope antibody. Certain epitopes can also be identified by using large libraries of random polypeptide sequences displayed on the surface of phage particles (phage libraries), as is well known in the art.

Yet another method which can be used to characterize an anti-small epitope antibody is to use competition assays with other antibodies known to bind to the same antigen, i.e., to determine if the anti-small epitope antibody binds to the same epitope as other antibodies. Competition assays are well known to those of skill in the art.

The small epitope antibodies useful in this invention may be linked to a labeling agent (alternatively termed "label") such as a fluorescent molecule (such as a hapten or fluorescent bead), a binding partner, a solid support, or other agents to facilitate separation that are known in the art. Such agents are further described herein. In some methods, a plurality of small epitope antibodies is used for fractionation, each of which comprises a unique detectable label, such as, for example, a fluorescent microparticle, a microparticle comprising a quantum dot, or a barcode material, and characterization of a protein in a sample comprises detection of the unique detectable label(s) of one or more small epitope antibodies bound to the protein in a small epitope antibody-protein complex.

Antibodies that bind small linear peptide epitopes have been previously described, as shown in Table 1.

TABLE 1

Published short antibody epitope sequences

| Epitope Seq | Source protein | Antibody | Reference |
|---|---|---|---|
| NKS | Opa of N. meningitidis | U623, U506 | Malorny, B., et al. (1998) J Bacteriol 180(5): 1323-30. |
| NRQD (SEQ ID NO: 1) | Opa of *N. meningitides* | O521 | Id. |
| TTFL (SEQ ID NO: 2) | Opa of *N. meningitides* | AB419 | Id. |
| NIP | Opa of *N. meningitides* | W320/15, W124 | Id. |
| GAT | Opa of *N. meningitides* | P515 | Id. |
| EQP | MB of *U. urealyticum* | 3B1.5 | Zheng, X., et al., (1996) Clin Diagn Lab Immunol 3(6): 774-8. |
| WQDE (SEQ ID NO: 3) | Porcine ZP3 beta | mAb-30 | Afzalpurkar, A. et al. (1997) Am J Reprod Immunol 38(1): 26-32. |
| GPGR (SEQ ID NO: 4) | Gp120 of HIV-1 | 9x mAbs | Akerblom, L., et al. (1990) Aids 4(10): 953-60. |
| D(A/S)F* | Phosphofructokinase-1 | alpha-F3 | Hollborn, M., et al. (1999) J Mol Recognit 12(1): 33-7. |
| (D/S)GY(A/G)** (SEQ ID NO: 5) | Crotoxin | A-56.36 | Demangel, C., et al. (2000) Eur J Biochem 267(8): 2345-53 |

*DAF and DSF.
**Refers to DGYA (SEQ ID NO: 76), DGYG, SGYA (SEQ ID NO: 78) and SGYG (SEQ ID NO: 79).

Small Epitope Aptamer

In some embodiments, the methods of the invention use small epitope aptamers. As described above for small epitope antibodies, by virtue of the epitope specificity, aptamers may be designed and/or selected to recognize a multiplicity of proteins that comprise the epitope to which the aptamer binds. Insofar as the epitope bound by the aptamer is known, binding by an aptamer provides information relating to amino acid content and/or sequence of protein(s) bound by the aptamer.

In some embodiments, the small epitope aptamers comprise a set of aptamers that recognize small epitopes with a constant or constrained C-terminal residue. As described above, a constant or constrained C-terminal residue may arise, for example, after a protein sample is treated with a protein cleaving agent that recognizes a specific amino acid (i.e. V8 protease cleaves at glutamic acid). Cleavage with V8 protease results in polypeptide fragments with a constant glutamic acid at the C-terminal end (with the exception of the true C-terminus of the protein). A constant or constrained C-terminal residue at the end of a small epitope reduces the total possible number of epitopes to be recognized, thereby reducing the number of small epitope aptamers needed to characterize a protein sample.

"Aptamers" or "nucleic acid ligands" are nucleic acid molecules having specific binding affinity to non-nucleic acid or nucleic acid molecules. Aptamers are described e.g. in U.S. Pat. Nos. 5,475,096; 5,270,163; 5,589,332; 5,589,332; and 5,741,679. As used herein, "aptamer" or "nucleic acid ligand" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

Aptamers, like antibodies, are capable of specifically binding to selected targets. Aptamers are created by an in vitro selection process from pools of random sequence oligonucleotides, and have been generated for over 100 proteins. A typical aptamer is 10-15 kDa in size (about 30-45 nucleotides), binds its target with sub-nanomolar affinity and is able to discriminate between closely related targets. Studies have shown that aptamers are capable of using the same types of binding interactions i.e. hydrogen bonding, electrostatic interactions, hydrophobic contacts and steric exclusion, that drive affinity and specificity in antibody-antigen complexes.

In addition to having high affinity and specificity, aptamers have other desirable characteristics. Aptamers are produced by an entirely in vitro process, allowing for the rapid generation of large number of aptamers with differing specificities. In vitro selection allows the specificity and affinity of the aptamer to be tightly controlled and can be biased, through appropriate modifications to the selection procedure, toward the recovery of aptamers to a particular region of a target or with specific binding properties (e.g. sensitivity to temperature, pH, salt concentration or composition, etc.). The in vitro selection process also allows for the generation of aptamers against epitopes within non-immunogenic targets.

Aptamers are typically chemically synthesized and consequently can be readily produced and scaled as needed to meet production demands. Aptamers are amenable to a wide variety of precise chemical modifications that can modulate their behavior in vitro and in vivo.

Aptamers are chemically stable and conformationally resilient. They can recover their native structure and activity following insult, for example, high temperature and denaturants. Aptamers may be stored for extended periods of time at room temperature as lyophilized powders.

Aptamer selection is usually performed using a process termed Systematic Evolution of Ligands by EXponential enrichment or "SELEX™". This process is described in e.g., U.S. Pat. Nos. 5,475,096; 5,670,637; 5,696,249; and 5,270,163. The method relies on standard molecular biological techniques and can be carried out manually or in an automated fashion. "SELEX™" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The process can be broken down conceptually into a series of steps: pool preparation, selection, separation, amplification and aptamer isolation.

A candidate mixture or large "library" of nucleic acid molecules of differing sequence is prepared. The source of a candidate mixture can be from naturally-occurring nucleic acids or fragments thereof, chemically synthesized nucleic acids, enzymatically synthesized nucleic acids or nucleic acids made by a combination of the foregoing techniques. The nucleic acid molecules generally include regions of fixed sequences (i.e., each member of the candidate mixture contains the same sequences in the same location) and regions of randomized sequences. The fixed sequence regions are selected either: a) to assist in the amplification steps described below; b) to mimic a sequence known to bind to the target; or c) to enhance the potential of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent). The length of the randomized section of the nucleic acid is generally between 8 and 250 nucleotides, preferably between 8 and 60 nucleotides. Each molecule in the library (often as many as $10^{15}$ different molecules) contains a unique nucleotide sequence that can, in principle, adopt a unique three-dimensional shape. A few of these molecules present a surface that is able to bind to a target molecule.

The selection step is designed to find those molecules with the greatest affinity for a target of interest. The candidate mixture or library is contacted with the selected target (e.g., a protein, a peptide containing an epitope, a small molecule, or a supramolecular structure) under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target. The nucleic acid molecules in the candidate mixture or library with weak or no affinity for the target will, on average, remain free in solution while those nucleic acids with some capacity to bind the target will tend to associate with it.

The nucleic acids with the highest affinity for the target are separated from those nucleic acids with lesser affinity to the target. Because only an extremely small number of sequences (and possibly only one molecule of nucleic acid) corresponding to the highest affinity nucleic acids exist in the candidate mixture, it is generally desirable to set the separation criteria so that a significant amount of the nucleic acids in the candidate mixture (approximately 5-10%) is retained during separation. Any one of several methods known in the art may be used to physically isolate the nucleic acid-target complexes from the unbound molecules in the mixture. The target-bound molecules are purified away from the target and used in subsequent steps of the process.

"Separation" refers to any process whereby nucleic acid ligands bound to target molecules can be separated from nucleic acids not bound to target molecules. More broadly stated, separation allows for the fractionation of all the nucleic acids in a candidate mixture into at least two pools based on their relative affinity to the target molecule. Separation can be accomplished by various methods known in the art. Nucleic acid-protein pairs may be bound to nitrocellulose filters while unbound nucleic acids do not bind and are washed away. Columns which specifically retain nucleic acid-target complexes may be used for separation. Other techniques include, but are not limited to, liquid-liquid partitioning, filtration gel retardation, and density gradient centrifugation.

The nucleic acids selected during the separation step(s) as having the relatively higher affinity to the target are then amplified to create a new candidate mixture that is enriched in nucleic acids having a relatively higher affinity for the target. Nucleic acid amplification methods are well known in the art, e.g. PCR, RT-PCR, etc. The enriched library or new candidate mixture is used to initiate a new cycle(s) of selection, partitioning and amplification.

By repeating the separation and amplifying steps described herein (e.g. 5-15 cycles), each newly formed candidate mixture contains fewer and fewer unique sequences, and the average degree of affinity of the nucleic acid mixture to the target increases. Taken to its extreme, the SELEX™ process yields a candidate mixture containing one or a small number of unique nucleic acids representing those nucleic acids from the original candidate mixture having the highest affinity to the target molecule. Individual molecules in the mixture are then isolated, their nucleotide sequences are determined, and their properties with respect to binding affinity and specificity are measured and compared. In most cases, the nucleic acid molecules or aptamers are further refined to eliminate any nucleotides that do not contribute to target binding or to aptamer structure.

Epitopes

Generally, a small epitope binding molecule, (such as a small epitope antibody or a small epitope aptamer) binds a short, linear peptide "small epitope" of 3, 4, or 5 sequential (consecutive) amino acids. Alternatively, in some embodiments, a small epitope binding molecule binds a discontinuous amino acid sequence within a polypeptide. In some embodiments, a small epitope binding molecule binds an epitope consisting of or consisting essentially of any of about 2, 3, 4, 5, 6, 7, 8, 9, or 10 amino acids. In some embodiments, a small epitope binding molecule binds an epitope consisting of or consisting essentially of 2 to 10, 3 to 8, or 3 to 5 amino acids. In some embodiments, a small epitope binding molecule binds an epitope consisting of or consisting essentially of less than any of about 10, 9, 8, 7, 6, 5, 4, or 3 amino acids. In some embodiments, a population of small epitope binding molecules binds epitopes consisting of or consisting essentially of about 3 to about 5 amino acids. In some embodiments, a population of small epitope binding molecules binds epitopes consisting of or consisting essentially of 2 to 10, 3 to 8, or 3 to 5 amino acids. In some embodiments, a population of small epitope binding molecules binds epitopes consisting of or consisting essentially of any of about 2, 3, 4, 5, 6, 7, 8, 9, or 10 amino acids. In some embodiments, a population of small epitope binding molecules binds epitopes consisting of or consisting essentially of less than any of about 10, 9, 8, 7, 6, 5, 4, or 3 amino acids. A population of small epitope binding molecules comprises a plurality of small epitope binding molecules. In one embodiment, the plurality of small epitope binding molecules binds epitopes of the same number of amino acids. In other embodiments, the plurality of small epitope binding molecules binds epitopes of a mixture of different numbers of amino acids. In any of the embodiments described herein, an epitope may be a sequential or discontinuous sequence within a polypeptide, as described below. In some embodiments, one or more small epitope binding molecule(s) may be comprised within a mixture of binding molecules that comprises binding molecules that bind to epitopes larger that the epitopes recognized by the one or more small epitope binding molecule(s).

In some embodiments, the small epitope binding molecule binds an epitope consisting of or consisting essentially of 3 sequential amino acids (termed a 3mer), four sequential amino acids (termed a 4mer), or five sequential amino acids (termed a 5mer). In other embodiments, the small peptide binding molecule binds a small "discontinuous" or "degenerate" linear peptide sequence, such as the linear peptide sequence YCxC, wherein x represents any of the 20 natural amino acids (a degenerate linear sequence). In other embodiments, the small epitope binding molecule binds a non-sequential (discontinuous) sequence within a polypeptide based on conformational proximity of amino acids within the polypeptide to form the epitope (for example, a conformational epitope formed by proximity of amino acid residues due to secondary structure within a folded polypeptide). In still other embodiments, the small epitope binding molecule may bind an epitope consisting of an amino acid sequence that is predicted to be antigenic, using methods well known in the art for predicting antigenicity. Antibodies that bind small linear peptide epitopes have been previously described, as shown in Table 1, above. In some embodiments, the same antibody or aptamer may bind a sequential sequence on one or more proteins and a discontinuous sequence on one or more proteins.

Small epitope binding molecules generally recognize a multiplicity of proteins that comprise the small epitope to which the binding molecule binds. In some embodiments, the small epitope binding molecule binds to an epitope present one or more times in about any of 0.1%, 0.5%, 1%, 2%, 3%, 4%, 5%, 10%, or more of proteins in a sample. In still other embodiments, the small epitope binding molecule binds to an epitope present one or more times in about 0.1% to 1% of proteins in a sample. In still other embodiments, the small epitope binding molecule binds to an epitope present one or more times in approximately 1-5% of proteins in a sample. In still other embodiments, the small epitope binding molecule binds to an epitope present one or more times in about 0.1% to 1% of proteins in a sample, wherein the small binding molecule epitope binds to a linear peptide epitope consisting of or consisting essentially of 3 amino acids, 4 amino acids or 5 amino acids. In still other embodiments, the small epitope binding molecule binds to an epitope present one or more times in about 1-5% of proteins in a sample, wherein the small binding molecule epitope binds to a linear peptide epitope consisting of or consisting essentially of 3 amino acids, 4 amino acids or 5 amino acids. In still other embodiments, the small epitope binding molecule binds to an epitope present one or more times in about 5-7% or about 5-10% of proteins in a sample, wherein the small binding molecule epitope binds to a linear peptide epitope consisting or consisting essentially of 3 amino acids, 4 amino acids or 5 amino acids. In some embodiments, a plurality of small epitope binding molecules collectively bind to one or more epitopes present one or more times in any of at least about 0.1%, 0.5%, 1%, 2%, 3%, 4%, 5%, 10%, or more of proteins in a sample. In some embodiments, a plurality of small epitope binding molecules binds to an epitope present one or more times in any of about 0.1 to 1%, 1 to 5%, 5 to 7%, or 5 to 10% of proteins in a sample. Methods for empirically assessing frequency of an epitope in a sample include: assessment using biochemical approaches, such as binding of an antibody followed by analysis using, for example, 2D gels or mass spectrometry, and sequence-based analysis, using, for example, amino acid or nucleic acid sequence databases such as GenBank and SwissProt. Suitable databases are further described herein.

In some embodiments, the epitope recognized by a small epitope binding molecule further comprises a C-terminal amino acid recognized as a cleavage site by an endopeptidase. For example, the epitope could comprise a C-terminal arginine and/or a lysine, which are each recognized by trypsin as a cleavage site. Or, the epitope could comprise a C-terminal glutamic acid which is recognized by *Staphylococcus* protease. Following endopeptidase digestion of a protein mixture, the amino acid recognized by the endopeptidase is generally found at the C-terminus of the target peptide; accordingly, an epitope encompassing such an amino acid will also be found at the C-terminus of a target polypeptide, which may increase immunogenicity, and increase the binding energy associated with binding molecule-target polypeptide binding.

In some embodiments, the small epitope binding molecule binds its cognate epitope with an affinity of a binding reaction of at least about $10^{-7}$ M, at least about $10^{-8}$ M, or at least about $10^{-9}$ M, or at least about $10^{-10}$, or at least about $10^{-11}$ or at least about $10^{-12}$ or lower. Binding affinity may be measured by well-known methods in the art, including, for example, by surface plasmon resonance (Malmborg and Borrebaeck (1995) *J. Immunol. Methods* 183(1):7-13; Lofas and Johnsson (1990) *J. Chem. Soc. Chem. Commun.* 1526). In some embodiments, a binding interaction will discriminate over adventitious or non-specific binding interactions in the reaction by at least two-fold, at least five-fold, at least 10-fold to at least 100-fold or more.

In some embodiments of methods of the invention as described herein, a protein-containing sample or fraction is fractionated with a plurality of small epitope binding molecules containing any of about 10, 20, 30, 40, 50, 75, 100, 125, 150, 200, 300, 400, 500, 1000, or more small epitope binding molecules. In some embodiments, the sample or fraction is fractionated with any of least about 10, 20, 30, 40, 50, 75, 90, 100, 125, 150, 200, 300, 400, 500, 1000, or more small epitope binding molecules. In some embodiments, the sample or fraction is fractionated with any of at least about 10, 20, 30, 40, 50, 75, 90, 100, 125, 150, 200, 300, 400 or 500 small epitope binding molecules, with an upper limit of any of about 20, 30, 40, 50, 75, 100, 125, 150, 200, 300, 400, 500, or 1000 small epitope binding molecules. In some aspects, a plurality of small epitope binding molecules containing 10 or more different small epitope binding molecules is used for fractionation of a sample or fraction in a method of the invention. In one embodiment, a first plurality of small epitope binding molecules containing about 100 different small epitope binding molecules is used for fractionation of a protein containing sample to produce first fractions, and a second plurality containing about 100 different small epitope binding molecules is used for fractionation of each first fraction to produce second fractions, wherein the first plurality of small epitope binding molecules may comprise the same or different small epitope binding molecules than the second plurality of small epitope binding molecules.

It is understood that the identity (sequence) of the epitope(s) to which the small epitope binding molecule binds to may be used in combination with any of the methods described herein to, for example, identify proteins. In some embodiments, the small epitope identity is known. In other embodiments, the identity of the epitope is predictable using methods known in the art.

As discussed herein, binding molecules may be contacted with a sample or fraction one at a time or in groups of two or more binding molecules. In some embodiments, contacting is serial (sequential or iterative), e.g., a single binding molecule or group of binding molecules is contacted with the sample and separated, and a second binding molecule or group of binding molecules is contacted with the sample and separated. In other embodiments, contacting is in parallel, e.g., a group of binding molecules is contacted with the sample and separated. It is appreciated that contacting may be both in parallel and serial, as when different groups of binding molecules are serially contacted with a sample. Groups of binding molecules may be overlapping in composition (e.g., group 1=binding molecule A, B, C, D; group 2=binding molecule B, C, D, E, etc.).

It is evident that the number of small epitope binding molecules that are useful in the methods for fractionation of a sample as described herein depends on the use, application, and/or subsequent analysis contemplated for the protein prepared using one or more small epitope binding molecules. In some applications, such as detection of a protein(s) comprising a cognate epitope recognized by a small epitope binding molecule, a single small epitope binding molecule (or, in some embodiments, a small number of small epitope binding molecules) may be used to prepare, purify and/or enrich a fraction of protein(s) that comprises the protein for which subsequent detection (or other analysis) is desired. Then, the separated protein can be subjected to further analysis. In other embodiments, use of a set of two or more small epitope binding molecules may be useful. For example, in applications such as protein discovery and, in some embodiments, expression profiling, it may be desirable to use a multiplicity of small epitope binding molecules, such that a large multiplicity of proteins (such as essentially all protein in the starting sample) will be enriched and/or purified. Use of a multiplicity of small epitope binding molecules is also useful in applications in which purification and/or enrichment of new protein(s) or protein forms is desired (for example, because information regarding target protein sequence is unknown). As an illustrative example relating to embodiments involving fractionation of a multiplicity of proteins in a sample (such as essentially all proteins in a sample) shown, knowledge of the sequence and/or the length of the cognate amino acid epitope recognized by the small epitope binding molecule permits an estimate regarding the expected frequency of the epitope(s) recognized by the small epitope binding molecule(s) within the protein sample. As shown in Table 2, there are a total of 8,000 ($20^3$), 160,000 ($20^4$) and 3,200,000 ($20^5$) random combinations for 3mer, 4mer and 5mer linear peptide sequences, respectively. Considering 437 amino acids as an average length of a protein, the probability that any 3mer will appear in an average protein is 5%. This is calculated from the probability a protein is detected by a single anti-3mer antibody is 0.0546. The probability increases to about 1 when 20 anti-3mer antibodies are used, and the probability increases to 5.46 when 100 anti-3mer antibodies are used. Such calculations are routine. Using binding molecules to 100 different 3mers would theoretically represent a 5-fold redundancy. A small epitope binding molecule may also recognize a degenerate linear epitope, for example a short peptide, such as YCxC, where x represents two or more of the 20 standard amino acids.

TABLE 2

Distribution properties of short linear amino acid peptides

| | Epitope amino acid length (n) | | | |
|---|---|---|---|---|
| | 2 | 3 | 4 | 5 |
| # of random combinations ($20^n$) | 400 | 8,000 | 160,000 | 3,200,000 |
| Appearance rate in a 437 amino acid protein ($437/20^n$) | 1.0925 | 0.0546 | 0.0027 | 0.0001 |
| Detection rate by 100 anti-nmer antibodies ($100 \times 437/20^n$) | 109.25 | 5.46 | 0.27 | 0.01 |
| Detection rate by 1000 anti-nmer antibodies ($1000 \times 437/20^n$) | 1,092 | 54.6 | 2.7 | 0.1 |

In some embodiments, the epitope recognized by a small epitope binding molecule comprises a C-terminal amino acid recognized as a cleavage site by a protease or other cleaving agent. Following cleavage of a protein mixture, the amino acid(s) recognized by the protease or cleaving agent is generally found at the C-terminus of each polypeptide fragment. The exception will be the original or true C-terminus peptide unless the original C-terminus peptide naturally comprises the amino acid recognized by the protease as its terminal amino acid.

In some embodiments, the total number of potential combinations of 3mer amino acid sequences for a 3mer epitope is 8,000. In some embodiments, amino acids cysteine and methionine are excluded so that they may be used for coupling reactions, e.g. to label the protein. In some embodiments, proline may be excluded due to the tendency of this amino acid to introduce kinks into polypeptides which can potentially pose a problem for immunogenicity and/or binding interactions. The exclusion of these 3 amino acids reduces the potential combinations of 3mer amino acid sequences to 4,900. In some embodiments, the C-terminal amino acid is constrained after protein cleavage, thereby reducing the potential combinations of 3mer amino acid sequences to 256.

In some embodiments, protein cleavage at specific amino acids results in constraint of the C-terminal amino acid in each polypeptide fragment generated. For example, the potential combinations of 3mer amino acid sequences is reduced due to the constrained C-terminal amino acid. As shown in Table 3, there are a total of 8,000 ($20^3$) random combinations for 3mer linear peptide sequences. Considering the average protein size in the secreted proteome is 437 amino acids, the average occurrence probability for any 3mer linear peptide sequence is 0.055. In Table 3, for "average number of peptides for given amino acids recognized by a protease in a 437 amino acid protein," the numbers at the top of the table represent the number of amino acids that any protease or combination of protease would cut at. For example, Staph VIII protease cuts primarily at one amino acid, glutamic acid. Therefore, if assumed that there is a random distribution of amino acids, Staph VIII would cut the protein into approximately 22 peptides (437/20). These peptides would all have a glutamic acid at the C-terminus with the exception of the true C-terminal peptide. Similarly, the protease trypsin cuts at two amino acids, lysine and arginine. Therefore, the protein would be cut into approximately 44 peptides (437/20×2). These peptides would have either a lysine or an arginine at the C-terminus, with the exception of the true C-terminal peptide. The "average peptide size for given aa's recognized by protease" is the length of the protein divided by the number of cut sites. For example, Staph VIII, cuts approximately 22 times in an average protein of 437 amino acids, therefore the average peptide size would be 20 amino acids (437/22). For "occurrence probability in 437 aa protein with 1 aa constrained," the numbers at the top of the table represent the number of amino acids in addition to the constrained amino acid at the C-terminus. For example, in the column under 2 amino acids, this would represent binding molecules that actually recognize a 3mer, i.e. 2 amino acids plus the 1 constrained amino acid. Therefore, the occurrence probability for a 3mer linear peptide sequence with its C-terminal amino acid constrained to a specific amino acid is 0.055. The probability that a polypeptide fragment is detected by a single C-terminal constrained 3mer binding molecule is 0.055 and the probability increases to about 5.5 when 100 C-terminal constrained 3mer binding molecules are used. Without being bound by theory, binding molecules to C-terminal 3mers with a constrained C-terminal amino acid may provide better coverage of proteins, (i.e. bind to more proteins) using fewer binding molecules.

TABLE 3

Distribution properties of short linear amino acid peptides with constrained C-terminus amino acid

| | Number of amino acids (n) | | | | |
|---|---|---|---|---|---|
| | 1 | 2 | 3 | 4 | 5 |
| # of random combinations ($20^n$) | 20 | 400 | 8,000 | 160,000 | 3,200,000 |
| Appearance rate in a 437 amino acid protein ($437/20^n$) | 21.85 | 1.09 | 0.055 | 0.0027 | 0.00014 |
| Detection rate with 100 anti-nmer binding molecules ($100 \times 437/20^n$) | 2,185 | 109 | 5.5 | 0.27 | 0.014 |
| Average # peptides for given aa's recognized by protease in 437 aa protein | 21.85 | 43.7 | 65.55 | 87.4 | 109.25 |
| Average peptide size for given aa's recognized by protease | 20 | 10 | 6.7 | 5 | 4 |
| Occurrence probability in 437 aa protein with 1 aa constrained | 1.093 | 0.055 | 0.003 | 0.000 | 0.000 |

TABLE 3-continued

Distribution properties of short linear amino acid peptides with constrained C-terminus amino acid

| | Number of amino acids (n) | | | | |
|---|---|---|---|---|---|
| | 1 | 2 | 3 | 4 | 5 |
| Detection probability with 100 anti-nmer binding molecules with 1 aa constrained | 109 | 5.46 | 0.27 | 0.140 | 0.001 |
| Occurrence probability in 437 aa protein with 2 aa constrained | | 0.109 | 0.005 | 0.000 | 0.000 |
| Detection probability with 100 anti-nmer binding molecules with 2 aa constrained | | 10.925 | 0.546 | 0.027 | 0.001 |
| Occurrence probability in 437 aa protein with 3 aa constrained | | 0.164 | 0.008 | 0.000 | 0.000 |
| Detection probability with 100 anti-nmer binding molecules with 3 aa constrained | | 16.4 | 0.8 | 0.00 | 0.00 |

It should be understood that the number of small epitope binding molecules, such as small epitope antibodies or small epitope aptamers, useful in the methods of the invention depends on various factors, including, for example, the use, application, and/or subsequent analysis contemplated for the protein fraction bound by the small epitope binding molecules, complexity of the sample (in terms of number of expected or estimated or previously determined proteins, including protein variants such as splice variants), average size of the proteins in the sample, treatment (i.e. cleavage) of the protein sample, frequency that the cognate epitope is present or predicted to be present in a sample, binding affinity and/or specificity of the small epitope binding molecules; knowledge of target protein(s), and stability of the small epitope binding molecule. Such factors are well known in the art and are further discussed herein.

In some embodiments, one or more of the following considerations are used in the design of small epitope binding molecules, including, but not limited to, antibodies and aptamers (whether designed to be used singly or in a population) that result in an epitope frequency with sufficient redundancy to yield optimal coverage of the proteins present in a sample. In some embodiments, a group of small epitope binding molecules designed according to one or more of the following considerations is capable of binding to cognate epitopes on at least about any of 10, 20, 30, 40, 50, 60, 70, 80, 90, or 95% of the proteins in a sample.

Epitope size: Epitopes that are small enough to occur frequently in the proteome but large enough to confer sufficient binding energy when recognized by a cognate binding molecule are desired. In some embodiments, the epitope size recognized by each binding molecule is 3, 4, or 5 amino acids.

Epitope abundance: Optimal epitope abundance enables each small epitope binding molecule to bind to about 100 to about 150 proteins or polypeptide fragments of about 20 to about 100 amino acids in length. This abundance level matches the resolving power of most mass spectrometers without requiring MS-MS and collision-induced dissociation (CID). Epitopes of the appropriate abundance are preferable for achievement of the desired MS resolution and sensitivity.

Sampling redundancy: A sufficiently large collection of small epitope binding molecules is used to permit binding to about 3 to about 5 epitopes per protein per proteome of interest. This design feature provides for sampling redundancy to accommodate the variability expected in both expression levels for different proteins and binding efficiency for each binding molecule in the collection.

Affinity: The tightness of binding between small epitope binding molecules and their epitopes affects the sensitivity of protein profiling. In some embodiments, each binding molecule in a collection binds with high enough affinity to ensure that sufficient analyte is captured for MS analysis.

Frequency of binding: Frequency of binding of small epitope binding molecules is high so that peptides present within each bound peptide fraction contain a common epitope. This provides sampling redundancy and facilitates bioinformatic determination of peptide identity.

Contacting a Sample or Fraction with Small Epitope Antibody(ies) and Separation of Protein from a Protein-Antibody Complex Methods and conditions for contacting an antibody with a protein in a sample are well known in the art. Antibodies may be contacted with a sample or fraction one at a time or in groups of two or more antibodies. In some embodiments, contacting is serial (sequential, or iterative), e.g., a single antibody or group of antibodies is contacted with the sample; separated; and a second antibody or group of antibodies is contacted with the sample, and separated, and so on. In other embodiments, contacting is in parallel, e.g., a group of antibodies is contacted with the sample, and separated. It is appreciated that contacting may be both in parallel and serial, as when different groups of antibodies are serially contacted with a sample. Groups of antibodies may be overlapping in composition (e.g., group 1=antibody A, B, C, D; group 2=antibody B, C, D, E, etc.) or different in composition. Contacting of an antibody with protein may occur with both antibody and protein in a liquid medium or may occur with one component (antibody or protein) bound or associated with a solid support and the other component in a liquid medium. In one embodiment, a liquid (e.g., aqueous) protein containing sample is contacted with a small epitope antibody that is bound to or associated with a solid support.

In some embodiments involving parallel contacting, it is desirable for small epitope antibodies to be individually separable, for example, by linking each antibody to a unique detectable label as described herein, use of individually separable binding partners, immobilization of antibody in, e.g., different wells of a multi-well plate, use of antibody arrays, and the like. Insofar as the small epitope bound by the antibody is known, binding by a small epitope antibody provides information relating to amino acid content and/or sequence of protein(s) bound by the small epitope antibody. In embodiments wherein knowledge of the cognate small epitope is desired, it may be convenient to individually separate the small antibodies (such that the protein bound by each small epitope antibody is kept separate). However, individual separation or separability is not required in every embodiment. For example, small epitope antibodies may be combined in small pools of two or more antibodies that possess overlapping antibody composition, such as (1) antibodies ABC; (2) antibodies CDE; (3) antibodies FGH, and (4) antibodies HIJ. Following separation of antibody-protein complexes, and separation of antibody from antibody-protein complexes, information regarding presence or absence of a particular small epitope may be inferred based on membership in a particular group.

In some embodiments of methods of the invention, small epitope antibody-protein complexes are separated from unbound protein in a sample or fraction prior to detection of proteins in the complexes. In other embodiments, proteins are detected without separation from unbound protein. In some embodiments, proteins are separated from small epitope antibody-protein complexes prior to detection.

To facilitate separation of the antibody-protein complex from unbound protein in the sample, the antibody may be linked to an agent that facilitates separation, such as a binding partner (e.g., biotin, oligonucleotide, aptamer), a solid support (such as a bead or matrix, including a microarray or multi-well plate); or any other agent known in the art. Linking may be covalent or non-covalent, and may be direct or indirect. Methods for linking antibodies to such agents are well known in the art. See, e.g. Kennedy et al. (1976) *Clin. Chim. Acta* 70:1-31, and Schurs et al. (1977) *Clin. Chim. Acta* 81:1-40 (describing coupling techniques, including the glutaraldehyde method, the periodate method, the dimaleimide method, the m-maleimidobenzyl-N-hydroxy-succinimide ester method, all of which methods are incorporated by reference herein).

Methods for separating an antibody-protein complex from a sample are known in the art and include use of a capture agent that binds a binding partner (e.g., avidin to capture a biotin-linked antibody; an oligonucleotide to capture an oligonucleotide linked to an antibody); Physical separation may also be used, such as sedimentation, filtration, FACS (for example, using beads that are labeled with a spectral signature), and magnetic separation (when the antibody is linked to a matrix with magnetic properties, such as a magnetic bead).

Many binding partners are known in the art (e.g., a dinitrophenyl group, digoxigenin, fluorophores, Oregon Green dyes, Alexa Fluor 488 (Molecular Probes), fluorescein, a dansyl group, Marina Blue (Molecular Probes), tetramethylrhodamine, Texas Red (Molecular Probes), BODIPY (4,4-difluoro-4-bora-3a,4a-diaza-s-indacene; U.S. Pat. No. 4,774, 339) dyes, etc.) that can be used in the present invention. Antibodies that can be used as capture reagents and specifically bind to binding agents are commercially available from vendors such as Molecular Probes, Eugene, Oreg. These antibodies include antibodies that can specifically bind to a dinitrophenyl group, a digoxigenin, a fluorophore, Oregon Green dyes, Alexa Fluor 488 (Molecular Probes), fluorescein, a dansyl group, Marina Blue (Molecular Probes), tetramethylrhodamine, Texas Red (Molecular Probes), and a BODIPY dye (Molecular Probes). Any suitable ligand and anti-ligand may also be used.

Oligonucleotides can be used as binding partners and capture reagents. Oligonucleotides include nucleic acids such as DNA, RNA, and mixed RNA/DNA molecules. The oligonucleotide that is used as the affinity label should be able to hybridize to the sequence of the oligonucleotide present on the capture reagent. Those of skill in the art will recognize that many different oligonucleotide sequences can be designed that will hybridize to each other. Important considerations for designing such oligonucleotide pairs include the actual nucleotide sequence, the length of the oligonucleotides, the hybridization conditions (e.g., temperature, salt concentration, presence of organic chemicals, etc.) and the melting temperature of the oligonucleotide.

Solid supports suitable for immobilizing (linking) antibodies or proteins from a sample (and modifications to render solid supports suitable for immobilizing antibodies) are well known in the art. Examples of a solid support include: a bead (including magnetized beads), micro-well plate, and a protein microarray (e.g., technology owned by Zyomyx, Inc. See, e.g. U.S. Pat. No. 6,365,418). Thus, for example, CdSe—CdS core-shell nanocrystals enclosed in a silica shell can be easily derivatized for coupling to a biological molecule. Bruchez et al. (1998) *Science* 281: 2013-2016. Similarly, highly fluorescent quantum dots (zinc sulfide-capped cadmium selenide) have been covalently coupled to biomolecules for use in ultrasensitive biological detection. Warren and Nie (1998) *Science* 281: 2016-2018. Fluorescently labeled beads are commercially available from Luminex and Quantum Dot.

The bound protein (or in some embodiments, polypeptide fragments) may be released from the antibody-protein complex using conventional immunoaffinity elution conditions such as acidic pH, ionic strength, detergents or combinations of the above. Generally, peptide or protein is de-salted for subsequent fractionation, characterization, or other analysis.

Protein Cleaving Agent

In some embodiments, the methods of the invention further comprise treating proteins in a sample or fraction with a protein cleaving agent, whereby polypeptide fragments are generated. In some embodiments, the sample is contacted with a protein cleaving agent prior to fractionation of a sample, or prior to contacting a sample or fraction with at least one protein-binding molecule. In some embodiments, protein-binding molecule-protein complexes (e.g., small epitope antibody-protein complexes) are contacted with a protein cleaving agent, or protein is contacted with a protein cleaving agent after separation of protein from the complex.

Protein cleaving agent treatment generates protein cleavage fragments (such as polypeptides), which can facilitate subsequent analysis, e.g., mass spectral analysis, of the amount of protein and/or the identity of protein(s) in a sample(s). In particular, treatment with a protein cleaving agent treatment can facilitate the analysis of proteins whose molecular masses exceed 25 kDa. Protein cleaving reagent treatment also may facilitate accessibility and/or access of protein binding molecules such as, small epitope antibodies or small epitope aptamers, to a cognate epitope. Protein cleaving agents are well known in the art, and are further discussed herein. In some embodiments, one protein cleaving agent is used. In other embodiments, more than one protein cleaving reagent is used. In some embodiments, more than one type of protein cleaving agent is used with respect to a single sample (e.g., two or more types of proteases, two or more types of chemical cleaving agents, or a combination of one or more protease and one or more chemical cleaving agent). Conditions for treatment with a protein cleaving agent are well known in the art.

In one embodiment, a protein cleaving agent is a protease. Examples of proteases that can be used as protein cleaving agents, include, but are not limited to, chymotrypsin, trypsin (Arg, Lys cleavage sequence), thermolysin (Phe, Leu, Iso, Val cleavage sequence), V8 protease (Glu cleavage sequence), Endoproteinase Glu-C, Endoproteinase Asp-N, Endoproteinase Lys-C, Endoproteinase Arg-C, Endoproteinase Arg-N, Factor Xa protease, thrombin, enterokinase, V5 protease, and the tobacco etch virus protease. Proteases useful in the methods of the invention can be genetically engineered and/or chemically modified to prevent autolysis. It is appreciated that an enzymatic protein cleaving agent (such as a protease) can be modified to facilitate removal of the protease from the polypeptide cleavage products following polypeptide cleavage. Such modifications are known in the art and include: (1) bead-bound (e.g., latex, silica or magnetic bead) protease, (2) haptenated protease, (3) affinity depletion of the protease (with, for example, a bead-bound anti-protease, or bead-bound non-cleavable substrate) and/or (4) size exclusion chromatography. The activity of a protease can be inhibited, for example, by treating with heat, a protease inhibitor, a metal chelator (e.g., EGTA, EDTA), etc.

In another embodiment, a protein cleaving agent is a chemical cleaving agent, such as a chemical substance or compound that cleaves polypeptides and peptide bonds. Non-limiting examples of chemical cleaving agents include cyanogen bromide (which cleaves at methionine residues), hydroxylamine (which cleaves between an Asn and a Gly residue), and acid pH (which can cleave an Asp-Pro bond) (see e.g., Ausubel et al., supra).

In still further embodiments, phosphatases (e.g., alkaline phosphatase, acid phosphatase, protein serine phosphatase, protein tyrosine phosphatase, protein threonine phosphatase, etc.), lipases, and other enzymes can be employed as protein cleaving agents.

In some embodiments, the protein cleaving agent recognizes and cleaves at specific amino acid residues resulting in polypeptide fragments that have a constant or constrained amino acid residue at the C-terminal end and at a C-terminal small epitope. A constant or constrained C-terminal residue may arise, for example, after a protein sample is treated with a protein cleaving agent that recognizes a specific amino acid (i.e. V8 protease cleaves at glutamic acid). Cleavage with V8 protease results in polypeptide fragments with a constant glutamic acid at the C-terminal end (with the exception of the true C-terminus of the protein). A constant or constrained C-terminal residue at the end of a small epitope reduces the total possible number of epitopes to be recognized thereby reducing the number of binding molecules needed to analyze the polypeptide fragments and simplifying characterization of a protein sample.

Sample

As noted in the definition and as used herein, "sample" encompasses a variety of sample types and/or origins, such as blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "sample" encompasses a clinical sample, and also includes cells in culture, cell supernatants, cell lysates, serum, plasma, biological fluid, and tissue samples. A sample can be from a microorganism, (e.g., bacteria, yeasts, viruses, viroids), molds, fungi, plants, and animals, including mammals such as humans. A sample may comprise a single cell or more than a single cell. Examples of a sample include blood, plasma, serum, urine, stool, cerebrospinal fluid, synovial fluid, amniotic fluid, saliva, lung lavage, semen, milk, nipple aspirate, prostatic fluid, mucous, cheek swabs, and/or tears.

These samples can be prepared by methods known in the art such as lysing, fractionation, purification, including affinity purification, FACS, laser capture microdissection (LCM) or isopycnic centrifugation. In some embodiments, subcellular fractionation methods are used to create enriched cellular or subcellular fractions, such as subcellular organelles including nuclei, mitochondria, heavy and light membranes and cytoplasm.

In some embodiments, sample preparation comprises labeling proteins or polypeptide fragments in a sample with one or more detectable labels. Labeling may comprise incorporation of a detectable label at the C-terminus, N-terminus, or at one or more internal amino acid residues. Non-limiting examples of labels include biotin, avidin, streptavidin, fluorophors, enzymatic labels, and radiolabels.

Prior to fractionation, e.g., contacting the sample or portions of the sample with a plurality of protein-binding molecules, such as small epitope antibodies or small epitope aptamers, the sample may be treated with one or more agents capable of denaturing and/or solubilizing proteins, such as detergents (ionic and non-ionic), chaotropes and/or reducing agents. Such agents are known in the art.

Under certain circumstances, it may be desirable to remove or minimize abundant proteins present in a sample, for example, by targeted immunodepletion, or other methods known in the art. Generally, such removal (or reduction) occurs prior to fractionation. However, such reduction or removal can occur during or after fractionation.

In some embodiments, it may be desirable to treat the sample with a polysaccharide cleaving agent, for example, to reduce, minimize, and/or eliminate glycosylation of sample protein. Removal of any carbohydrate moieties may be accomplished chemically or enzymatically. Examples of polysaccharide cleaving agents include glycosidases, endoglycosidases, exoglycosylases, and chemicals such as trifluoromethanesulfonic acid. Endoglycosidases such as Endoglycosidase H (New England Biolabs, Beverly, Mass.), and Endo Hf (New England Biolabs) are commercially available. These endoglycosidases cleave the chitobiose core of high mannose and some hybrid oligosaccharides from N-linked glycoproteins. Exoglycosidases are also commercially available from vendors such as New England Biolabs and include, beta-N-Acetylhexosaminidase, alpha-1-2-Fucosidase, alpha-1-3,4 Fucosidase alpha-1-2,3 Mannosidase, alpha-1-6 Mannosidase, Neuraminidase, alpha-2-3 Neuraminidase, beta 1-3 Galactosidase, and alpha-N-Acetylgalactosaminidase The following Examples are provided to illustrate, but not limit, the invention.

EXAMPLES

Example 1

Preparation and Characterization of Small Epitope Antibodies

Five immunization polypeptides in the format of Multiple Antigenic Peptide (MAP) were designed as shown in Table 4. These sequences in combination were also used to evaluate cross-reactivity of the induced antibodies, by virtue of the inclusion in different MAPs of the same sequence in differing locations. Each of the immunization polypeptides was used to immunize 4 Balb/C mice using standard methods.

TABLE 4

Design of immunization polypeptides

| Peptide | Group | Sequence | SEQ ID NO |
|---|---|---|---|
| MAP1 | 1 | Acetylation- HSLFH PEDTGQV KKTTNV -MAP | 6 |
| MAP2 | 2 | Acetylation- PEDTGQV KKTTNV HSLFH -MAP | 7 |
| MAP3 | 3 | Acetylation- LTPKKTTNVLTVP TNIPG -MAP | 8 |
| MAP4 | 4 | Acetylation- LTPKK LTQENQNRGTH IYNQ -MAP | 9 |
| MAP5 | 5 | Acetylation- TIYN TNIPG LTQENQNRGTH -MAP | 10 |

Notes to Table 4:
Polypeptide MAP 1: HSLFHPEDTGQV: From PSA, amino acids #79-89. KKTTNV: From Meningococcal Opa protein, containing KTT, a published 3mer antibody epitope (Malorny, Morelli et al. 1998).
Polypeptide MAP2: Alternate sequences of MAP 1.
Polypeptide MAP3: LTPKK: Motif 1 of PSA (Nagasaki, Watanabe et al. 1999). KKTTNVLTVPTNIPG: From Meningococcal Opa protein, containing two published 3mer antibody epitopes: KTT and NIP and one 4mer epitope: TNIP (Morelli, et al. (1997) Mol Microbiol 25(6): 1047-64.
Polypeptide MAP4: LTPKK: From PSA, the same as in peptide MAP3. LTQENQNRGTH: An immunogenic sequence of alpha-1-ACT selected by DNAStar computer program. IYNQ: From Meningococcal Opa protein, containing a 2mer epitope IY and four amino acids of a 5mer epitope, TIYNQ and of a 7mer epitope TPTIYNQ (Marelli, et al., id.).
Polypeptide MAP5 TIYNTNIPG: From Meningococcal Opa protein (Marelli, et al., id). LTQENQNRGTH: The same as in peptide MAP4.

Notes to Table 4:
Polypeptide MAP1: HSLFHPEDTGQV (SEQ ID NO: 11): From PSA, amino acids #79-89. KKTTNV (SEQ ID NO: 12): From Meningococcal Opa protein, containing KTT, a published 3mer antibody epitope (Malorny, Morelli et al. 1998).

Polypeptide MAP2: Alternate sequences of MAP1.

Polypeptide MAP3: LTPKK (SEQ ID NO: 13): Motif 1 of PSA (Nagasaki, Watanabe et al. 1999). KKTTNVLTVPT-NIPG (SEQ ID NO: 14): From Meningococcal Opa protein, containing two published 3mer antibody epitopes: KTT and NIP and one 4mer epitope: TNIP (SEQ ID NO: 15) (Morelli, et al. (1997) Mol Microbiol 25(6):1047-64.

Polypeptide MAP4: LTPKK (SEQ ID NO: 13): From PSA, the same as in peptide MAP3. LTQENQNRGTH (SEQ ID NO: 16): An immunogenic sequence of alpha-1-ACT selected by DNAStar computer program. IYNQ (SEQ ID NO: 17): From Meningococcal Opa protein, containing a 2mer epitope IY and four amino acids of a 5mer epitope, TIYNQ (SEQ ID NO: 18) and of a 7mer epitope TPTIYNQ (SEQ ID NO: 19) (Marelli, et al., id.). Polypeptide MAP5 TIYNTNIPG (SEQ ID NO: 20): From Meningococcal Opa protein (Marelli, et al., id.). LTQENQNRGTH (SEQ ID NO: 16): The same as in peptide MAP4.

Two sets of screening polypeptides were designed: (1) 5 C-terminally biotinylated with the same sequences as the immunization polypeptides (shown in Table 5); and (2) 43 10mer biotinylated polypeptides with sequences spanning all five immunization polypeptides (shown in Table 6).

TABLE 5

Biotinylated screening polypeptides
(approximately 90% purity)

| Peptide | Mers | Sequence |
|---|---|---|
| Pep1-0 | 18 | Acetylation-HSLFHPEDTGQVKKTTNV-Biotin (SEQ ID NO: 21) |
| Pep2-0 | 18 | Acetylation-PEDTGQVKKTTNVHSLFH-Biotin (SEQ ID NO: 22) |
| Pep3-0 | 18 | Acetylation-LTP<u>KK</u>TTNVLTVPTNIPG-Biotin (SEQ ID NO: 23) |
| Pep4-0 | 20 | Acetylation-LTPKK<u>L</u>TQENQNRGTHIYNQ-Biotin (SEQ ID NO: 24) |
| Pep5-0 | 20 | Acetylation-TIYNTNIPGLTQENQNRGTH-Biotin (SEQ ID NO: 25) |

TABLE 6

Biotinylated mapping polypeptides
(approximately 70% purity)

| Serial number | Peptide name | Sequence | Position in immunization peptides |
|---|---|---|---|
| 1 | Pep1-1 | Acetylated-HSLFHPEDTG-Biotin (SEQ ID NO: 26) | MAP1 1-10 |

TABLE 6-continued

Biotinylated mapping polypeptides
(approximately 70% purity)

| Serial number | Peptide name | Sequence | Position in immunization peptides |
|---|---|---|---|
| 2 | Pep1-2 | Acetylated-SLFHPEDTGQ-Biotin (SEQ ID NO: 27) | MAP1 2-11 |
| 3 | Pep1-3 | Acetylated-LFHPEDTGQV-Biotin (SEQ ID NO: 28) | MAP1 3-12 |
| 4 | Pep1-4 | Acetylated-FHPEDTGQVK-Biotin (SEQ ID NO: 29) | MAP1 4-13 |
| 5 | Pep1-5 | Acetylated-HPEDTGQVKK-Biotin (SEQ ID NO: 30) | MAP1 5-14 |
| 6 | Pep2-1 | Acetylated-PEDTGQVKKT-Biotin (SEQ ID NO: 31) | MAP1 6-15, MAP2 1-10 |
| 7 | Pep2-2 | Acetylated-EDTGQVKKTT-Biotin (SEQ ID NO: 32) | MAP1 7-16, MAP2 2-11 |
| 8 | Pep2-3 | Acetylated-DTGQVKKTTN-Biotin (SEQ ID NO: 33) | MAP1 8-17, MAP2 3-12 |
| 9 | Pep2-4 | Acetylated-TGQVKKTTNV-Biotin (SEQ ID NO: 34) | MAP1 9-18, MAP2 4-13 |
| 10 | Pep2-5 | Acetylated-GQVKKTTNVH-Biotin (SEQ ID NO: 35) | MAP2 5-14 |
| 11 | Pep2-6 | Acetylated-QVKKTTNVHS-Biotin (SEQ ID NO: 36) | MAP2 6-15 |
| 12 | Pep2-7 | Acetylated-VKKTTNVHSL-Biotin (SEQ ID NO: 37) | MAP2 7-16 |
| 13 | Pep2-8 | Acetylated-KKTTNVHSLF-Biotin (SEQ ID NO: 38) | MAP2 8-17 |
| 14 | Pep2-9 | Acetylated-KTTNVHSLFH-Biotin (SEQ ID NO: 39) | MAP2 9-18 |
| 15 | Pep3-1 | Acetylated-LTPKKTTNVL-Biotin (SEQ ID NO: 40) | MAP3 1-10 |
| 16 | Pep3-2 | Acetylated-TPKKTTNVLT-Biotin (SEQ ID NO: 41) | MAP3 2-11 |
| 17 | Pep3-3 | Acetylated-PKKTTNVLTV-Biotin (SEQ ID NO: 42) | MAP3 3-12 |
| 18 | Pep3-4 | Acetylated-KKTTNVLTVP-Biotin (SEQ ID NO: 43) | MAP3 4-13 |
| 19 | Pep3-5 | Acetylated-KTTNVLTVPT-Biotin (SEQ ID NO: 44) | MAP3 5-14 |
| 20 | Pep3-6 | Acetylated-TTNVLTVPTN-Biotin (SEQ ID NO: 45) | MAP3 6-15 |
| 21 | Pep3-7 | Acetylated-TNVLTVPTNI-Biotin (SEQ ID NO: 46) | MAP3 7-16 |
| 22 | Pep3-8 | Acetylated-NVLTVPTNIP-Biotin (SEQ ID NO: 47) | MAP3 8-17 |
| 23 | Pep3-9 | Acetylated-VLTVPTNIPG-Biotin (SEQ ID NO: 48) | MAP3 9-18 |
| 24 | Pep4-1 | Acetylated-LTPKKLTQEN-Biotin (SEQ ID NO: 49) | MAP4 1-10 |
| 25 | Pep4-2 | Acetylated-TPKKLTQENQ-Biotin (SEQ ID NO: 50) | MAP4 2-11 |

TABLE 6-continued

Biotinylated mapping polypeptides
(approximately 70% purity)

| Serial number | Peptide name | Sequence | Position in immunization peptides |
|---|---|---|---|
| 26 | Pep4-3 | Acetylated-PKKLTQENQN-Biotin (SEQ ID NO: 51) | MAP4 3-12 |
| 27 | Pep4-4 | Acetylated-KKLTQENQNR-Biotin (SEQ ID NO: 52) | MAP4 4-13 |
| 28 | Pep4-5 | Acetylated-KLTQENQNRG-Biotin (SEQ ID NO: 53) | MAP4 5-14 |
| 29 | Pep4-6 | Acetylated-LTQENQNRGT-Biotin (SEQ ID NO: 54) | MAP4 6-15, MAP5 10-19 |
| 30 | Pep4-7 | Acetylated-TQENQNRGTH-Biotin (SEQ ID NO: 55) | MAP4 7-16, MAP5 11-20 |
| 31 | Pep4-8 | Acetylated-QENQNRGTHI-Biotin (SEQ ID NO: 56) | MAP4 8-17 |
| 32 | Pep4-9 | Acetylated-ENQNRGTHIY-Biotin (SEQ ID NO: 57) | MAP4 9-18 |
| 33 | Pep4-10 | Acetylated-QENQNRGTHI-Biotin (SEQ ID NO: 56) | MAP4 10-19 |
| 34 | Pep4-11 | Acetylated-ENQNRGTHIY-Biotin (SEQ ID NO: 57) | MAP4 11-20 |
| 35 | Pep5-1 | Acetylated-TIYNTNIPGL-Biotin (SEQ ID NO: 58) | MAP5 1-10 |
| 36 | Pep5-2 | Acetylated-IYNTNIPGLT-Biotin (SEQ ID NO: 59) | MAP5 2-11 |
| 37 | Pep5-3 | Acetylated-YNTNIPGLTQ-Biotin (SEQ ID NO: 60) | MAP5 3-12 |
| 38 | Pep5-4 | Acetylated-NTNIPGLTQE-Biotin (SEQ ID NO: 61) | MAP5 4-13 |
| 39 | Pep5-5 | Acetylated-TNIPGLTQEN-Biotin (SEQ ID NO: 62) | MAP5 5-14 |
| 40 | Pep5-6 | Acetylated-NIPGLTQENQ-Biotin (SEQ ID NO: 63) | MAP5 6-15 |
| 41 | Pep5-7 | Acetylated-IPGLTQENQN-Biotin (SEQ ID NO: 64) | MAP5 7-16 |
| 42 | Pep5-8 | Acetylated-PGLTQENQNR-Biotin (SEQ ID NO: 65) | MAP5 8-17 |
| 43 | Pep5-9 | Acetylated-GLTQENQNRG-Biotin (SEQ ID NO: 66) | MAP5 9-18 |

After a standard period of immunization, immune serum was collected from each mouse using standard methods, and tested using ELISA as follows:

ELISA plates (Corning 3369 or similar) were coated with 100 µl/well or 50 µl/well of streptavidin (Sigma Catalog No. S4762 or similar, 5 µg/ml in 50 mM carbonate buffer, pH 9.6). Plates were incubated at 4° C. overnight or at room temperature for 2 hours. Following incubation, plates were washed 3 times with PBS+0.05% polysorbate surfactant TWEEN-20 (PBST buffer). Following washing, plates were blocked with 250 µl/well of PBST, and incubated at room temperature for 1 hour, or at 4° C. overnight. PBST was removed, and 100 µl/well or 50 µl/well of a test biotinylated polypeptide selected from Table 4, at a concentration of 5 µg/ml (diluted in PBS) was added. Plates were incubated for about 30 to 60 min at room temperature. Following incubation, plates were washed 3 times with PBST. Then, 100 µl or 50 µl/well of test serum (i.e., from test bleeds) was added, and the plates were incubated for one hour at room temperature, or overnight at 4° C. To titer immunoreactivity, the serum was generally diluted prior to testing to 1:500, 1:2000, 1:8000, or 1:32000. Following incubation, plates were washed 3 times with PBST. To detect antibody binding, a 1:10,000 dilution of goat anti-mouse IgG (and IgM)-HRP conjugate (Jackson Immuno order No. 115-036-071, or similar) was added to each well. Plates were incubated at room temperature for another hour, then washed 5 times with PBST. HRP substrate (Sigma Fast OPD) was added and incubated in the dark at room temperature for 30-60 minutes. Plates were read at OD450 with a 96-well colorimetric detector if HRP reaction was not stopped. Alternatively, HRP reaction was stopped with 1.25M sulfuric acid, and plates were read at OD492.

12 test bleeds from Groups 1, 2, and 3 mice were tested. No immune response was observed from mice in groups 1 and 3, and these mice were not studied further. All 4 mice in group 2 showed strong immune response to screening polypeptide Pep2-0 (titers >1:32,000). In addition, immune sera from two of the four mice in group 2 (mice #2-1 and #2-4) showed cross-reactivity with screening polypeptides designed for groups 1 and 3 due to the sequence homology between MAP2 and MAP1/MAP3. These results were consistent with mice #2-1 and #2-4 expressing antibodies that recognize distinct and concise epitopes present within more than one screening antigen used in the ELISA assays. A test of the #2-1 and #2-4 sera versus 23 10mer biotinylated polypeptides that span sequences of all three immunization polypeptides for group 1, 2 and 3 mice also demonstrated a broad cross-reactivity.

Eight test bleeds from groups 4-5 were tested by ELISA. Group 4 mice demonstrated a modest response to their relevant screening polypeptide, Pep4-0, while exhibiting strong cross-reactivity with Pep3-0, the screening polypeptide designed for group 3. Group 4 mice did not show substantial cross-reactivity to Pep5-0 even though there is significant sequence identity between Pep4-0 and Pep5-0. In contrast, 3 of 4 mice in group 5 (mice #5-2, #5-3, #5-4) exhibited robust immunoreactivity to both their screening polypeptide, Pep5-0, and to the related screening polypeptide, Pep4-0. The sera from the responsive mice in group 5 did not demonstrate substantial cross-reactivity to the Pep3-0, even though there is a 5 amino acid block of sequence identity. A test of the #5-2 and #5-3 sera versus 23 10mer biotinylated polypeptides that span sequences of all three immunization polypeptides for group 4 and 5 mice demonstrated two broad but distinctive reaction patterns with the mapping polypeptides spanning sequences of immunization polypeptides for groups 4 and 5 mice.

Group 2, mice #1 and #4, and Group 5, mice #2 and #3, showed the best immune responses, as summarized in Table 7 and FIG. 1. These mice were selected for hybridoma fusions.

TABLE 7

Immunoreactivity and cross-reactivity of selected mice in Groups 2 and 5 to screening polypeptides 1-5.

| Mouse | Peptide 1 | Peptide 2 | Peptide 3 | Peptide 4 | Peptide 5 |
|---|---|---|---|---|---|
| 2-1 | 0.726 | 0.850 | 0.323 | Not tested | Not tested |
| 2-2 | 0.250 | 1.167 | 0.213 | Not tested | Not tested |
| 2-3 | 0.222 | 0.685 | 0.141 | Not tested | Not tested |
| 2-4 | 0.776 | 0.970 | 0.353 | Not tested | Not tested |
| 5-1 | Not tested | Not tested | 0.178 | 0.28 | 0.979 |
| 5-2 | Not tested | Not tested | 0.146 | 1.714 | 1.548 |
| 5-3 | Not tested | Not tested | 0.13 | 1.479 | 1.773 |
| 5-4 | Not tested | Not tested | 0.128 | 1.915 | 1.464 |

The animals were sacrificed, the lymph nodes and spleens harvested, then B cell hybridoma fusions using P3 mouse myeloma cell line as a fusion partner were generated using standard methods. Fusions were plated and incubated for 11-14 days before screening.

In the first round of screening, hybridomas from group 2 and 5 mice were analyzed by ELISA in 96 well plates, essentially as described above, using the corresponding screening polypeptides, 2-0 and 5-0. Following several rounds of screening, 48 positive hybridoma lines were identified and transferred to 24 well plates for expansion and additional characterization including epitope mapping. Of the 48 positive lines, 33 were derived from the Group 2 animals that received the MAP2 immunogen while the remaining 15 originated from the Group 5 animals. Most of the hybridoma lines (~94%) were the fusion products of B cells harvested from the spleen. Thirteen of the 48 hybridoma lines expressed IgG, 25 expressed IgM, and the remaining 10 hybridoma lines were expressing both IgG and IgM or were not expressing either IgG or IgM and were therefore expressing either IgA or IgE.

In the second round of screening, hybridomas selected for expansion were re-tested against the relevant screening polypeptide (either polypeptide 2-0 or polypeptide 5-0). 13 of the 48 hybridomas characterized after the 24 well expansion phase exhibited sequence specific binding to the screening polypeptide 2-0. Other hybridomas bound non-specifically (i.e., bound a variety of oligopeptide sequences), failed to bind (reflecting either a false positive or clonal instability and loss during the transfer and subsequent propagation in 24 well plates) or bound control wells containing BSA.

The 13 hybridomas that specifically bound to screening polypeptide 2-0 were epitope mapped using ELISA as described above, using 3 different sets of 10mer C-terminal biotinylated mapping polypeptides: polypeptides 1-1 to 1-5; 2-1 to 2-9; and 3-1 to 3-9 (see Table 6). 10 of the 12 hybridoma lines exhibited maximum reactivity with a single mapping polypeptide, 2-1, and hybridomas 2.03 and 2.11 showed strong binding to different overlapping sets of mapping polypeptides, polypeptides 2-1 through 2-3 and 2-7 through 2-9. Because these data showed strong reactivity to a single mapping polypeptide for most hybridoma lines, the possibility was considered that steric hindrance associated with immobilization of the mapping polypeptides (specifically, biotin-avidin immobilization) was preventing antibody binding to the epitope present within a cognate series of 10mers, thus potentially biasing the ELISA epitope map results. Thus, epitope specificity using a competitive binding assay was evaluated.

Individual mapping polypeptides were evaluated for their ability to inhibit antibody binding to the 2-0 screening polypeptide affixed to streptavidin-coated 96 well plates. In this format, the 10mer mapping polypeptides were not tethered within the binding pocket of streptavidin and consequently should not be sterically hindered from interacting with a reactive antibody present within the set of 13 hybridomas. Competition experiments were performed using standard methods using the 2-0 screening polypeptide affixed to streptavidin-coated 96 well plates and 10mer mapping polypeptide added to each well.

Using the competitive binding assay, the epitopes recognized by 10 of the 13 hybridomas were determined. Eight of the hybridomas were specific for the epitope PEDTG, (SEQ ID NO: 67)hybridoma 2.03 was specific for epitope DTG and hybridoma 2.11 recognized the epitope KKTTN (SEQ ID NO: 68). Hybridoma 2.31 exhibited a complex inhibition pattern suggesting that this line is a mixture of 2 or more specificities and should be subcloned to segregate the individual reactivities. Finally, hybridomas 1.02 and 2.12 showed poor discrimination in the competitive inhibition assay. The results of this analysis are summarized in Table 8.

TABLE 8

Epitopes Predicted by Competitive Inhibition

Pattern of 1.01, 2.01, 2.04, 2.06, 2.07, 2.08, 2.10 and 2.23: PEDTG

| | | |
|---|---|---|
| P1-1 | HSLFHPEDTG | (SEQ ID NO: 70) |
| P1-2 | SLFHPEDTGQ | (SEQ ID NO: 80) |
| P1-5 | HPEDTGQVKK | (SEQ ID NO: 81) |
| P2-1 | PEDTGQVKKT | (SEQ ID NO: 72) |

2.03 Pattern: DTG

| | | |
|---|---|---|
| P1-1 | HSLFHPEDTG | (SEQ ID NO: 70) |
| P1-2 | SLFHPEDTGQ | (SEQ ID NO: 80) |
| P1-3 | LFHPEDTGQV | (SEQ ID NO: 83) |
| P1-4 | FHPEDTGQVK | (SEQ ID NO: 84) |
| P1-5 | HPEDTGQVKK | (SEQ ID NO: 81) |
| P2-1 | PEDTGQVKKT | (SEQ ID NO: 82) |
| P2-2 | EDTGQVKKTT | (SEQ ID NO: 85) |
| P2-3 | DTGQVKKTTN | (SEQ ID NO: 86) |

2.11 Pattern: KKTTN (SEQ ID NO: 68)

| | | |
|---|---|---|
| P1-4 | FHPEDTGQVK ??? | (SEQ ID NO: 84) |
| P2-3 | DTGQVKKTTN | (SEQ ID NO: 86) |
| P2-4 | TGQVKKTTNV | (SEQ ID NO: 87) |
| P2-5 | GQVKKTTNVH | (SEQ ID NO: 88) |
| P2-6 | QVKKTTNVHS | (SEQ ID NO: 89) |
| P2-7 | VKKTTNVHSL | (SEQ ID NO: 90) |
| P2-8 | | |
| P2-9 | | |

TABLE 8-continued

Epitopes Predicted by Competitive Inhibition

| | | |
|---|---|---|
| P3-1 | LTPKKTTNVL | (SEQ ID NO: 91) |
| P3-2 | TPKKTTNVLT | (SEQ ID NO: 92) |
| P3-3 | PKKTTNVLTV | (SEQ ID NO: 93) |
| P3-4 | KKTTNVLTVP | (SEQ ID NO: 94) |

2.31 Pattern: A mixture of two clones?

| | | |
|---|---|---|
| P1-1 | HSLFHPEDTG | (SEQ ID NO: 70) |
| P1-2 | SLFHPEDTGQ | (SEQ ID NO: 80) |
| P1-5 | HPEDTGQVKK | (SEQ ID NO: 81) |
| P2-1 | PEDTGQVKKT | (SEQ ID NO: 82) |
| P2-7 | VKKTTNVHSL | (SEQ ID NO: 90) |
| P2-8 | KKTTNVHSLF | (SEQ ID NO: 95) |
| P2-9 | KTTNVHSLFH | (SEQ ID NO: 96) |
| P3-2 | TPKKTTNVLT | (SEQ ID NO: 92) |
| P3-3 | PKKTTNVLTV | (SEQ ID NO: 93) |

1.02 and 2.12 Pattern: Pattern is unclear

The competitive binding assays were repeated twice, and it was confirmed that hybridoma 2.11 recognized the epitope KTTN (SEQ ID NO: 69), not the epitope KKTTN (SEQ ID NO: 68) as suggested in the preliminary experiments. The epitope competitive binding assays confirmed the epitope characterization described above for the other hybridomas. The results of this updated analysis are summarized in Table 9.

TABLE 9

Updated and Confirmed Table of Epitopes Predicted by Competitive Inhibition

| Mapping Peptides | | | Maximum Reactivity | |
|---|---|---|---|---|
| | | | 2.03 | 2.11 |
| P1-1 HSLFHPEDTG | | (SEQ ID NO: 70) | 0.382 | 1.476 |
| P1-2 SLFHPEDTGQ | | (SEQ ID NO: 80) | 0.329 | 1.494 |
| P1-5 HPEDTGQVKK | | (SEQ ID NO: 81) | 0.321 | 1.553 |
| P2-1 PEDTGQVKKT | | (SEQ ID NO: 82) | 0.306 | 1.396 |
| P2-2 EDTGQVKKTT | | (SEQ ID NO: 85) | 0.311 | 1.011 |
| P2-3 DTGQVKKTTN | | (SEQ ID NO: 86) | 0.316 | 0.321 |
| P2-4 TGQVKKTTNV | | (SEQ ID NO: 87) | 1.024 | 0.750 |
| P2-5 GQVKKTTNVH | | (SEQ ID NO: 88) | 1.004 | 0.416 |
| P2-6 QVKKTTNVHS | | (SEQ ID NO: 89) | 1.022 | 0.312 |
| P2-7 VKKTTNVHSL | | (SEQ ID NO: 90) | 1.015 | 0.735 |
| P2-8 KKTTNVHSLF | | (SEQ ID NO: 95) | 1.064 | 0.898 |
| P3-1 LTPKKTTNVL | | (SEQ ID NO: 91) | 1.025 | 0.570 |
| P3-2 TPKKTTNVLT | | (SEQ ID NO: 92) | 1.177 | 0.483 |
| P3-4 PKKTTNVLTV | | (SEQ ID NO: 93) | 0.862 | 0.749 |
| P3-5 KKTTNVLTVP | | (SEQ ID NO: 94) | 1.091 | 0.275 |
| P3-6 KTTNVLTVPT | | (SEQ ID NO: 97) | 1.073 | 1.207 |
| P3-7 TTNVLTVPTN | | (SEQ ID NO: 98) | 1.060 | 1.363 |
| P3-8 TNVLTVPTNI | | (SEQ ID NO: 99) | 1.068 | 1.313 |
| P3-8 NVLTVPTNIP | | (SEQ ID NO: 100) | 1.061 | 1.264 |

TABLE 9-continued

Updated and Confirmed Table of Epitopes Predicted by Competitive Inhibition

|  |  |  | Maximum Reactivity | |
|---|---|---|---|---|
| Mapping Peptides |  |  | 2.03 | 2.11 |
| P3-9 | VLTVPTNIPG | (SEQ ID NO: 101) | 1.042 | 1.376 |
| P2-0 | PEDTGQVKKTTNVHSLFH | (SEQ ID NO: 102) | 0.306 | 0.270 |

Example 2

Preparation of Small Epitope Antibodies

An approach to identify antibodies based on phage display antibody screening was performed. Five peptide sequences used for the selection of positive antibodies are shown in Table 10. These sequences in combination were also used to evaluate cross-reactivity of the selected antibodies.

TABLE 10

Design of screening polypeptides

| Peptide | Sequence |
|---|---|
| P1 | CXXXXXDTGXXXXXX (SEQ ID NO: 71) |
| P6 | CXXXXXGEKXXXXXX (SEQ ID NO: 75) |

TABLE 10-continued

Design of screening polypeptides

| Peptide | Sequence |
|---|---|
| P7 | CXXXXXAQVXXXXXX (SEQ ID NO: 72) |
| P8 | CXXXXXIARXXXXXX (SEQ ID NO: 73) |
| P9 | CXXXXXLSHXXXXXX (SEQ ID NO: 74) |

Note to Table 10: The letter 'X' denotes a mixture of the naturally-occurring L-amino acids excluding cysteine, methionine, and tryptophan.

Positives were selected after six rounds of enrichment. The results of phage ELISA screens against the five screening peptides is shown in Table 11. A total of 96 phage were screened for P1; 48 were screened for polypeptides P6-P9. In all cases, positive phage were identified above background.

TABLE 11

Reactivity of enriched phage against screening polypeptides

| Polypeptide 1 | | Polypeptide 6 | | Polypeptide 7 | | Polypeptide 8 | | Polypeptide 9 | |
|---|---|---|---|---|---|---|---|---|---|
| Phage | OD | Phage | OD | Phage | OD | Phage | OD | Phage | OD |
| L50P1_1 | 0.0781 | L50P6_1 | 1.6477 | I50P7_1 | 0.0791 | L50P8_1 | 0.5249 | L50P9_1 | 0.0813 |
| L50P1_2 | 0.0737 | L50P6_2 | 1.6612 | I50P7_2 | 0.3119 | L50P8_2 | 0.4247 | L50P9_2 | 0.4743 |
| L50P1_3 | 0.0684 | L50P6_3 | 1.5365 | I50P7_3 | 0.2111 | L50P8_3 | 0.8174 | L50P9_3 | 0.6882 |
| L50P1_4 | 0.3906 | L50P6_4 | 1.4133 | I50P7_4 | 1.6251 | L50P8_4 | 0.6231 | L50P9_4 | 0.5747 |
| L50P1_5 | 0.3333 | L50P6_5 | 0.9797 | I50P7_5 | 1.3357 | L50P8_5 | 0.5497 | L50P9_5 | 0.4527 |
| L50P1_6 | 0.0667 | L50P6_6 | 0.1036 | I50P7_6 | 0.2128 | L50P8_6 | 0.7834 | L50P9_6 | 0.6045 |
| L50P1_7 | 0.0668 | L50P6_7 | 0.5592 | I50P7_7 | 1.4445 | L50P8_7 | 0.4143 | L50P9_7 | 0.0944 |
| L50P1_8 | 0.0689 | L50P6_8 | 1.5017 | I50P7_8 | 0.0694 | L50P8_8 | 0.8192 | L50P9_8 | 0.0762 |
| L50P1_9 | 0.0714 | L50P6_9 | 1.1022 | I50P7_9 | 0.7113 | L50P8_9 | 0.5725 | L50P9_9 | 0.3449 |
| L50P1_10 | 0.0683 | L50P6_10 | 1.1577 | I50P7_10 | 0.1787 | L50P8_10 | 0.6108 | L50P9_10 | 0.0721 |
| L50P1_11 | 0.0813 | L50P6_11 | 0.4477 | I50P7_11 | 0.1912 | L50P8_11 | 0.2095 | L50P9_11 | 0.6566 |
| L50P1_12 | 0.1168 | L50P6_12 | 1.2041 | I50P7_12 | 0.1158 | L50P8_12 | 0.6757 | L50P9_12 | 0.0831 |
| L50P1_13 | 0.0717 | L50P6_13 | 1.6751 | I50P7_13 | 0.0729 | L50P8_13 | 0.5143 | L50P9_13 | 0.4898 |
| L50P1_14 | 0.4481 | L50P6_14 | 1.1052 | I50P7_14 | 0.1238 | L50P8_14 | 0.659 | L50P9_14 | 0.5458 |
| L50P1_15 | 0.6361 | L50P6_15 | 0.218 | I50P7_15 | 0.0679 | L50P8_15 | 1.0582 | L50P9_15 | 0.0702 |
| L50P1_16 | 0.2818 | L50P6_16 | 0.0787 | I50P7_16 | 0.0688 | L50P8_16 | 0.8478 | L50P9_16 | 0.4297 |
| L50P1_17 | 0.4623 | L50P6_17 | 0.066 | I50P7_17 | 0.0847 | L50P8_17 | 0.7276 | L50P9_17 | 0.3535 |
| L50P1_18 | 0.0614 | L50P6_18 | 0.1961 | I50P7_18 | 1.0256 | L50P8_18 | 0.7266 | L50P9_18 | 0.0757 |
| L50P1_19 | 0.0595 | L50P6_19 | 1.1042 | I50P7_19 | 1.5344 | L50P8_19 | 0.6607 | L50P9_19 | 0.07 |
| L50P1_20 | 0.0821 | L50P6_20 | 0.0618 | I50P7_20 | 0.4507 | L50P8_20 | 0.8016 | L50P9_20 | 0.547 |
| L50P1_21 | 0.08 | L50P6_21 | 1.155 | I50P7_21 | 0.2637 | L50P8_21 | 0.754 | L50P9_21 | 0.5593 |
| L50P1_22 | 0.0632 | L50P6_22 | 1.4566 | I50P7_22 | 0.1088 | L50P8_22 | 0.4702 | L50P9_22 | 0.6068 |
| L50P1_23 | 0.0643 | L50P6_23 | 0.129 | I50P7_23 | 1.0236 | L50P8_23 | 0.3573 | L50P9_23 | 0.5225 |
| L50P1_24 | 0.0817 | L50P6_24 | 1.2605 | I50P7_24 | 0.1236 | L50P8_24 | 0.7595 | L50P9_24 | 0.8072 |
| L50P1_25 | 0.0917 | L50P6_25 | 0.0583 | I50P7_25 | 0.0965 | L50P8_25 | 0.7424 | L50P9_25 | 0.5658 |
| L50P1_26 | 0.0791 | L50P6_26 | 0.0848 | I50P7_26 | 0.898 | L50P8_26 | 0.7334 | L50P9_26 | 0.0758 |
| L50P1_27 | 0.0619 | L50P6_27 | 0.0805 | I50P7_27 | 0.1256 | L50P8_27 | 0.7748 | L50P9_27 | 0.3991 |
| L50P1_28 | 0.4974 | L50P6_28 | 1.5586 | I50P7_28 | 0.7453 | L50P8_28 | 0.6577 | L50P9_28 | 0.5235 |
| L50P1_29 | 0.0596 | L50P6_29 | 0.0778 | I50P7_29 | 0.1149 | L50P8_29 | 0.5632 | L50P9_29 | 0.0699 |
| L50P1_30 | 0.0582 | L50P6_30 | 1.5647 | I50P7_30 | 0.076 | L50P8_30 | 0.5071 | L50P9_30 | 0.516 |
| L50P1_31 | 0.4591 | L50P6_31 | 0.0962 | I50P7_31 | 1.4382 | L50P8_31 | 0.5892 | L50P9_31 | 0.2835 |
| L50P1_32 | 0.0566 | L50P6_32 | 0.0603 | I50P7_32 | 1.5916 | L50P8_32 | 0.6455 | L50P9_32 | 0.0733 |
| L50P1_33 | 0.0622 | L50P6_33 | 0.0815 | I50P7_33 | 0.8539 | L50P8_33 | 0.4008 | L50P9_33 | 0.5253 |

TABLE 11-continued

Reactivity of enriched phage against screening polypeptides

| Polypeptide 1 | | Polypeptide 6 | | Polypeptide 7 | | Polypeptide 8 | | Polypeptide 9 | |
|---|---|---|---|---|---|---|---|---|---|
| Phage | OD | Phage | OD | Phage | OD | Phage | OD | Phage | OD |
| L50P1__34 | 0.0584 | L50P6__34 | 0.1512 | I50P7__34 | 1.0193 | L50P8__34 | 0.4515 | L50P9__34 | 0.5407 |
| L50P1__35 | 0.7212 | L50P6__35 | 0.1344 | I50P7__35 | 0.1178 | L50P8__35 | 0.4302 | L50P9__35 | 0.0744 |
| L50P1__36 | 0.0843 | L50P6__36 | 0.1644 | I50P7__36 | 1.2705 | L50P8__36 | 0.3179 | L50P9__36 | 0.613 |
| L50P1__37 | 0.4181 | L50P6__37 | 1.2164 | I50P7__37 | 0.4899 | L50P8__37 | 0.4526 | L50P9__37 | 0.5239 |
| L50P1__38 | 0.4914 | L50P6__38 | 1.3835 | I50P7__38 | 0.142 | L50P8__38 | 0.7307 | L50P9__38 | 0.1844 |
| L50P1__39 | 0.0607 | L50P6__39 | 0.1062 | I50P7__39 | 0.5033 | L50P8__39 | 0.7737 | L50P9__39 | 0.0804 |
| L50P1__40 | 0.5813 | L50P6__40 | 0.0615 | I50P7__40 | 0.7136 | L50P8__40 | 0.6617 | L50P9__40 | 0.3825 |
| L50P1__41 | 0.3373 | L50P6__41 | 1.3978 | I50P7__41 | 0.2031 | L50P8__41 | 0.6766 | L50P9__41 | 0.0748 |
| L50P1__42 | 0.0561 | L50P6__42 | 0.0758 | I50P7__42 | 0.0669 | L50P8__42 | 0.6741 | L50P9__42 | 0.2942 |
| L50P1__43 | 0.3979 | L50P6__43 | 0.0831 | I50P7__43 | 0.1266 | L50P8__43 | 0.6942 | L50P9__43 | 0.0707 |
| L50P1__44 | 0.0587 | L50P6__44 | 1.5906 | I50P7__44 | 0.0693 | L50P8__44 | 0.6275 | L50P9__44 | 0.0722 |
| L50P1__45 | 0.0576 | L50P6__45 | 0.081 | I50P7__45 | 0.1209 | L50P8__45 | 0.3312 | L50P9__45 | 0.5045 |
| L50P1__46 | 0.0699 | L50P6__46 | 1.4628 | I50P7__46 | 0.4689 | L50P8__46 | 0.3838 | L50P9__46 | 0.2859 |
| L50P1__47 | 0.4785 | L50P6__47 | 0.1462 | I50P7__47 | 0.0686 | L50P8__47 | 0.3922 | L50P9__47 | 0.4253 |
| L50P1__48 | 0.6597 | L50P6__48 | 0.0738 | Neg Control | 0.0634 | L50P8__48 | 0.5962 | Neg Control | 0.1297 |
| Neg Control | 0.0738 | Neg Control | 0.1297 | | | Neg Control | 0.1297 | | |

Figure 2:
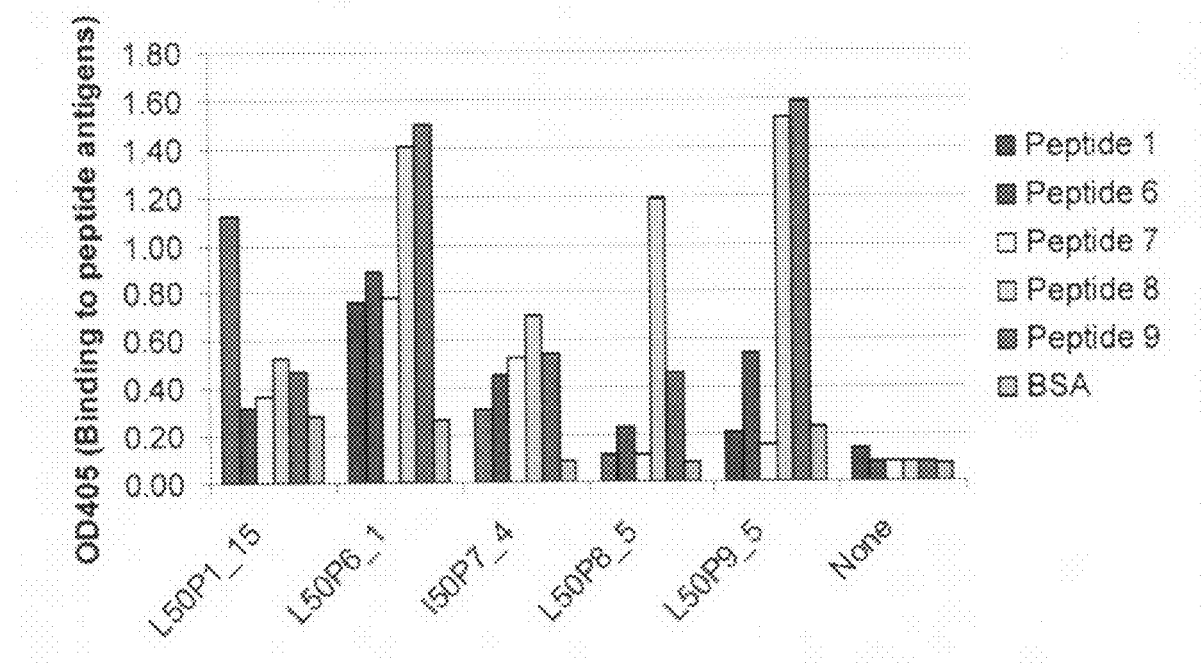
FIG. 2 shows the results of a secondary screen of positive antibodies in a phage ELISA, as described in Example 2.

In a secondary screen of positives identified in the primary screen, a phage ELISA assay was done against all five polypeptides. Up to five positives were selected for the secondary screen. FIG. 2 shows the results of the most selective clones using this assay. All five positives yielded significant signal to polypeptide above BSA, and the phage selected from P1 (L50P1__15), P8 (L50P8__5), and P9 (L50P9__5) appear to show specificity in this semi-quantitative assay.

Figure 3:
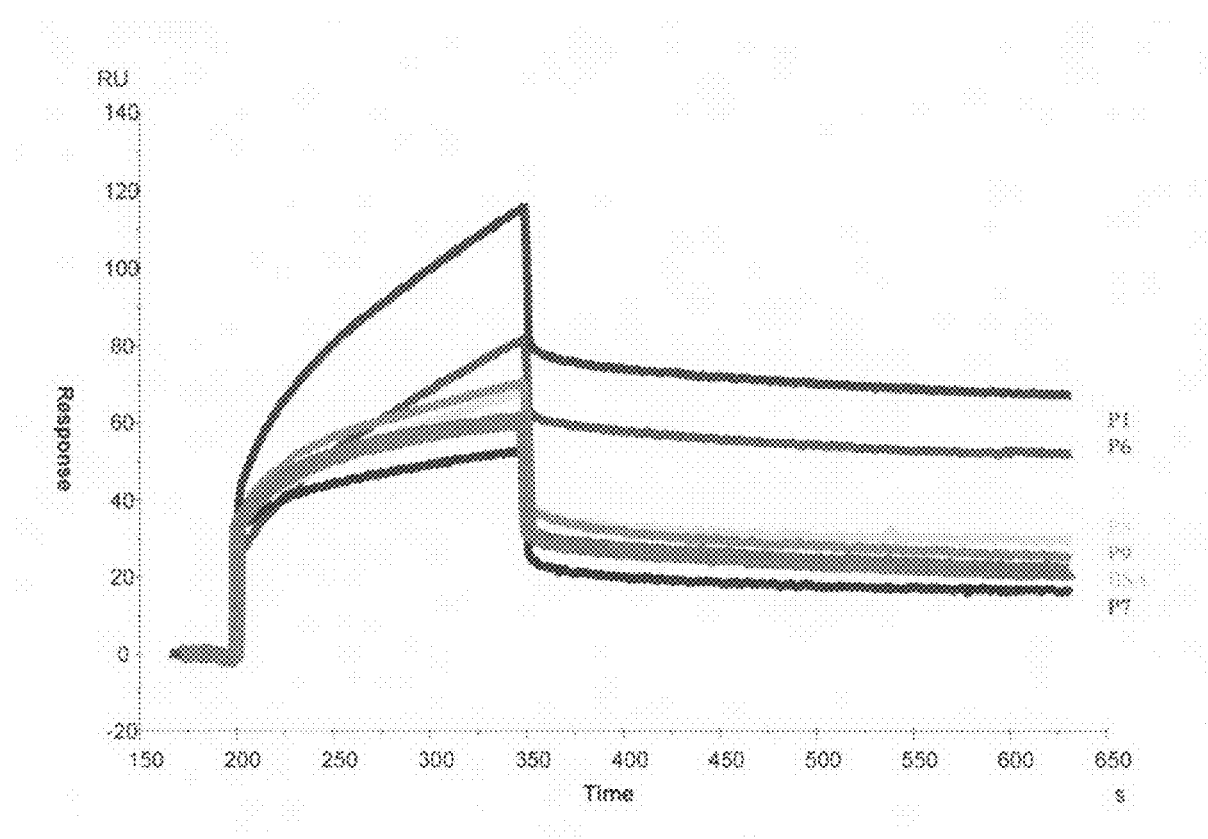
FIG. 3 shows an SPR trace of a single chain antibody derived from phage L50P1__15 against peptides 1, 6, 7, 8, and 9, as described in Example 2.
Figure 4:
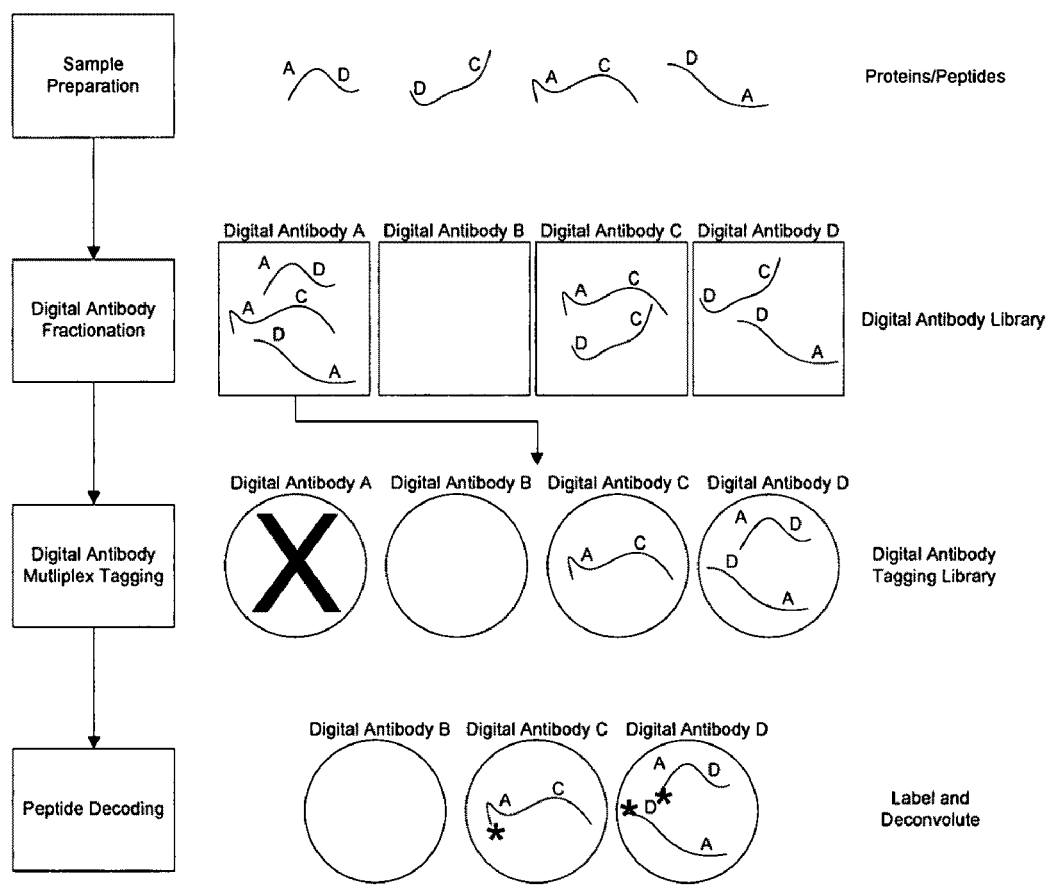
FIG. 4 schematically depicts an embodiment of a procedure for fractionation of proteins in two dimensions and detection of proteins in fractions generated in the second dimension fractionation, as described herein.

The reactive antibody for L50P1__15 was subcloned into a vector for bacterial expression of single chain antibodies. The crude periplasmic preparation was analyzed using a surface plasmon resonance (SPR) biosensor assay to monitor the formation of complex association and the dissociation of the protein from immobilized peptides (Malmborg et al, 1995). FIG. 3 shows the SPR profile of single chain antibody against the five polypeptides and BSA. The antibody has the highest affinity for peptide 1, with an estimated $K_d$ of $2 \times 10^{-8}$.

Example 3

Protein Profiling and Biomarker Development

In one exemplary method for protein profiling, serum samples derived from healthy and affected individuals for a particular disease of clinical interest are subjected to: (a) debulking of the most abundant protein constituents; (b) deglycosylation of the less abundant proteins that remain; (c) reduction and alkylation of cysteine residues present in the debulked proteome; (d) digestion of the debulked proteome to completion; (e) fractionation of the resulting peptide fragments with small epitope antibodies as described above; and (f) comparison of the composition and relative abundance of peptide constituents from epitope enriched fractions derived from healthy and affected patients to identify candidate biomarkers associated with a specific disease.

Multiplex fractionation with small epitope antibodies is performed as described herein in parallel with samples from healthy and affected individuals with two sets of approximately 100 small epitope antibodies of different specificities. Each antibody is chosen based on a set of criteria including epitope size, epitope abundance in the serum proteome, specificity, affinity, and sampling redundancy. The epitopes recognized by the antibodies are predominantly 3mers, although some are 4mers or 5mers that satisfy the abundance criteria, with each epitope occurring in 0.5-3% of the constituents of the serum proteome. Each antibody recognizes its cognate epitope in a context-independent manner and with high affinity. The complete set of small epitope antibodies used for fractionation provides 3-5 fold sampling redundancy to accommodate the variability expected in both expression levels for different proteins and capture efficiencies for each antibody in the set.

Mass spectroscopy is used to analyze the peptide composition and peptide constituent expression levels for each small epitope antibody fraction. Biomarkers are identified that are differentially expressed in healthy and diseased individuals. ELISA assays are developed that can discriminate between healthy and affected individuals based on specific levels of identified biomarkers present in plasma or serum.

Example 4

Identification of a Protein in a Fraction Produced by Multiplex Fractionation

The reactivity of protein or peptide species with small epitope antibodies can be employed in multiplex fractionation to identify a specific protein or subset of proteins in a protein-containing sample.

A first fractionation with small epitope antibodies that bind to known epitopes is performed. Proteins that bind to a specific small epitope antibody ("first small epitope antibody") contain the known epitope recognized by the first small epitope antibody. A second fractionation of the proteins bound to the first small epitope antibody is performed with small epitope antibodies that recognize different known epitopes than the first small epitope antibody. A protein bound to a small epitope antibody ("second small epitope antibody") in the second fractionation contains known epitopes recognized by both the first small epitope antibody and the second small epitope antibody.

If a library of small epitope antibodies each has a 5% chance of reacting with any protein in a sample, double fractionation provides a 0.25% chance that the bound species is a unique protein. If there are 10,000 proteins in the original sample, a protein bound by two such antibodies is one of 25 possibilities. If the library contains small epitope antibodies that each have a 1% chance of reacting with a protein, double fractionation provides a 0.01% chance that the bound protein is unique and if there are 10,000 proteins in the original sample, a protein bound by two such antibodies is unique.

After identification of both first dimensional reactivity (first epitope identification) and second dimensional reactivity (second epitope identification) for a protein fractionated as described above, the amino acid sequences of the bound epitopes are compared to a table of all known proteins in the organism from which the sample was derived, and one or more proteins containing these epitope sequences is identified. In some embodiments, determination of the identity of the protein is not necessary, since knowing that a protein is one of a few possibilities is sufficient to permit rapid assessment of the importance of a few proteins relative to the original complex sample.

Example 5

Identification of a Protein in a Fraction Using Antibodies to C-Terminus Epitopes As described in example 4, the reactivity of protein or peptide species with small epitope antibodies can be employed in multiplex fractionation to identify a specific protein or subset of proteins in a protein-containing sample. To reduce the number of binding molecules necessary for characterization and/or to increase information identifying the protein(s) in a sample, a protein cleavage step is included as well as the use of antibodies directed to C-terminal epitopes.

A protein sample is incubated with Staphylococcal V8 protease for a period of time resulting in cleavage of the proteins at glutamic acid residues, preferably without nonspecific cleavage at any other residues, resulting in protease cleavage products containing glutamic acid residues at their C-terminal ends. The Staphylococcal V8 protease is removed from the protein sample and the mixture of polypeptide fragments is fractionated.

A first fractionation with small epitope antibodies that bind to known C-terminal epitopes is performed. A polypeptide fragment that binds to a first small epitope antibody contains the known C-terminal epitope recognized by the first small epitope antibody. A second fractionation of the polypeptide fragments bound to the first small epitope antibody is performed with small epitope antibodies that recognize internal epitopes, different than the epitopes recognized by the first small epitope antibodies. A polypeptide fragment bound to a second small epitope antibody in the second fractionation contains known epitopes recognized by both the first C-terminal small epitope antibody and the second internal small epitope antibody.

After identification of both first dimensional reactivity (first C-terminal epitope identification) and second dimensional reactivity (second internal epitope identification) for a protein sample fractionated as described above, the amino acid sequences of the small epitopes recognized by the first and second small epitope antibodies for each bound polypeptide fragment are compared to a database of all known proteins in the organism from which the sample was derived, and one or more proteins containing these sequences is identified. In some embodiments, determination of the identity of the protein is not necessary, since knowing that a protein is one of a few possibilities is sometimes sufficient to permit rapid assessment of the importance of a few proteins relative to the original complex sample.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for characterizing protein in a sample that comprises a mixture of proteins, said method comprising:
   (a) contacting protein in said sample with a protein cleaving agent, wherein said protein cleaving agent cleaves at a cleavage site to produce a set of polypeptide fragments comprising a C-terminal amino acid at said cleavage site; and wherein said polypeptide fragments comprise internal small epitopes;
   (b) fractionating said polypeptide fragments into fractions with a plurality of first protein-binding molecules wherein said first protein-binding molecules bind to small epitopes comprising said C-terminal amino acid;
   (c) contacting polypeptide fragments in at least one of said fractions with a plurality of second protein-binding molecules wherein said second protein-binding molecules bind to said internal epitopes; and
   (d) detecting protein bound to said second protein-binding molecules.

2. A method according to claim 1, wherein each of said second protein-binding molecules comprises a unique detectable label, and wherein the method comprises detecting the unique detectable labels.

3. A method according to claim 1, wherein said small epitope comprising a C-terminal amino acid consists of 3 to 5 amino acids.

4. A method according to claim 1, wherein said internal epitopes consist of 3 to 5 amino acids.

5. A method for characterizing protein in a sample that comprises a mixture of proteins, said method comprising:
   (a) contacting protein in the sample with a protein cleaving agent wherein said protein cleaving agent cleaves at a cleavage site to produce a set of polypeptide fragments comprising a C-terminal amino acid at said cleavage site;
   (b) contacting protein with a plurality of protein-binding molecules wherein said protein-binding molecules bind to small epitopes comprising said C-terminal amino acid;
   (c) detecting unbound protein.

6. A method according to claim 5, wherein said protein bound to said protein-binding molecules is separated from said unbound protein prior to detection.

7. A method according to claim 5, wherein said protein comprises a detectable label, and wherein the method comprises detecting the label in said unbound protein.

8. A method according to claim 5, wherein said protein-binding molecules comprise small epitope antibodies.

9. A method according to claim 5, wherein said protein-binding molecules comprise small epitope aptamers.

* * * * *

SEQUENCE LISTING

```
<160> NUMBER OF SEQ ID NOS: 102

<210> SEQ ID NO 1
<211> LENGTH: 4
<212> TYPE: PRT
<213> ORGANISM: Neisseria meningitidis
<220> FEATURE:
<223> OTHER INFORMATION: Opa proteins

<400> SEQUENCE: 1

Asn Arg Gln Asp
1

<210> SEQ ID NO 2
<211> LENGTH: 4
<212> TYPE: PRT
<213> ORGANISM: Neisseria meningitidis
<220> FEATURE:
<223> OTHER INFORMATION: Opa proteins

<400> SEQUENCE: 2

Thr Thr Phe Leu
1
```

-continued

```
<210> SEQ ID NO 3
<211> LENGTH: 4
<212> TYPE: PRT
<213> ORGANISM: Porcine
<220> FEATURE:
<223> OTHER INFORMATION: ZP3 beta

<400> SEQUENCE: 3

Trp Gln Asp Glu
 1

<210> SEQ ID NO 4
<211> LENGTH: 4
<212> TYPE: PRT
<213> ORGANISM: Human immunodeficiency virus
<220> FEATURE:
<223> OTHER INFORMATION: Gp120

<400> SEQUENCE: 4

Gly Pro Gly Arg
 1

<210> SEQ ID NO 5
<211> LENGTH: 4
<212> TYPE: PRT
<213> ORGANISM: Crotalus terrificus
<220> FEATURE:
<221> NAME/KEY: VARIANT
<222> LOCATION: 1
<223> OTHER INFORMATION: Xaa = Asp or Ser
<220> FEATURE:
<221> NAME/KEY: VARIANT
<222> LOCATION: 4
<223> OTHER INFORMATION: Xaa = Ala or Gly

<400> SEQUENCE: 5

Xaa Gly Tyr Xaa
 1

<210> SEQ ID NO 6
<211> LENGTH: 18
<212> TYPE: PRT
<213> ORGANISM: Artificial Sequence
<220> FEATURE:
<223> OTHER INFORMATION: Combination of Homo sapiens and Neisseria
      meningitidis opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 18
<223> OTHER INFORMATION: C-terminal residue is attached to MAP.

<400> SEQUENCE: 6

His Ser Leu Phe His Pro Glu Asp Thr Gly Gln Val Lys Lys Thr Thr
 1               5                  10                  15

Asn Val

<210> SEQ ID NO 7
<211> LENGTH: 18
<212> TYPE: PRT
<213> ORGANISM: Artificial Sequence
<220> FEATURE:
<223> OTHER INFORMATION: Combination of PSA, Homo sapiens, and Neisseria
      meningitidis opa proteins
<220> FEATURE:
<221> NAME/KEY: VARIANT
<222> LOCATION: 1
```

-continued

<223> OTHER INFORMATION: N-terminal residue is acetylated.
<220> FEATURE:
<221> NAME/KEY: VARIANT
<222> LOCATION: 18
<223> OTHER INFORMATION: C-terminal residue is attached to MAP.

<400> SEQUENCE: 7

Pro Glu Asp Thr Gly Gln Val Lys Lys Thr Thr Asn Val His Ser Leu
 1               5                  10                  15

Phe His

<210> SEQ ID NO 8
<211> LENGTH: 18
<212> TYPE: PRT
<213> ORGANISM: Artificial Sequence
<220> FEATURE:
<223> OTHER INFORMATION: Combination of Homo sapiens and Neisseria
      meningitidis opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 18
<223> OTHER INFORMATION: C-terminal residue is attached to MAP.

<400> SEQUENCE: 8

Leu Thr Pro Lys Lys Thr Thr Asn Val Leu Thr Val Pro Thr Asn Ile
 1               5                  10                  15

Pro Gly

<210> SEQ ID NO 9
<211> LENGTH: 20
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 20
<223> OTHER INFORMATION: C-terminal residue is attached to MAP.

<400> SEQUENCE: 9

Leu Thr Pro Lys Lys Leu Thr Gln Glu Asn Gln Asn Arg Gly Thr His
 1               5                  10                  15

Ile Tyr Asn Gln
            20

<210> SEQ ID NO 10
<211> LENGTH: 20
<212> TYPE: PRT
<213> ORGANISM: Artificial Sequence
<220> FEATURE:
<223> OTHER INFORMATION: Combination of Neisseria meningitidis opa
      proteins, ACT, Homo sapiens
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 20
<223> OTHER INFORMATION: C-terminal residue is attached to MAP.

<400> SEQUENCE: 10

Thr Ile Tyr Asn Thr Asn Ile Pro Gly Leu Thr Gln Glu Asn Gln Asn
1               5                   10                  15

Arg Gly Thr His
            20

<210> SEQ ID NO 11
<211> LENGTH: 12
<212> TYPE: PRT
<213> ORGANISM: Homo sapiens

<400> SEQUENCE: 11

His Ser Leu Phe His Pro Glu Asp Thr Gly Gln Val
1               5                   10

<210> SEQ ID NO 12
<211> LENGTH: 6
<212> TYPE: PRT
<213> ORGANISM: Neisseria meningitidis
<220> FEATURE:
<223> OTHER INFORMATION: Opa proteins

<400> SEQUENCE: 12

Lys Lys Thr Thr Asn Val
1               5

<210> SEQ ID NO 13
<211> LENGTH: 5
<212> TYPE: PRT
<213> ORGANISM: Artificial Sequence
<220> FEATURE:
<223> OTHER INFORMATION: Combination of Homo sapiens and PSA

<400> SEQUENCE: 13

Leu Thr Pro Lys Lys
1               5

<210> SEQ ID NO 14
<211> LENGTH: 15
<212> TYPE: PRT
<213> ORGANISM: Neisseria meningitidis
<220> FEATURE:
<223> OTHER INFORMATION: Opa proteins

<400> SEQUENCE: 14

Lys Lys Thr Thr Asn Val Leu Thr Val Pro Thr Asn Ile Pro Gly
1               5                   10                  15

<210> SEQ ID NO 15
<211> LENGTH: 4
<212> TYPE: PRT
<213> ORGANISM: Neisseria meningitidis
<220> FEATURE:
<223> OTHER INFORMATION: Opa proteins

<400> SEQUENCE: 15

Thr Asn Ile Pro
1

<210> SEQ ID NO 16
<211> LENGTH: 11
<212> TYPE: PRT
<213> ORGANISM: Homo sapiens

<400> SEQUENCE: 16

Leu Thr Gln Glu Asn Gln Asn Arg Gly Thr His
1               5                   10

```
<210> SEQ ID NO 17
<211> LENGTH: 4
<212> TYPE: PRT
<213> ORGANISM: Neisseria meningitidis
<220> FEATURE:
<223> OTHER INFORMATION: Opa proteins

<400> SEQUENCE: 17

Ile Tyr Asn Gln
 1

<210> SEQ ID NO 18
<211> LENGTH: 5
<212> TYPE: PRT
<213> ORGANISM: Neisseria meningitidis
<220> FEATURE:
<223> OTHER INFORMATION: Opa proteins

<400> SEQUENCE: 18

Thr Ile Tyr Asn Gln
 1               5

<210> SEQ ID NO 19
<211> LENGTH: 7
<212> TYPE: PRT
<213> ORGANISM: Neisseria meningitidis
<220> FEATURE:
<223> OTHER INFORMATION: Opa proteins

<400> SEQUENCE: 19

Thr Pro Thr Ile Tyr Asn Gln
 1               5

<210> SEQ ID NO 20
<211> LENGTH: 9
<212> TYPE: PRT
<213> ORGANISM: Neisseria meningitidis
<220> FEATURE:
<223> OTHER INFORMATION: Opa proteins

<400> SEQUENCE: 20

Thr Ile Tyr Asn Thr Asn Ile Pro Gly
 1               5

<210> SEQ ID NO 21
<211> LENGTH: 18
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 18
<223> OTHER INFORMATION: C-terminal residue is biotinylated.

<400> SEQUENCE: 21

His Ser Leu Phe His Pro Glu Asp Thr Gly Gln Val Lys Lys Thr Thr
 1               5                  10                  15

Asn Val

<210> SEQ ID NO 22
<211> LENGTH: 18
<212> TYPE: PRT
<213> ORGANISM: Neisseria meningitidis
```

```
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 18
<223> OTHER INFORMATION: C-terminal residue is biotinylated.

<400> SEQUENCE: 22

Pro Glu Asp Thr Gly Gln Val Lys Lys Thr Thr Asn Val His Ser Leu
 1               5                  10                  15

Phe His

<210> SEQ ID NO 23
<211> LENGTH: 18
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 18
<223> OTHER INFORMATION: C-terminal residue is biotinylated.

<400> SEQUENCE: 23

Leu Thr Pro Lys Lys Thr Thr Asn Val Leu Thr Val Pro Thr Asn Ile
 1               5                  10                  15

Pro Gly

<210> SEQ ID NO 24
<211> LENGTH: 20
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 20
<223> OTHER INFORMATION: C-terminal residue is biotinylated.

<400> SEQUENCE: 24

Leu Thr Pro Lys Lys Leu Thr Gln Glu Asn Gln Asn Arg Gly Thr His
 1               5                  10                  15

Ile Tyr Asn Gln
             20

<210> SEQ ID NO 25
<211> LENGTH: 20
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 20
<223> OTHER INFORMATION: C-terminal residue is biotinylated.
```

<400> SEQUENCE: 25

Thr Ile Tyr Asn Thr Asn Ile Pro Gly Leu Thr Gln Glu Asn Gln Asn
1               5                   10                  15

Arg Gly Thr His
            20

<210> SEQ ID NO 26
<211> LENGTH: 10
<212> TYPE: PRT
<213> ORGANISM: Artificial Sequence
<220> FEATURE:
<223> OTHER INFORMATION: Combination of Homo sapiens and PSA
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 26

His Ser Leu Phe His Pro Glu Asp Thr Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Combination of Homo sapiens and PSA
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 27

Ser Leu Phe His Pro Glu Asp Thr Gly Gln
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Combination of Homo sapiens and PSA
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 28

Leu Phe His Pro Glu Asp Thr Gly Gln Val
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.

```
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 29

Phe His Pro Glu Asp Thr Gly Gln Val Lys
 1               5                   10

<210> SEQ ID NO 30
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 30

His Pro Glu Asp Thr Gly Gln Val Lys Lys
 1               5                   10

<210> SEQ ID NO 31
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 31

Pro Glu Asp Thr Gly Gln Val Lys Lys Thr
 1               5                   10

<210> SEQ ID NO 32
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 32

Glu Asp Thr Gly Gln Val Lys Lys Thr Thr
 1               5                   10
```

-continued

```
<210> SEQ ID NO 33
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 33

Asp Thr Gly Gln Val Lys Lys Thr Thr Asn
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 34

Thr Gly Gln Val Lys Lys Thr Thr Asn Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 35

Gly Gln Val Lys Lys Thr Thr Asn Val His
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
```

```
<222> LOCATION: 10
<223> OTHER INFORMATION: C-terminal residue is biotinylated.

<400> SEQUENCE: 36

Gln Val Lys Lys Thr Thr Asn Val His Ser
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 37

Val Lys Lys Thr Thr Asn Val His Ser Leu
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 38

Lys Lys Thr Thr Asn Val His Ser Leu Phe
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 39

Lys Thr Thr Asn Val His Ser Leu Phe His
 1               5                  10

<210> SEQ ID NO 40
<211> LENGTH: 10
<212> TYPE: PRT
<213> ORGANISM: Artificial Sequence
<220> FEATURE:
```

-continued

```
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminated residue is biotinylated.

<400> SEQUENCE: 40

Leu Thr Pro Lys Lys Thr Thr Asn Val Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 41

Thr Pro Lys Lys Thr Thr Asn Val Leu Thr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Combination of Homo sapiens, PSA, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 42

Pro Lys Lys Thr Thr Asn Val Leu Thr Val
1               5                   10

<210> SEQ ID NO 43
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated

<400> SEQUENCE: 43

Lys Lys Thr Thr Asn Val Leu Thr Val Pro
1               5                   10
```

```
<210> SEQ ID NO 44
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 44

Lys Thr Thr Asn Val Leu Thr Val Pro Thr
 1               5                  10

<210> SEQ ID NO 45
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 45

Thr Thr Asn Val Leu Thr Val Pro Thr Asn
 1               5                  10

<210> SEQ ID NO 46
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 46

Thr Asn Val Leu Thr Val Pro Thr Asn Ile
 1               5                  10

<210> SEQ ID NO 47
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.
```

```
<400> SEQUENCE: 47

Asn Val Leu Thr Val Pro Thr Asn Ile Pro
 1               5                  10

<210> SEQ ID NO 48
<211> LENGTH: 10
<212> TYPE: PRT
<213> ORGANISM: Neisseria meningitidis
<220> FEATURE:
<223> OTHER INFORMATION: Opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 48

Val Leu Thr Val Pro Thr Asn Ile Pro Gly
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 49

Leu Thr Pro Lys Lys Leu Thr Gln Glu Asn
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 50

Thr Pro Lys Lys Leu Thr Gln Glu Asn Gln
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
```

-continued

```
<221> NAME/KEY: VARIANT
<222> LOCATION: 10
<223> OTHER INFORMATION: C-terminal residue is biotinylated.

<400> SEQUENCE: 51

Pro Lys Lys Leu Thr Gln Glu Asn Gln Asn
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 52

Lys Lys Leu Thr Gln Glu Asn Gln Asn Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Combination of Homo sapiens, PSA, and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 53

Lys Leu Thr Gln Glu Asn Gln Asn Arg Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Combination of Homo sapiens and ACT
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 54

Leu Thr Gln Glu Asn Gln Asn Arg Gly Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Combination of Homo sapiens and ACT
<220> FEATURE:
```

```
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 55

Thr Gln Glu Asn Gln Asn Arg Gly Thr His
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 56

Gln Glu Asn Gln Asn Arg Gly Thr His Ile
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 57

Glu Asn Gln Asn Arg Gly Thr His Ile Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 58

Thr Ile Tyr Asn Thr Asn Ile Pro Gly Leu
1               5                   10
```

```
<210> SEQ ID NO 59
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 59

Ile Tyr Asn Thr Asn Ile Pro Gly Leu Thr
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 60

Tyr Asn Thr Asn Ile Pro Gly Leu Thr Gln
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 61

Asn Thr Asn Ile Pro Gly Leu Thr Gln Glu
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
```

```
<223> OTHER INFORMATION: C-terminal residue is biotinylated.

<400> SEQUENCE: 62

Thr Asn Ile Pro Gly Leu Thr Gln Glu Asn
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 63

Asn Ile Pro Gly Leu Thr Gln Glu Asn Gln
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 64

Ile Pro Gly Leu Thr Gln Glu Asn Gln Asn
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
      meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 65

Pro Gly Leu Thr Gln Glu Asn Gln Asn Arg
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Combination of Homo sapiens, ACT, and Neisseria
```

```
                meningitidis opa proteins.
<220> FEATURE:
<221> NAME/KEY: VARIANT
<222> LOCATION: 1
<223> OTHER INFORMATION: N-terminal residue is acetylated.
<220> FEATURE:
<221> NAME/KEY: VARIANT
<222> LOCATION: 10
<223> OTHER INFORMATION: C-terminal residue is biotinylated.

<400> SEQUENCE: 66

Gly Leu Thr Gln Glu Asn Gln Asn Arg Gly
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Combination of Homo sapiens and PSA

<400> SEQUENCE: 67

Pro Glu Asp Thr Gly
1               5

<210> SEQ ID NO 68
<211> LENGTH: 5
<212> TYPE: PRT
<213> ORGANISM: Neisseria meningitidis
<220> FEATURE:
<223> OTHER INFORMATION: Opa proteins

<400> SEQUENCE: 68

Lys Lys Thr Thr Asn
1               5

<210> SEQ ID NO 69
<211> LENGTH: 4
<212> TYPE: PRT
<213> ORGANISM: Neisseria meningitidis
<220> FEATURE:
<223> OTHER INFORMATION: Opa proteins

<400> SEQUENCE: 69

Lys Thr Thr Asn
1

<210> SEQ ID NO 70
<211> LENGTH: 10
<212> TYPE: PRT
<213> ORGANISM: Artificial Sequence
<220> FEATURE:
<223> OTHER INFORMATION: Combination of Homo sapiens and PSA

<400> SEQUENCE: 70

His Ser Leu Phe His Pro Glu Asp Thr Gly
1               5                   10

<210> SEQ ID NO 71
<211> LENGTH: 15
<212> TYPE: PRT
<213> ORGANISM: Artificial Sequence
<220> FEATURE:
<223> OTHER INFORMATION: Synthetized peptide sequence
<220> FEATURE:
<221> NAME/KEY: VARIANT
<222> LOCATION: 2-6, 10-15
<223> OTHER INFORMATION: Xaa = Any Amino Acid (excluding cysteine,
      methionine, and trytophan).
```

```
<400> SEQUENCE: 71

Cys Xaa Xaa Xaa Xaa Xaa Asp Thr Gly Xaa Xaa Xaa Xaa Xaa Xaa
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetized peptide sequence
<220> FEATURE:
<221> NAME/KEY: VARIANT
<222> LOCATION: 2-6, 10-15
<223> OTHER INFORMATION: Xaa = Any Amino Acid (excluding cysteine,
      methionine, and trytophan).

<400> SEQUENCE: 72

Cys Xaa Xaa Xaa Xaa Xaa Ala Gln Val Xaa Xaa Xaa Xaa Xaa Xaa
 1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetized peptide sequence
<220> FEATURE:
<221> NAME/KEY: VARIANT
<222> LOCATION: 2-6, 10-15
<223> OTHER INFORMATION: Xaa = Any Amino Acid (excluding cysteine,
      methionine, and trytophan).

<400> SEQUENCE: 73

Cys Xaa Xaa Xaa Xaa Xaa Ile Ala Arg Xaa Xaa Xaa Xaa Xaa Xaa
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: Synthesized peptide sequence
<220> FEATURE:
<221> NAME/KEY: VARIANT
<222> LOCATION: 2-6, 10-15
<223> OTHER INFORMATION: Xaa = Any Amino Acid (excluding cysteine,
      methionine, and trytophan).

<400> SEQUENCE: 74

Cys Xaa Xaa Xaa Xaa Xaa Leu Ser His Xaa Xaa Xaa Xaa Xaa Xaa
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Synthesized peptide sequence
<220> FEATURE:
<221> NAME/KEY: VARIANT
<222> LOCATION: 2-6, 10-15
<223> OTHER INFORMATION: Xaa = Any Amino Acid (excluding cysteine,
      methionine, and trytophan).

<400> SEQUENCE: 75

Cys Xaa Xaa Xaa Xaa Xaa Gly Glu Lys Xaa Xaa Xaa Xaa Xaa Xaa
 1               5                  10                  15

<210> SEQ ID NO 76
<211> LENGTH: 4
```

```
<212> TYPE: PRT
<213> ORGANISM: Crotalus terrificus

<400> SEQUENCE: 76

Asp Gly Tyr Ala
 1

<210> SEQ ID NO 77
<211> LENGTH: 4
<212> TYPE: PRT
<213> ORGANISM: Crotalus terrificus

<400> SEQUENCE: 77

Asp Gly Tyr Gly
 1

<210> SEQ ID NO 78
<211> LENGTH: 4
<212> TYPE: PRT
<213> ORGANISM: Crotalus terrificus

<400> SEQUENCE: 78

Ser Gly Tyr Ala
 1

<210> SEQ ID NO 79
<211> LENGTH: 4
<212> TYPE: PRT
<213> ORGANISM: Crotalus terrificus

<400> SEQUENCE: 79

Ser Gly Tyr Gly
 1

<210> SEQ ID NO 80
<211> LENGTH: 10
<212> TYPE: PRT
<213> ORGANISM: Artificial Sequence
<220> FEATURE:
<223> OTHER INFORMATION: Synthetic peptide

<400> SEQUENCE: 80

Ser Leu Phe His Pro Glu Asp Thr Gly Gln
 1               5                  10

<210> SEQ ID NO 81
<211> LENGTH: 10
<212> TYPE: PRT
<213> ORGANISM: Artificial Sequence
<220> FEATURE:
<223> OTHER INFORMATION: Synthetic peptide

<400> SEQUENCE: 81

His Pro Glu Asp Thr Gly Gln Val Lys Lys
 1               5                  10

<210> SEQ ID NO 82
<211> LENGTH: 10
<212> TYPE: PRT
<213> ORGANISM: Artificial Sequence
<220> FEATURE:
<223> OTHER INFORMATION: Synthetic peptide

<400> SEQUENCE: 82

Pro Glu Asp Thr Gly Gln Val Lys Lys Thr
 1               5                  10
```

```
<210> SEQ ID NO 83
<211> LENGTH: 10
<212> TYPE: PRT
<213> ORGANISM: Artificial Sequence
<220> FEATURE:
<223> OTHER INFORMATION: Synthetic peptide

<400> SEQUENCE: 83

Leu Phe His Pro Glu Asp Thr Gly Gln Val
 1               5                  10

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide

<400> SEQUENCE: 84

Phe His Pro Glu Asp Thr Gly Gln Val Lys
 1               5                  10

<210> SEQ ID NO 85
<211> LENGTH: 10
<212> TYPE: PRT
<213> ORGANISM: Artificial Sequence
<220> FEATURE:
<223> OTHER INFORMATION: Synthetic peptide

<400> SEQUENCE: 85

Glu Asp Thr Gly Gln Val Lys Lys Thr Thr
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

Asp Thr Gly Gln Val Lys Lys Thr Thr Asn
 1               5                  10

<210> SEQ ID NO 87
<211> LENGTH: 10
<212> TYPE: PRT
<213> ORGANISM: Artificial Sequence
<220> FEATURE:
<223> OTHER INFORMATION: Synthetic peptide

<400> SEQUENCE: 87

Thr Gly Gln Val Lys Lys Thr Thr Asn Val
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Gly Gln Val Lys Lys Thr Thr Asn Val His
 1               5                  10

<210> SEQ ID NO 89
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 89

Gln Val Lys Lys Thr Thr Asn Val His Ser
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

Val Lys Lys Thr Thr Asn Val His Ser Leu
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide

<400> SEQUENCE: 91

Leu Thr Pro Lys Lys Thr Thr Asn Val Leu
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic peptide

<400> SEQUENCE: 92

Thr Pro Lys Lys Thr Thr Asn Val Leu Thr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic peptide

<400> SEQUENCE: 93

Pro Lys Lys Thr Thr Asn Val Leu Thr Val
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide

<400> SEQUENCE: 94

Lys Lys Thr Thr Asn Val Leu Thr Val Pro
1               5                   10

<210> SEQ ID NO 95
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 95

Lys Lys Thr Thr Asn Val His Ser Leu Phe
 1               5                  10

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide

<400> SEQUENCE: 96

Lys Thr Thr Asn Val His Ser Leu Phe His
 1               5                  10

<210> SEQ ID NO 97
<211> LENGTH: 10
<212> TYPE: PRT
<213> ORGANISM: Artificial Sequence
<220> FEATURE:
<223> OTHER INFORMATION: Synthetic peptide

<400> SEQUENCE: 97

Lys Thr Thr Asn Val Leu Thr Val Pro Thr
 1               5                  10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide

<400> SEQUENCE: 98

Thr Thr Asn Val Leu Thr Val Pro Thr Asn
 1               5                  10

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide

<400> SEQUENCE: 99

Thr Asn Val Leu Thr Val Pro Thr Asn Ile
 1               5                  10

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

Asn Val Leu Thr Val Pro Thr Asn Ile Pro
 1               5                  10

<210> SEQ ID NO 101
<211> LENGTH: 10
<212> TYPE: PRT
<213> ORGANISM: Artificial Sequence
<220> FEATURE:
```

```
-continued

<223> OTHER INFORMATION: Synthetic peptide

<400> SEQUENCE: 101

Val Leu Thr Val Pro Thr Asn Ile Pro Gly
 1               5                  10

<210> SEQ ID NO 102
<211> LENGTH: 18
<212> TYPE: PRT
<213> ORGANISM: Artificial Sequence
<220> FEATURE:
<223> OTHER INFORMATION: Synthetic peptide

<400> SEQUENCE: 102

Pro Glu Asp Thr Gly Gln Val Lys Lys Thr Thr Asn Val His Ser Leu
 1               5                  10                  15

Phe His
```